(12) United States Patent
Ruiz-Lozano et al.

(10) Patent No.: US 10,682,416 B2
(45) Date of Patent: Jun. 16, 2020

(54) EPICARDIAL-DERIVED PARACRINE FACTORS FOR REPAIRING CARDIAC TISSUE

(71) Applicants: Regencor, Inc., Los Altos, CA (US); Sanford Burnham Prebys Medical Discovery Institute, La Jolla, CA (US); EPIKABIO, INC., Los Altos, CA (US)

(72) Inventors: Pilar Ruiz-Lozano, Los Altos, CA (US); Mark Mercola, La Jolla, CA (US); Ke Wei, Shanghai (CN)

(73) Assignees: Regencor, Inc., Los Altos, CA (US); Sanford Burnham Prebys Medical Discovery Institute, La Jolla, CA (US)

( * ) Notice: Subject to any disclaimer, the term of this patent is extended or adjusted under 35 U.S.C. 154(b) by 79 days.

(21) Appl. No.: 15/565,054

(22) PCT Filed: Apr. 8, 2016

(86) PCT No.: PCT/US2016/026809
§ 371 (c)(1),
(2) Date: Oct. 6, 2017

(87) PCT Pub. No.: WO2016/164840
PCT Pub. Date: Oct. 13, 2016

(65) Prior Publication Data
US 2018/0092980 A1   Apr. 5, 2018

Related U.S. Application Data

(60) Provisional application No. 62/196,766, filed on Jul. 24, 2015, provisional application No. 62/145,480, filed on Apr. 9, 2015.

(51) Int. Cl.
| | |
|---|---|
| *A61K 38/00* | (2006.01) |
| *A61K 38/16* | (2006.01) |
| *C07K 1/00* | (2006.01) |
| *A61K 47/42* | (2017.01) |
| *A61K 35/34* | (2015.01) |
| *A61K 9/00* | (2006.01) |
| *A61K 9/70* | (2006.01) |
| *A61K 38/17* | (2006.01) |
| *A61K 31/7072* | (2006.01) |
| *A61P 9/10* | (2006.01) |
| *A61K 38/18* | (2006.01) |

(52) U.S. Cl.
CPC ............ *A61K 47/42* (2013.01); *A61K 9/0024* (2013.01); *A61K 9/7007* (2013.01); *A61K 31/7072* (2013.01); *A61K 35/34* (2013.01); *A61K 38/1709* (2013.01); *A61K 38/1875* (2013.01); *A61P 9/10* (2018.01)

(58) Field of Classification Search
None
See application file for complete search history.

(56) References Cited

U.S. PATENT DOCUMENTS

| | | |
|---|---|---|
| 8,741,584 B2 | 6/2014 | Hirsch et al. |
| 2009/0326053 A1 | 12/2009 | Walsh et al. |
| 2010/0227817 A1 | 9/2010 | Walsh et al. |
| 2010/0330044 A1 | 12/2010 | Blanpain et al. |
| 2011/0104735 A1 | 5/2011 | Buehrer et al. |
| 2013/0295064 A1 | 11/2013 | Singla |

OTHER PUBLICATIONS

Magadum et al. 2018. Molecular Therapy: Nucleic Acids 3:133-143 (Year: 2018).*
Extended European Search Report dated Nov. 19, 2018, for EP Patent Application No. 16777438.9, 10 pages.
International Search Report dated Aug. 8, 2016, for PCT Application No. PCT/US2016/026809, filed Apr. 8, 2016, 4 pages.
Li, K.C. et al. (Mar. 10, 2011). "Follistatin-like 1 suppresses sensory afferent transmission by activating Na+,K+-ATPase," *Neuron* 69(5):974-987.
Ogura, Y. et al. (Oct. 2, 2012, e-published Aug. 28, 2012). "Therapeutic impact of follistatin-like 1 on myocardial ischemic injury in preclinical models" *Circulation* 126(14):1728-1738, Supplementary Material, 9 pages.
Wei, K. et al. (Sep. 24, 2015, e-published Sep. 16, 2015). "Epicardial FSTL1 reconstitution regenerates the adult mammalian heart," *Nature* 525(7570):479-485.
Written Opinion dated Aug. 8, 2016, for PCT Application No. PCT/US2016/026809, filed Apr. 8, 2016, 5 pages.

* cited by examiner

*Primary Examiner* — Shulamith H Shafer
(74) *Attorney, Agent, or Firm* — Mintz Levin Cohn Ferris Glovsky and Popeo PC

(57) ABSTRACT

Provided herein, inter alia, are compositions and kits comprising epicardial-derived paracrine factors (such as, hypoglycosylated follistatin-like 1 (FSTL1)) for treating and repairing damage to cardiac tissue caused by cardiovascular disease, myocardial infarction (MI), other ischemic events, or cardiac-growth deficiency, as well as methods for using the same.

15 Claims, 31 Drawing Sheets

Specification includes a Sequence Listing.

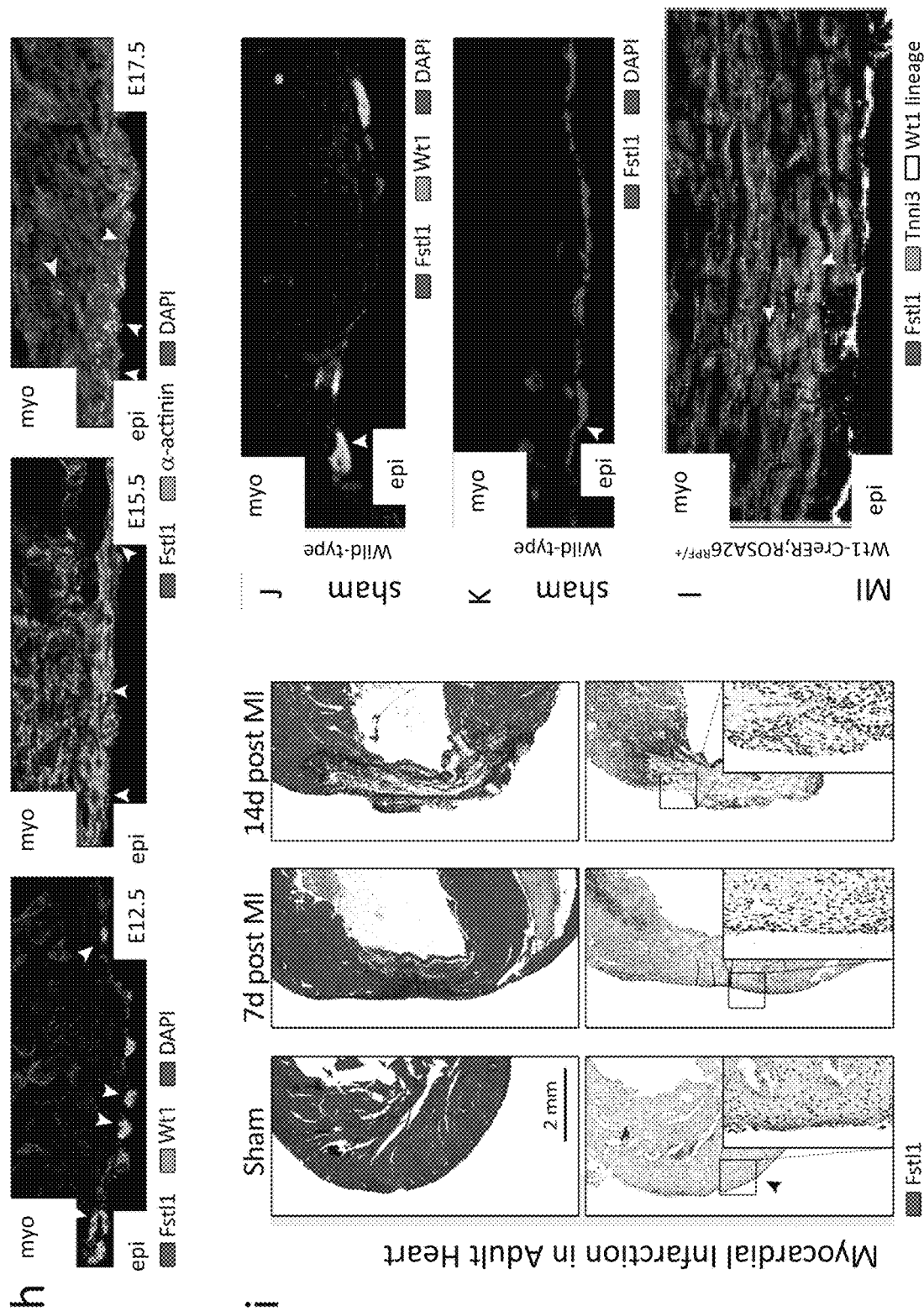
Figure 3 (con't.)

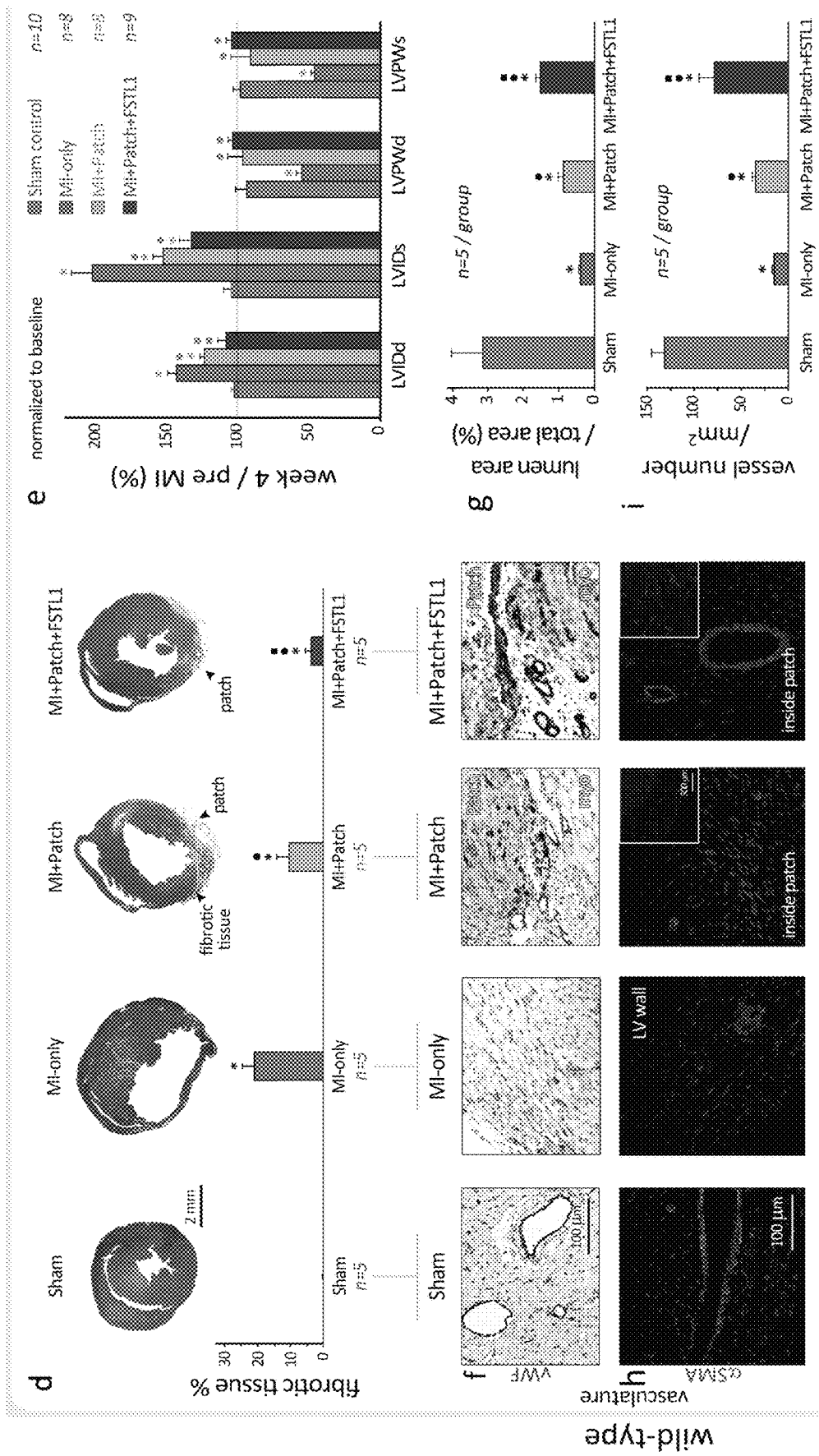
Figure 4 (con't.)

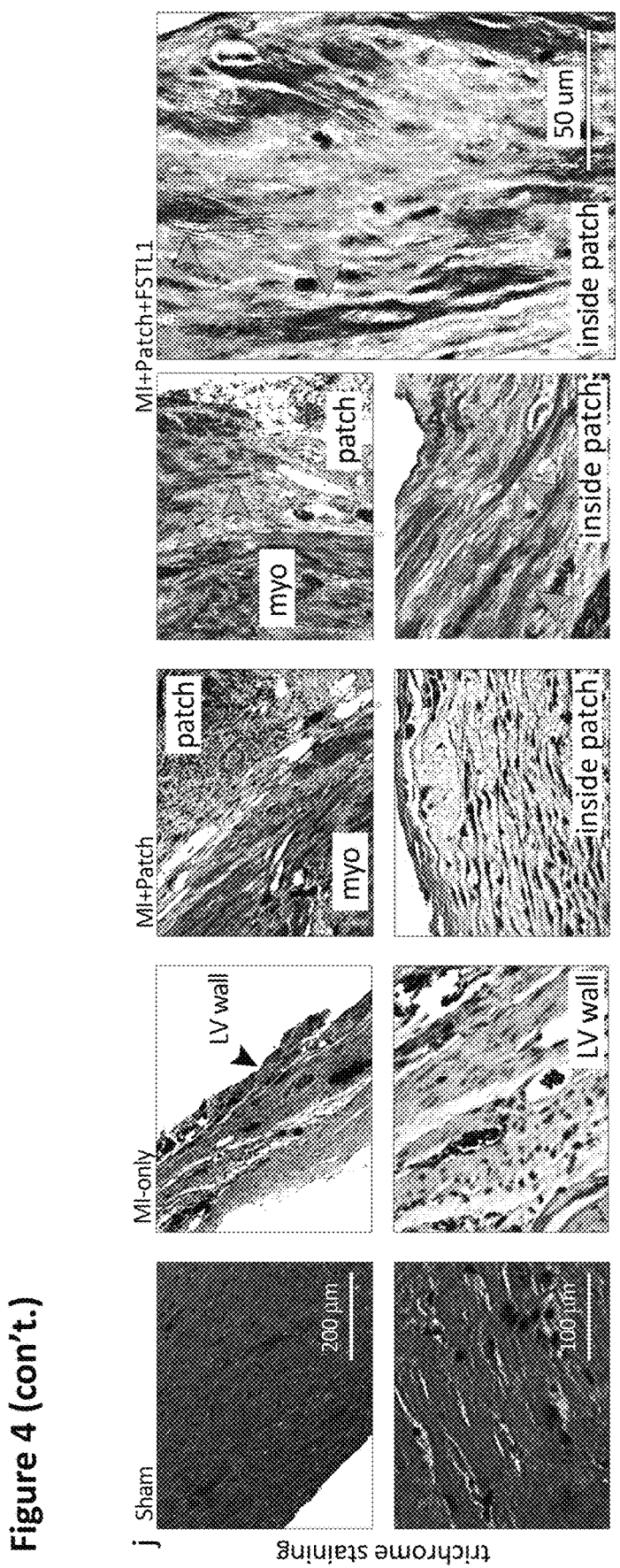
Figure 4 (con't.)

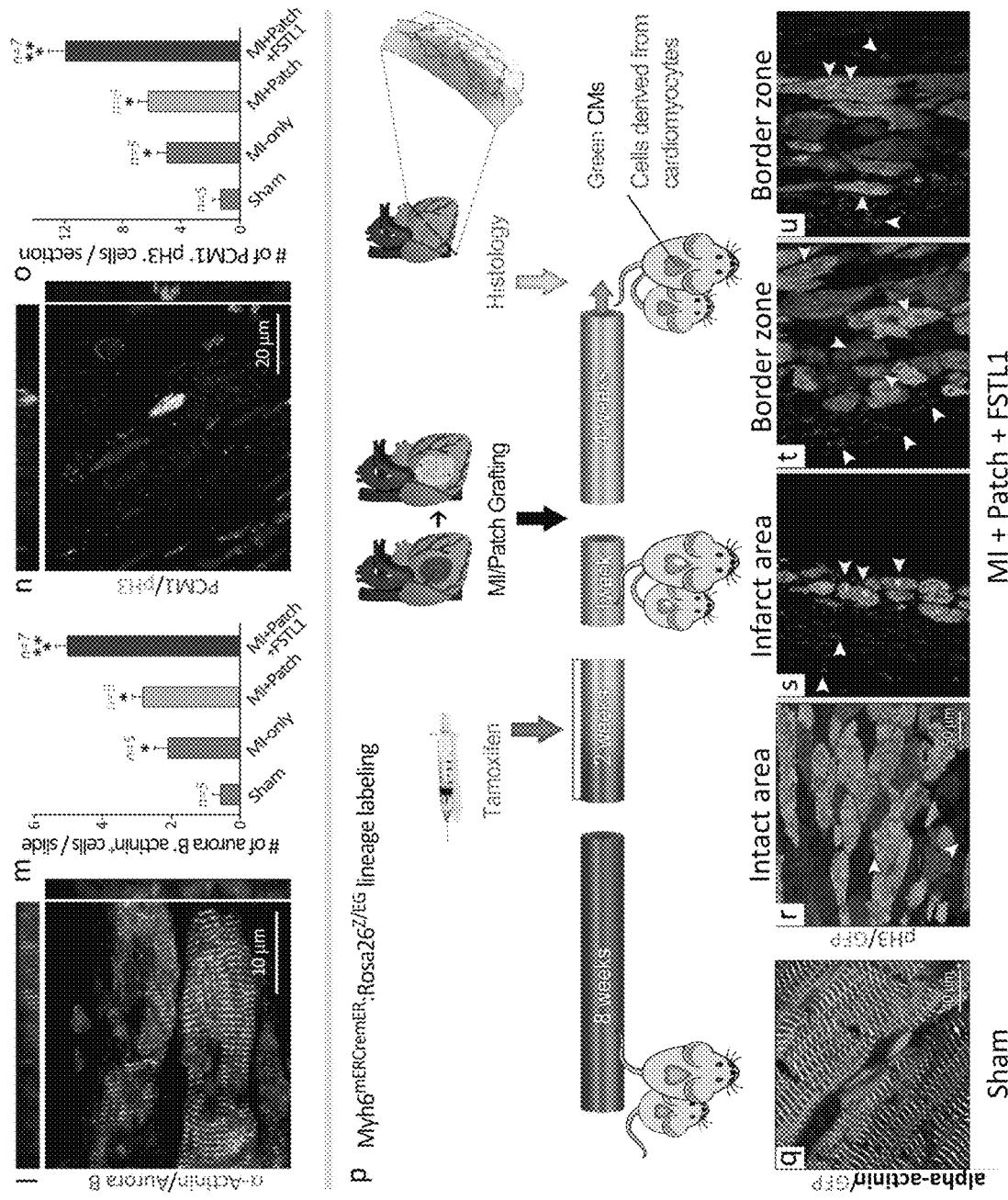

Figure 6 (con't.)
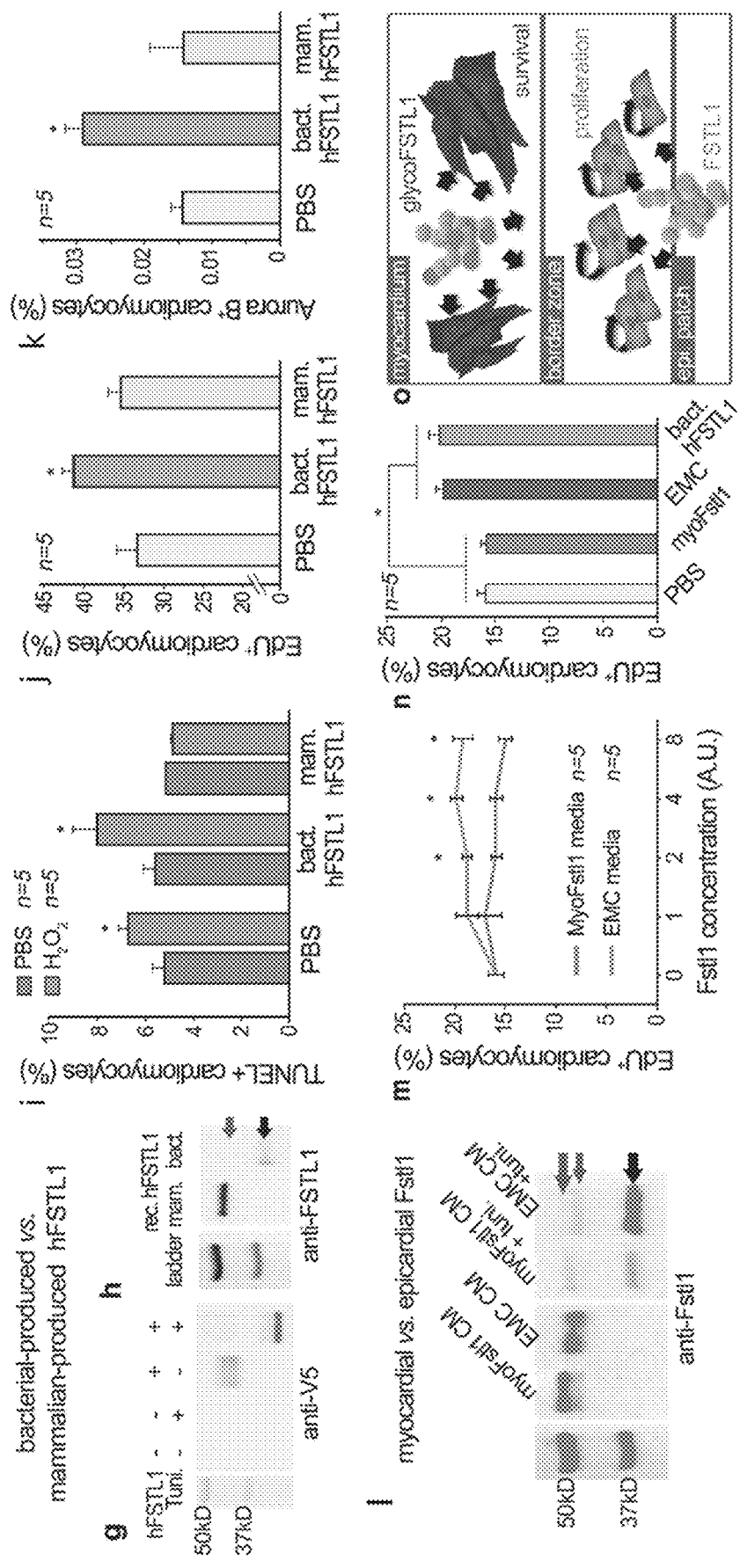

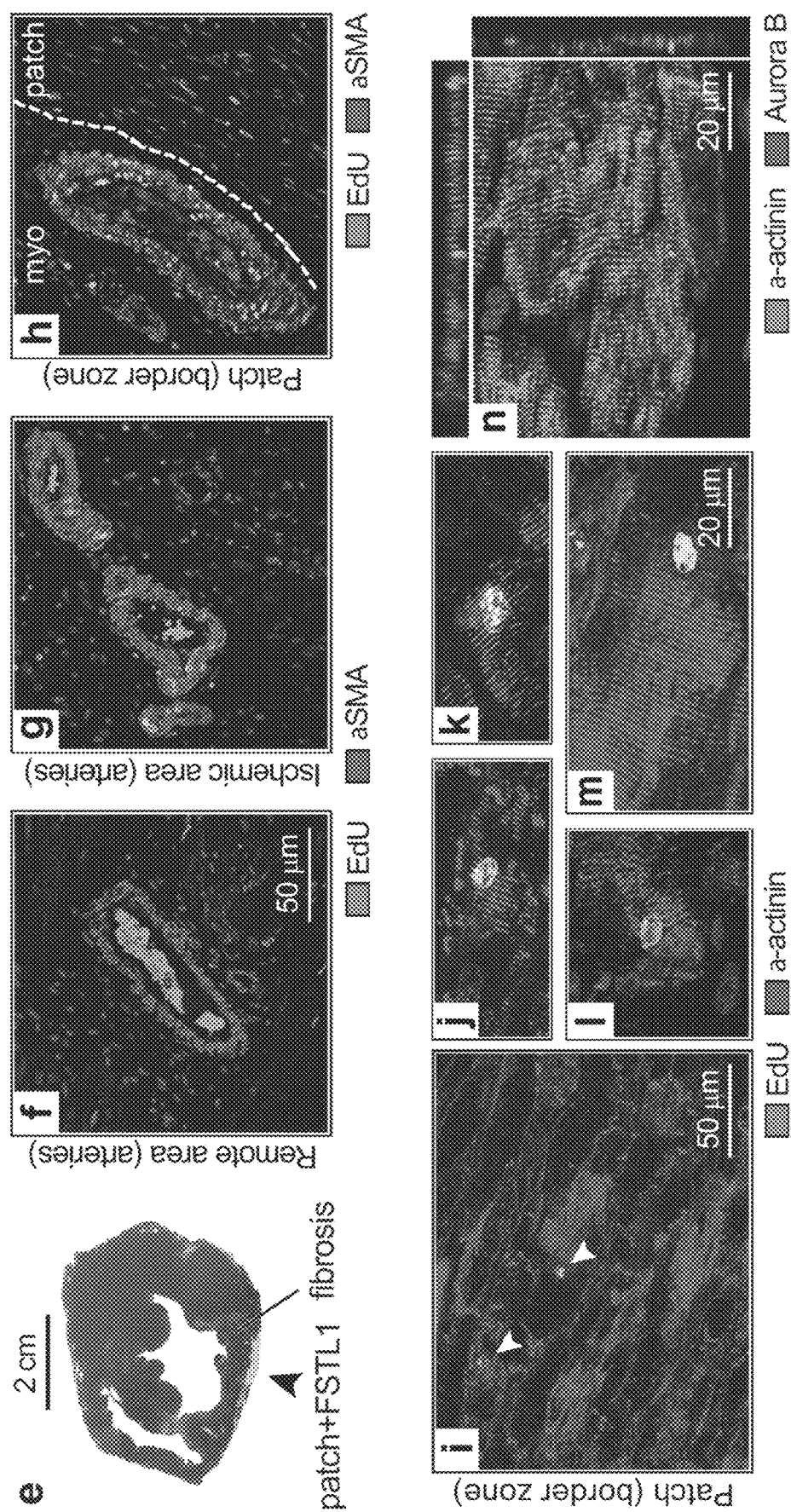
Figure 7 (con't.)

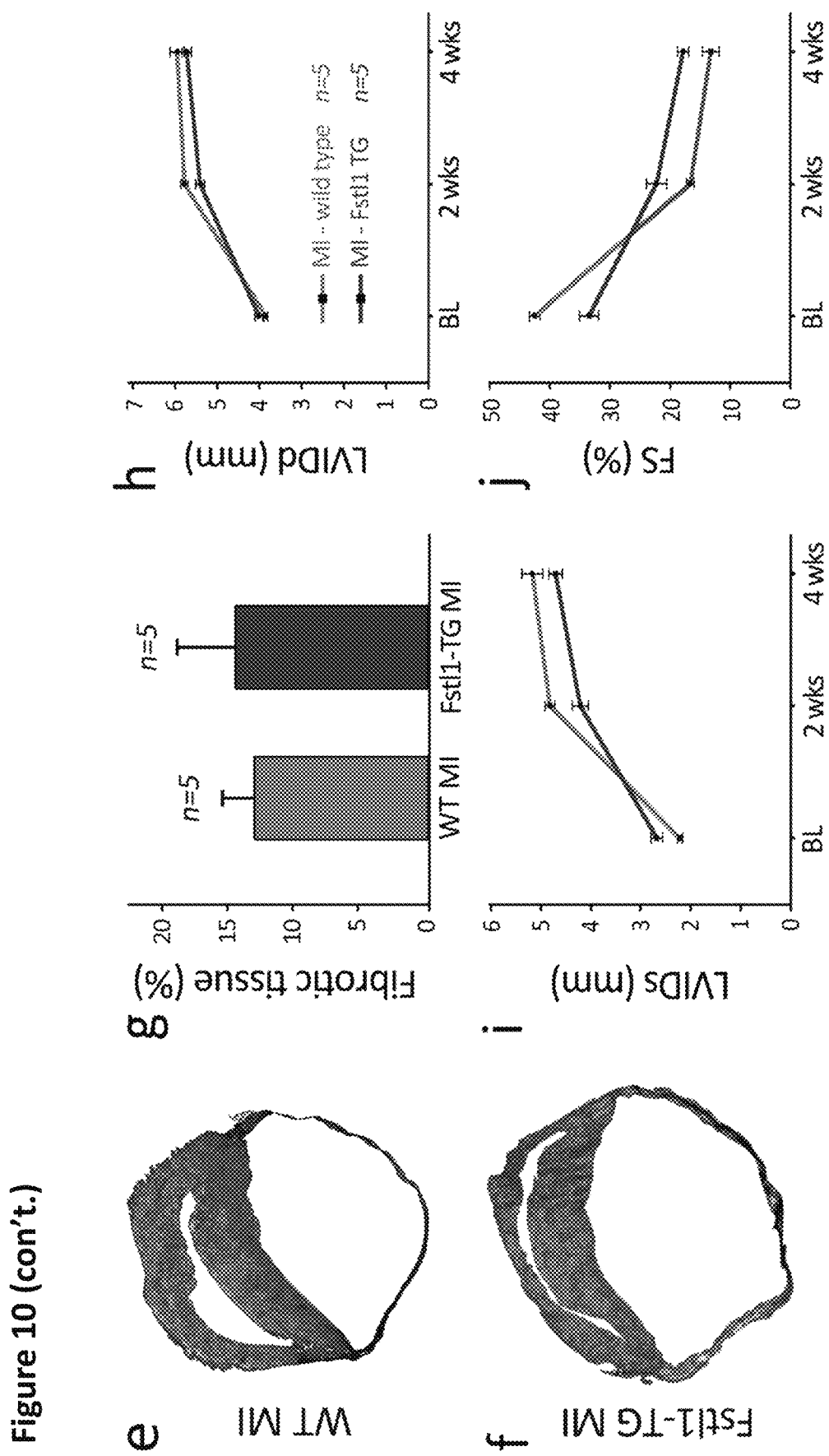
Figure 10 (con't.)

Figure 10 (con't.)
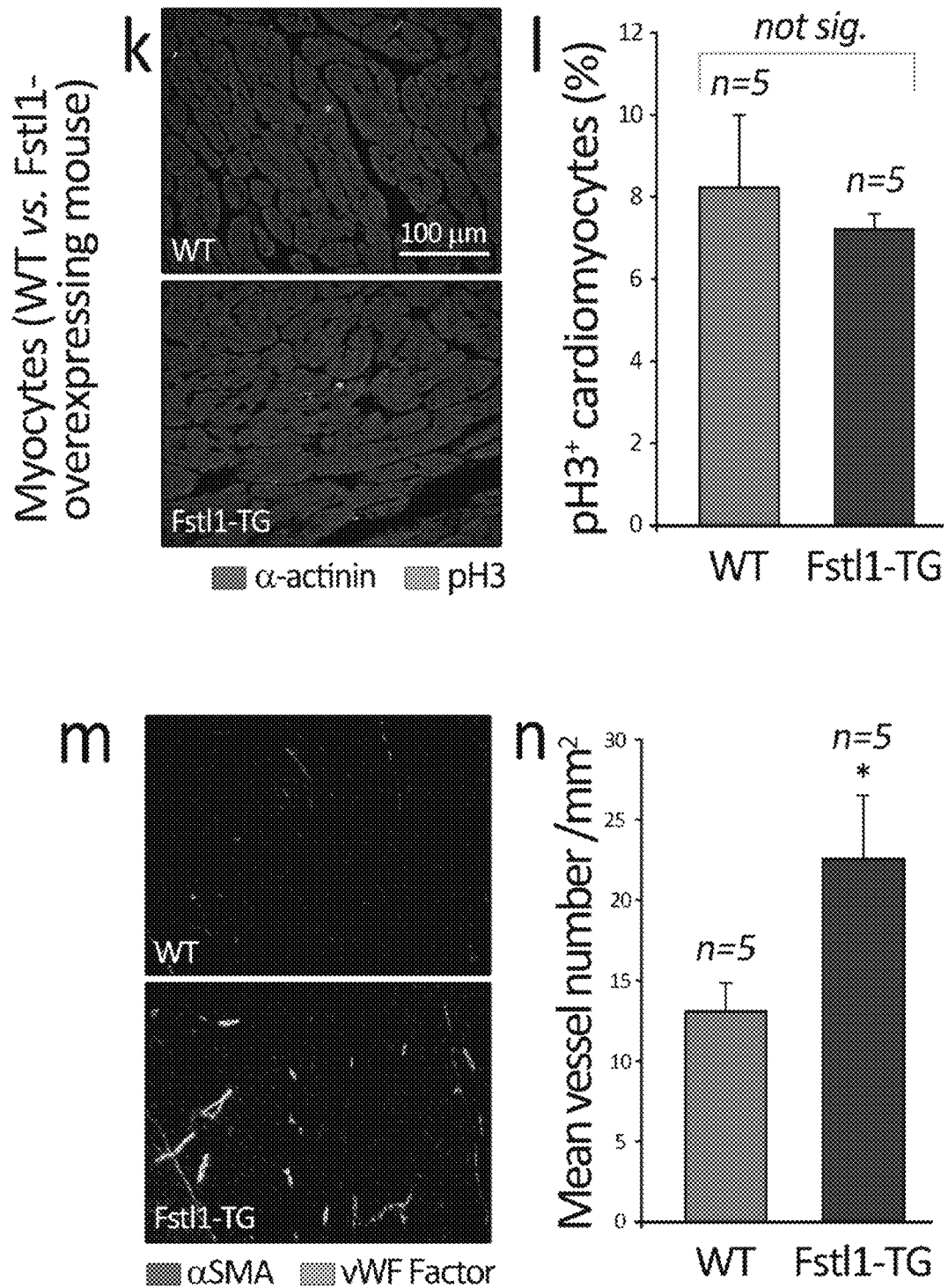

Figure 12 (con't.)
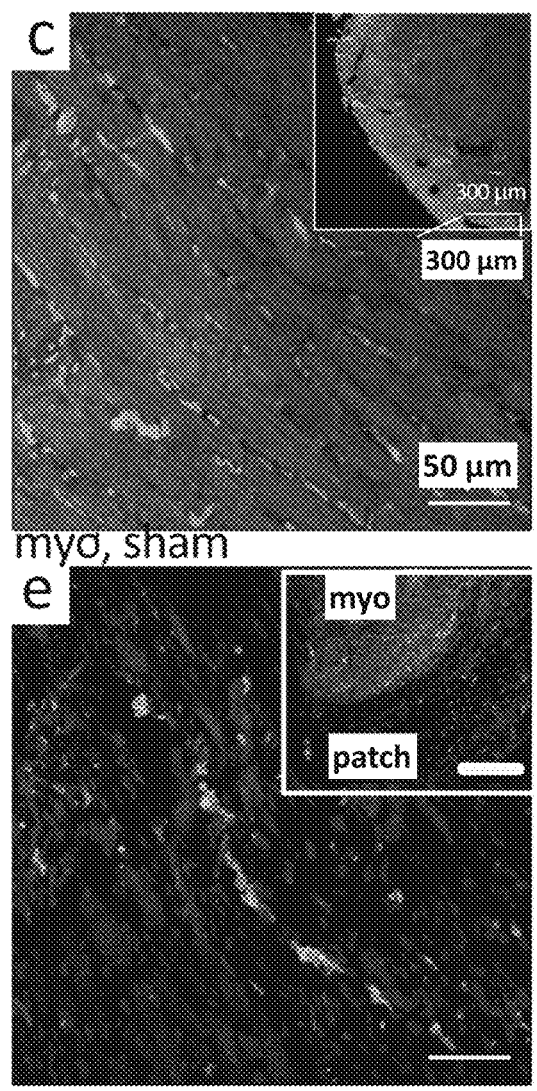
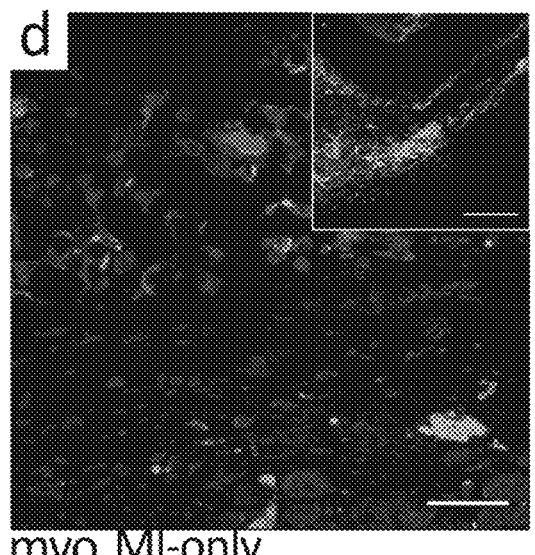
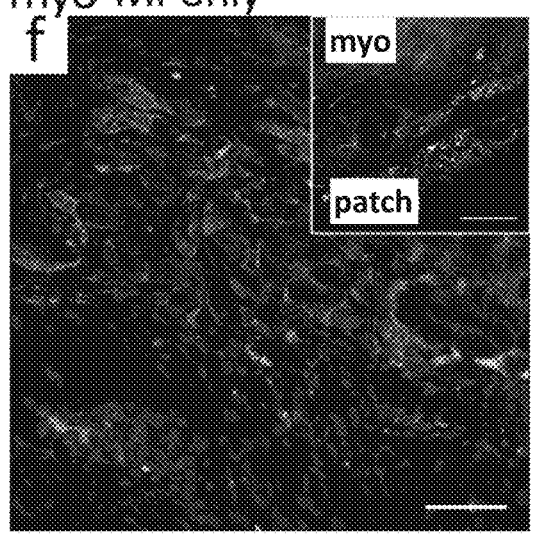
Inside patch, MI+Patch    Inside patch, MI+Patch+FSTL1

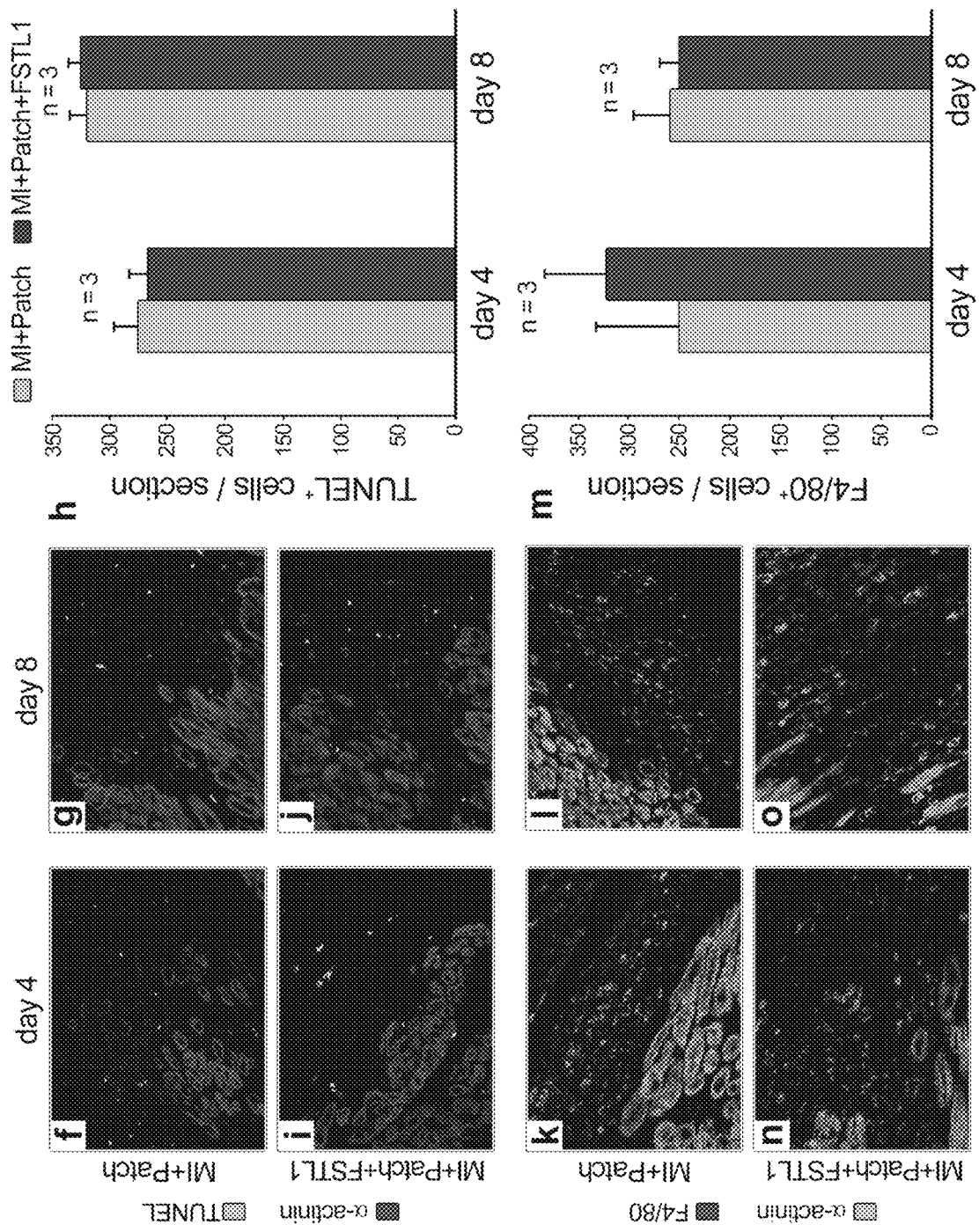
Figure 17 (con't.)

Figure 18 (con't.)

EPICARDIAL-DERIVED PARACRINE FACTORS FOR REPAIRING CARDIAC TISSUE

CROSS-REFERENCE TO RELATED APPLICATIONS

This application is a national stage application, filed under 35 U.S.C. § 371, of International Patent Application No. PCT/US2016/026809, filed on Apr. 8, 2016, which claims priority to U.S. Provisional Patent Application No. 62/145,480, filed Apr. 9, 2015 and U.S. Provisional Patent Application No. 62/196,766, filed Jul. 24, 2015, the disclosures of which are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 048722_501N01US_Seq_Listing.txt, original date created: Jan. 3, 2018, size: 13.9 KB)

FIELD OF INVENTION

This invention relates, inter alia, to compositions comprising epicardial-derived paracrine factors as well as use of the same to treat or prevent damage to cardiac (e.g., myocardial) tissue following ischemic events such as myocardial infarction.

BACKGROUND

Acute myocardial infarction (AMI) is one of the leading causes of death in the Western world and many risk factors, both environmental and genetic, contribute to its pathogenesis. The heart generally lacks an endogenous regenerative capacity sufficient for repair after injury. Consequential left ventricular (LV) remodeling after myocardial infarction (MI) or other ischemic events leads to LV dilatation and ultimately to heart failure (Holmes et al., 2005, *Annu Rev Biomed Eng.*; 7:223-53). Immediately after coronary occlusion, ischemic myocytes downstream from the occlusion become necrotic and/or undergo apoptosis. Neutrophils infiltrate the tissue immediately, while leukocytes, predominantly macrophages, arrive shortly thereafter and participate in digestion of necrotic cellular debris. Neutrophils in the ischemic tissue can be toxic to the surrounding myocytes, because they release reactive oxygen species and proteolytic enzymes which further injure the surrounding myocytes (Nah & Rhee, *Korean Circ J.*; October; 39(10):393-82009). Once damage occurs, a hypocellular scar forms that leads to contractile dysfunction and eventual heart failure.

To reduce the epidemiologic and fiscal burden associated with ischemic events affecting the myocardium, it is imperative that new compositions and strategies be developed to preserve cardiomyocyte survival or stimulate cardiomyocyte growth following injury caused by ischemic events such as myocardial infarction. There is a need for therapies that can address and/or treat cardiac (e.g., myocardial) tissue following an injury. The invention disclosed herein addresses these needs and provides additional benefits as well.

SUMMARY

Provided herein, inter alia, are compositions and kits comprising epicardial-derived paracrine factors (e.g., hypoglycosylated follistatin-like 1 (FSTL1) for treating and repairing damage to cardiac (e.g., myocardial) tissue caused by cardiovascular disease, myocardial infarction (MI), or other ischemic events as well as methods for using the same.

Accordingly, in some aspects, provided herein are methods for repairing cardiac (e.g., myocardial) tissue following an injury in a subject in need thereof, the method comprising contacting the cardiac (e.g., myocardial) tissue with an epicardial-derived paracrine factor. In some embodiments, the epicardial-derived paracrine factor is a hypoglycosylated follistatin-like 1 (FSTL1) polypeptide. In some embodiments of any of the embodiments disclosed herein, the injury is an ischemia reperfusion cardiac (e.g., myocardial) injury, is due to ischemic heart disease, and/or is due to a hypoplastic heart. In some embodiments of any of the embodiments disclosed herein, the injury is a myocardial infarction and/or the heart contains scar tissue. In some embodiments of any of the embodiments disclosed herein, repairing cardiac (e.g., myocardial) tissue comprises increasing the number of cardiomyocytes in the cardiac (e.g., myocardial) tissue. In some embodiments, the number of cardiomyocytes is increased at least two fold compared to the number of cardiomyocytes in the injured scar tissue that is not contacted by an epicardial-derived paracrine factor following an injury. In some embodiments of any of the embodiments disclosed herein, repairing cardiac (e.g., myocardial) tissue comprises improved percent fractional shortening of cardiac (e.g., myocardial) tissue compared to the amount of percent fractional shortening in cardiac (e.g., myocardial) tissue that is not contacted by an epicardial-derived paracrine factor following an injury. In some embodiments of any of the embodiments disclosed herein, repairing cardiac (e.g., myocardial) tissue comprises improving wall motion, compared to the same subject prior to treatment. In some embodiments of any of the embodiments disclosed herein, repairing cardiac (e.g., myocardial) tissue comprises improving blood perfused area, compared to the same subject prior to treatment. In some embodiments of any of the embodiments disclosed herein, repairing cardiac (e.g., myocardial) tissue comprises decreasing cardiac (e.g., myocardial) incidents and hospitalizations, compared to similar subjects without treatment. In some embodiments of any of the embodiments disclosed herein, repairing cardiac (e.g., myocardial) tissue comprises an increase in the amount of cardiomyocyte cytokinesis in the cardiac (e.g., myocardial) tissue compared to the amount of cardiomyocyte cytokinesis in cardiac (e.g., myocardial) tissue that is not contacted by an epicardial-derived paracrine factor following an injury. In some embodiments, an increase in the amount of cardiomyocyte cytokinesis is determined by expression of Aurora B kinase. In some embodiments of any of the embodiments disclosed herein, repairing cardiac (e.g., myocardial) tissue comprises decreased cardiomyocyte apoptosis. In some embodiments of any of the embodiments disclosed herein, said method results in increased levels of transcripts encoding cardiac (e.g., myocardial)-specific contractile proteins in cardiomyocytes. In some embodiments, said method results in a 2 fold increase in the levels of transcripts encoding cardiac (e.g., myocardial)-specific contractile proteins in cardiomyocytes. In some embodiments of any of the embodiments disclosed herein, the cardiac (e.g., myocardial)-specific contractile proteins are selected from the group consisting of myh6, mlc2v, and mlc2a. In some embodiments of any of the embodiments disclosed herein, said method results in increased actinin$^+$ cells with rhythmic contractile $Ca^{2+}$ in cardiomyocytes. In some embodiments of any of the embodiments disclosed herein, the cardiac (e.g., myocardial) tissue is contacted with said epicardial-derived paracrine factor immediately following the injury. In some embodiments of any of the embodiments disclosed herein, said method increases survival of the subject following the injury. In some embodiments of any of the embodiments disclosed herein, said method attenuates fibrosis in the cardiac (e.g., myocardial) tissue following the injury. In some embodiments of any of the embodiments disclosed herein, said method results in increased vascularization of the injured region of the cardiac (e.g., myocardial) tissue. In some embodiments, said increased vascularization is determined by expression of von Willebrand factor (vWF) or smooth muscle actin in blood vessel cells. In some embodiments of any of the embodiments disclosed herein, said method induces cardiomyocyte cell cycle entry. In some embodiments, said cardiomyocyte cell cycle entry is assessed by expression of phosphor-Histone H3. In some embodiments of any of the embodiments disclosed herein, said method results in an at least 2 fold increase in cardiomyocyte cell cycle entry compared to the amount of cardiomyocyte cell cycle entry in cardiac (e.g., myocardial) tissue that is not contacted by an epicardial-derived paracrine factor following an injury. In some embodiments, said hypoglycosylated FSTL1 polypeptide is synthesized in a prokaryotic cell. In some embodiments, said prokaryotic cell is a bacterial cell. In some embodiments, said hypoglycosylated FSTL1 polypeptide is synthesized in a eukaryotic cell that is treated with an inhibitor of glycosylation. In some embodiments, said inhibitor of glycosylation is tunicamycin. In some embodiments, the hypoglycosylated FSTL1 polypeptide is generated by substituting one or more glycosylated amino acids with one or more glycosylation incompetent amino acids. In some embodiments, said one or more glycosylated amino acids are selected from the group consisting of N144, N175, N180, and N223. In some embodiments of any of the embodiments disclosed herein, said hypoglycosylated FSTL1 polypeptide does not protect cardiomyocytes from apoptosis following injury. In some embodiments of any of the embodiments disclosed herein, the hypoglycosylated FSTL1 polypeptide is injected directly into the injured mycocardial tissue. In some embodiments of any of the embodiments disclosed herein, the hypoglycosylated FSTL1 polypeptide is delivered systemically. In some embodiments of any of the embodiments disclosed herein, the hypoglycosylated FSTL1 polypeptide is delivered endocardially. In some embodiments of any of the embodiments disclosed herein, the hypoglycosylated FSTL1 polypeptide is embedded or seeded into a three dimensional collagen patch. In some embodiments of any of the embodiments disclosed herein, the hypoglycosylated FSTL1 polypeptide is embedded or seeded into a hydrogel. In some embodiments of any of the embodiments disclosed herein, the cardiac (e.g., myocardial) tissue is contacted from one or more of an epicardial site, an endocardial site, and/or through direct injection into the myocardium.

In another aspect, provided herein are pharmaceutical compositions comprising a hypoglycosylated follistatin-like 1 (FSTL1) polypeptide and one or more pharmaceutically acceptable excipients. In some embodiments, said hypoglycosylated FSTL1 polypeptide is synthesized in a prokaryotic cell. In some embodiments, said prokaryotic cell is a bacterial cell. In some embodiments, said hypoglycosylated FSTL1 polypeptide is synthesized in a eukaryotic cell that is treated with an inhibitor of glycosylation. In some embodiments, said inhibitor of glycosylation is tunicamycin. In some embodiments, said hypoglycosylated FSTL1 polypeptide is obtained by genomic editing. In some embodiments, said hypoglycosylated FSTL1 polypeptide is obtained by insertion of modified RNAs. In some embodiments, said hypoglycosylated FSTL1 polypeptide is obtained by drug treatment of subjects (e.g., such that a treatment inhibits the glycosylation of the endogenous FSTL1 polypeptide). In some embodiments of any of the embodiments disclosed herein, the composition is formulated for injection directly into the injured cardiac (e.g., myocardial) tissue. In some embodiments of any of the embodiments disclosed herein, the composition is formulated for systemic administration. In some embodiments of any of the embodiments disclosed herein, the hypoglycosylated FSTL1 polypeptide is embedded or seeded into a three dimensional (3D) collagen patch. In some embodiments, the 3D collagen patch has an elastic modulus of 12±4 kPa.

In further aspects, provided herein are kits comprising (i) a hypoglycosylated follistatin-like 1 (FSTL1) polypeptide; and (ii) one or more pharmaceutically acceptable excipients. In some embodiments, the kit further comprises (iii) a three dimensional (3D) collagen patch. In some embodiments of any of the embodiments disclosed herein, the hypoglycosylated FSTL1 polypeptide is embedded or seeded into a three dimensional (3D) collagen patch. In some embodiments of any of the embodiments disclosed herein, the 3D collagen patch has an elastic modulus of 12±4 kPa. In some embodiments of any of the embodiments disclosed herein, the kit further comprises (iv) adhesion means for adhering the 3D collagen patch to the epicardium or to the myocardium of an injured heart. In some embodiments, said adhesion means are sutures.

In yet other aspects, provided herein are methods for repairing cardiac (e.g., myocardial) tissue following an injury in a subject in need thereof, the method comprising contacting the cardiac (e.g., myocardial) tissue with a three dimensional (3D) collagen patch seeded or infused with a recombinant hypoglycosylated follistatin-like 1 (FSTL1) polypeptide. In some embodiments, the injury is an ischemia reperfusion injury. In some embodiments, the injury is a myocardial infarction. In some embodiments of any of the embodiments disclosed herein, the 3D collagen patch is sutured to the cardiac (e.g., myocardial) tissue.

In another aspect, provided herein is a three dimensional (3D) collagen patch infused or seeded with a recombinant hypoglycosylated follistatin-like 1 (FSTL1) polypeptide. In some embodiments, said recombinant hypoglycosylated FSTL1 polypeptide is synthesized in a prokaryotic cell. In some embodiments, said prokaryotic cell is a bacterial cell. In some embodiments, said recombinant hypoglycosylated FSTL1 polypeptide is synthesized in a eukaryotic cell that is treated with an inhibitor of glycosylation. In some embodiments, said inhibitor of glycosylation is tunicamycin. In some embodiments of any of the embodiments disclosed herein, the 3D collagen patch has an elastic modulus of 12±4 kPa.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

Number of Sca1+ cells after 72 hours FSTL1 treatment (n=5). No significant change is found upon FSTL1 treatment.

Figure 19:
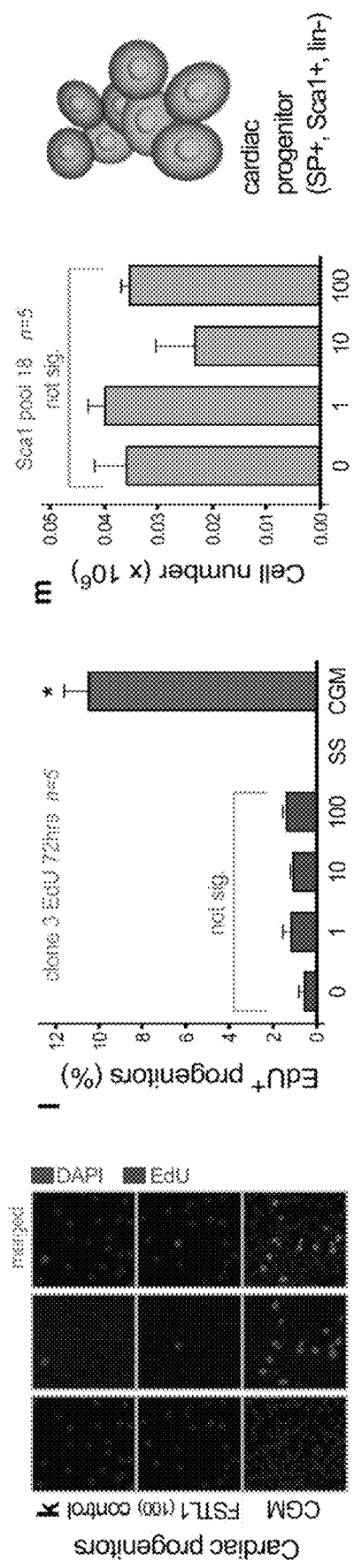
Figure 19:
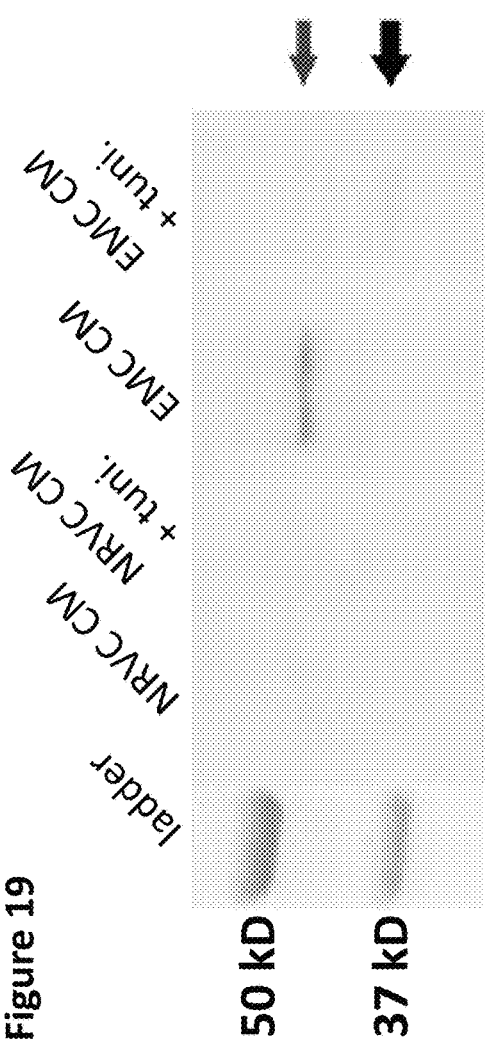

FIG. 19 depicts FSTL1 detection in NRVC and EMC conditioned media. Western blot against FSTL1 of conditioned media of NRVC and conditioned media of EMC, treated with or without Tunicamycin, showing secretion of glycosylated FSTL1 in EMC but not NRVC.

Figure 20:
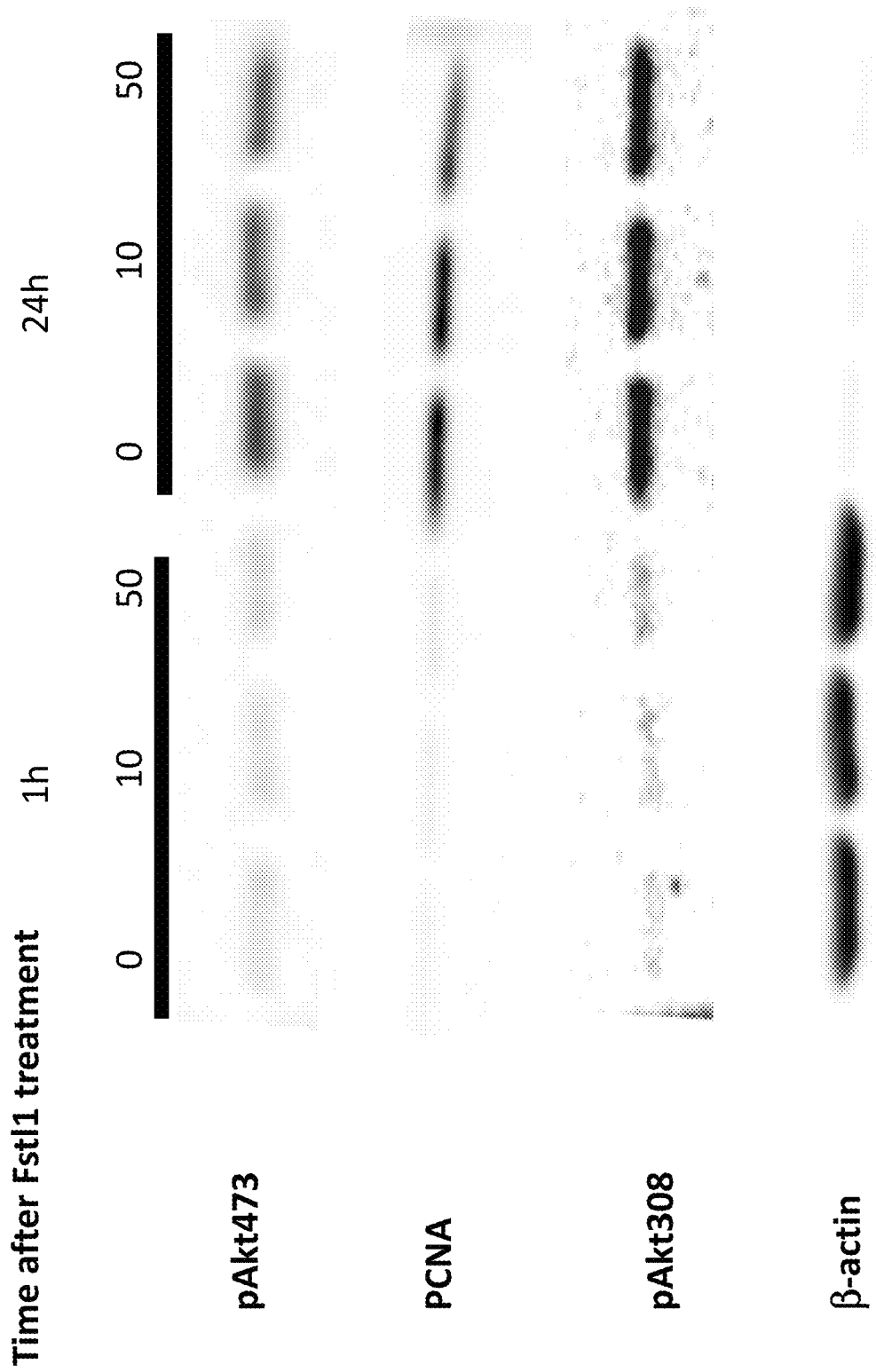

FIG. 20 depicts phosphor-Akt and PCNA detections in mCMs$^{ESC}$ after FSTL1 treatment. Western blot against phosphor-Akt (Ser473 and Thr308, both indicated in survival response in cardiomyocytes), and PCNA (proliferation marker) after 1 hour and 24 hours of FSTL1 treatment at 10 ng/ml and 50 ng/ml, showing no change in phosphor-Akt as well as PCNA upon FSTL1 treatment.

DETAILED DESCRIPTION

The invention disclosed herein is based, in part, on the inventors' observation that conditioned media obtained from epicardial-like cell cultures enhance cardiomyogenesis in vitro and in the adult injured heart. The epicardium of the heart is an external epithelial layer that contributes to myocardial growth during development by providing progenitor cells[1,2] as well as mitogens, including FGFs, IGF2, and PDGFs[3-5]. Recent studies suggest that the epicardium might also preserve function of the adult myocardium following injury, possibly as a source of myogenic progenitors[6,7]. However, to date, no epicardial-derived paracrine factors have yet been shown to support myocardial regeneration in mammals following injury, although identification of such factors as well as their mechanism of action would provide insight into this poorly understood and inherently inefficient process[8].

As further detailed below, after subjecting the conditioned media to mass-spectrometry followed by subsequent analyses, follistatin-like 1 (FSTL1) was identified as a component of the observed cardiomyogenic activity. FSTL1 was seen to be expressed in the adult epicardium but declined strikingly following myocardial infarction (MI) wherein it was then replaced by myocardial expression. As exemplified below in a non-limiting example, while endogenous myocardial or transgenic overexpression in myocardium had no regenerative effect, application of FSTL1 to the epicardial surface of the heart by a compressed collagen patch recapitulated the activity of epicardial-conditioned media. In some embodiments, the engineered FSTL1 epicardial treatment diminished pathological remodeling, restored vascularization, and induced cell cycle entry of pre-existing αMHC+ cells after MI, consequently improving cardiac function. As further shown in the non-limiting examples described below, in vitro studies indicated that FSTL1 stimulated proliferation of immature myocytes rather than progenitor cells. In some embodiments, the pro-proliferative properties of FSTL1 correlate with tissue-specific post-transcriptional modifications of the protein, such as its glycosylation status. In other embodiments of the present invention, administration of hypoglycosylated FSTL1 does not activate Akt-1 signaling activity. In a further non-limiting example described below, epicardial patch delivery of hypo-glycosylated FSTL1 was also efficacious in a preclinical swine model of myocardial infarction, highlighting evolutionary conservation of this regenerative mechanism in mammals. As such, without being bound to theory, engineered epicardial delivery of FSTL1 has the potential to be an attractive option to achieve therapeutic regeneration of cardiomyocytes following ischemic injury.

I. Definitions

The phrase "cardiac tissue," as used herein, refers to any tissue of the heart. Cardiac tissue includes myocardial tissue, tissue of the epicardium, and tissue of the endocardium. Cardiac tissue comprises any of the cell types found within the heart.

The phrase "epicardial-derived paracrine factor," as used herein, refers to any protein, polypeptide, or fragment thereof produced by the cells of the external epithelial layer of the heart capable of eliciting one or more of a physiological, protective, proliferative, and/or reparative response in the cardiac (e.g., myocardial) tissue following injury due to cardiovascular disease, myocardial infarction, or other ischemic event. In one embodiment, an epicardial-derived paracrine factor is a component of conditioned media obtained from epicardial cell cultures.

The term "hypoglycosylated," as used in the context of the instant invention, refers to a protein that is post-translationally modified with a minimal number carbohydrate moieties or which completely lacks carbohydrate moieties. In some embodiments, hypoglycosylated refers to a protein that completely lacks any carbohydrate modification whatsoever (for example, N-linked glycans, O-linked glycans, or phospho-glycans). In another embodiment, this term refers to a protein with decreased carbohydrate modification (such as any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%) relative to the amount of glycosylation that occurs in vivo under normal physiological conditions in mammalian cells. In another embodiment, this term refers to a protein with decreased carbohydrate modification (such as any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%) relative to the amount of glycosylation that occurs in vivo under normal physiological conditions in mammalian cells. In another embodiment, this term refers to a protein with decreased carbohydrate modification (such as any of about at least 1-100%, 5-95%, 10-90%, 20-80%, 30-70%, 5-10%, 10-20%, 20-30%, 30-40%, 40-50%, 50-60%, 60-70%, 70-80%, 80-90%, 90-100% decreased carbohydrate modification) relative to the amount of glycosylation that occurs in vivo under normal physiological conditions in mammalian cells. In another embodiment, this term refers to a protein with decreased carbohydrate modification (such as any of about at most 1-100%, 5-95%, 10-90%, 20-80%, 30-70%, 5-10%, 10-20%, 20-30%, 30-40%, 40-50%, 50-60%, 60-70%, 70-80%, 80-90%, 90-100% decreased carbohydrate modification) relative to the amount of glycosylation that occurs in vivo under normal physiological conditions in mammalian cells. In yet other embodiments, a hypoglycosylated protein is engineered so that all glycosylation-competent amino acid residues (such as N-linked, O-linked, or phospho-glycan-competent amino acid residues) are substituted with glycosylation-incompetent amino acid residues.

As used herein, the phrase "repairing cardiac tissue following an injury" or "repairing cardiac tissue following injury" refers to any type of action or treatment that decreases, minimizes, or even maintains the level of injury due to cardiovascular disease, myocardial infarction, or other ischemic event. Accordingly, repairing an injury indicates that the subject's condition is not worsened and may be improved with respect to the injury of concern as compared with the level of injury in the absence of treatment or action described herein to reduce injury.

As used herein, "cardiovascular disease" or "heart disease" is a term used to describe a range of diseases or events that affect the heart and/or vasculature. Types of heart disease include, but are not limited to, coronary heart disease, cardiomyopathy, ischemic heart disease, heart failure, inflammatory heart disease, valvular heart disease and aneurysm. Heart disease can be assessed using clinical parameters and/or assessments known to those skilled in the art of diagnosing and/or treating the same, for example, physical examinations, detection of signs and symptoms of cardiovascular disease, electrocardiogram, echocardiogram, chest X-ray, blood tests to detect cardiac biomarkers, etc. Biomarkers typically used in the clinical setting include, but are not limited to, cardiac troponins (C, T, and I), CK and CK-MB, and myoglobin.

As used herein, "myocardial infarction" or "MI" refers to a development of myocardial necrosis, which may be caused by the interruption of blood supply to the heart resulting in a critical imbalance between oxygen supply and demand of the myocardium. This may result from plaque rupture with thrombus formation in a coronary vessel leading to an acute reduction of blood supply to a portion of the myocardium; that is, an occlusion or blockage of a coronary artery following the rupture of a susceptible atherosclerotic plaque. If untreated for a sufficient period of time, the resulting ischemia or restriction in blood supply and oxygen shortage can cause damage or death, i.e., infarction of the heart. In general, this damage is largely irreversible, and clinical therapies thus far mainly aim at delaying the progression of heart failure to prolong survival. Myocardial infarction can be assessed using clinical parameters and/or assessments known to those skilled in the art of diagnosing and/or treating the same, for example, physical examinations, detection of signs and symptoms of myocardial infarction, electrocardiogram, echocardiogram, chest X-ray, blood tests to detect cardiac biomarkers including troponins, CK, and CK-MB, etc.

As used herein, "reperfusion" refers to the restoration of blood flow or supply to the heart or cardiac (e.g., myocardial) tissue that has become ischemic or hypoxic. Modalities for reperfusion include, but are not limited to, chemical dissolution of the occluding thrombus, i.e., thrombolysis, administration of vasodilators, angioplasty, percutaneous coronary intervention (PCI), catheterization and coronary artery bypass graft (CABG) surgery.

A "subject" or "individual" can be a vertebrate, a mammal, or a human. Mammals include, but are not limited to, farm animals, sport animals, pets, primates, mice and rats. In one aspect, a subject is a human.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

II. Compositions of the Invention

Provided herein are pharmaceutical compositions containing an epicardial-derived paracrine factor (e.g., FSTL1 such as hypoglycosylated FSTL1) and one or more pharmaceutically acceptable excipients or carriers.

In some embodiments, the epicardial-derived paracrine factor is follistatin-like protein 1 (FSTL1; also known as follistatin-related protein 1). FSTL1 is a protein that, in humans, is encoded by the FSTL1 gene. This gene encodes a protein with similarity to follistatin, which is an activin-binding protein. FSTL1 contains an FS module (a follistatin-like sequence containing 10 conserved cysteine residues), a Kazal-type serine protease inhibitor domain, 2 EF hand domains, and a Von Willebrand factor type C domain ("Entrez Gene: "FSTL1 follistatin-like 1) In other embodiments, FSTL1 comprises the amino acid sequence of SEQ ID NO:1 (NCBI Reference Sequence: NP_009016.1):

```
                                              (SEQ ID NO: 1)
MWKRWLALALALVAVAWVRAEEELRSKSKICANVFCGAGRECAVTEKGEP

TCLCIEQCKPHKRPVCGSNGKTYLNHCELHRDACLTGSKIQVDYDGHCKE

KKSVSPSASPVVCYQSNRDELRRRIIQWLEAEIIPDGWFSKGSNYSEILD

KYFKNFDNGDSRLDSSEFLKFVEQNETAINITTYPDQENNKLLRGLCVDA

LIELSDENADWKLSFQEFLKCLNPSFNPPEKKCALEDETYADGAETEVDC

NRCVCACGNWVCTAMTCDGKNQKGAQTQTEEEMTRYVQELQKHQETAEKT

KRVSTKEI
```

Nucleic acids encoding FSTL1 are provided and contemplated within the scope of the present invention. In various embodiments, the nucleic acid is a recombinant nucleic acid. In some embodiments, FSTL1 is encoded by the nucleic acid of SEQ ID NO:2 (NCBI Reference Sequence: NM_007085.4):

```
  1   aggagaatgg ggaggagctg gggggcagg caggcgggga aggagaggtc ttaaggggcg 61   gcgagggag gtcgcatttc ctccgaggct ggcgatcggc ggagctccca cctccgctta 121   cagctcgctg ccgccgtcct gccccgcgcc cccaggagac ctggaccaga ccacgatgtg 181   gaaacgctgg ctcgcgctcg cgctcgcgct ggtggcggtc gcctgggtcc gcgccgagga 241   agagctaagg agcaaatcca agatctgtgc caatgtgttt tgtggagccg gccgggaatg 301   tgcagtcaca gagaaagggg aacccacctg tctctgcatt gagcaatgca aacctcacaa 361   gaggcctgtg tgtggcagta atggcaagac ctacctcaac cactgtgaac tgcatcgaga 421   tgcctgcctc actggatcca aaatccaggt tgattacgat ggacactgca aagagaagaa 481   atccgtaagt ccatctgcca gcccagttgt ttgctatcag tccaaccgtg atgagctccg
```

-continued

```
541  acgtcgcatc atccagtggc tggaagctga gatcattcca
     gatggctggt tctctaaagg
601  cagcaactac agtgaaatcc tagacaagta ttttaagaac
     tttgataatg gtgattctcg
661  cctggactcc agtgaattcc tgaagtttgt ggaacagaat
     gaaactgcca tcaatattac
721  aacgtatcca gaccaggaga acaacaagtt gcttagggga
     ctctgtgttg atgctctcat
781  tgaactgtct gatgaaaatg ctgattggaa actcagcttc
     caagagtttc tcaagtgcct
841  caacccatct ttcaaccctc ctgagaagaa gtgtgccctg
     gaggatgaaa cgtatgcaga
901  tggagctgag accgaggtgg actgtaaccg ctgtgtctgt
     gcctgtggaa attgggtctg
961  tacagccatg acctgtgacg gaaagaatca gaaggggggcc
     cagacccaga cagaggagga
1021 gatgaccaga tatgtccagg agctccaaaa gcatcaggaa
     acagctgaaa agaccaagag
1081 agtgagcacc aaagagatct aatgaggagg cacagaccag
     tgtctggatc ccagcatctt
1141 ctccacttca gcgctgagtt cagtatacac aagtgtctgc
     tacagtcgcc aaatcaccag
1201 tatttgctta tatagcaatg agttttattt tgtttatttg
     ttttgcaata aaggatatga
1261 aggtggctgg ctaggaaggg aagggccaca gccttcattt
     ctaggagtgc tttaagagaa
1321 actgtaaatg gtgctctggg gctggaggct agtaaggaaa
     ctgcatcacg attgaaagag
1381 gaacagaccc aaatctgaac ctcttttgag tttactgcat
     ctgtcagcag gctgcaggga
1441 gtgcacacga tgccagagaa aacttagcag ggtgtccccg
     gaggagaggt ttgggaagct
1501 ccacggagag gaacgctctc tgcttccagc ctctttccat
     tgccgtcagc atgacagacc
1561 tccagcatcc acgcatctct tggtcccaat aactgcctct
     agatacatag ccatactgct
1621 agttaaccca gtgtccctca gacttggatg gagtttctgg
     gagggtacac ccaaatgatg
1681 cagatacttg tatactttga gccccttagc gacctaacca
     aattttaaaa atactttta
1741 ccaaaggtgc tatttctctg taaaacactt ttttttggca
     agttgacttt attcttcaat
1801 tattatcatt atattattgt tttttaatat tttatttct
     tgactaggta ttaagctttt
1861 gtaattattt ttcagtagtc ccaccacttc ataggtggaa
     ggagtttggg gttcttcctg
1921 gtgcaggggc tgaaataacc cagatgcccc caccctgcca
     catactagat gcagcccata
1981 gttggccccc ctagcttcca gcagtccact atctgccaga
     ggagcaaggg tgccttagac
2041 cgaagccagg ggaagaagca tcttcataaa aaactttcaa
     gatccaaaca ttaatttgtt
2101 tttatttatt ctgagaagtt gaggcaaatc agtattccca
     aggatggcga caagggcagc
2161 caagcagggc ttaggatatc ccagcctacc aatatgctca
     ttcgactaac taggagggtg
2221 agttggcccc gtctcttctt ttttctggac ctcagttcc
     tcagtgagct ggtaagaatg
2281 cactaacctt ttgatttgat aagttataaa ttctgtggtt
     ctgatcattg gtccagaggg
2341 gagataggtt cctgtgattt ttccttcttc tctatagaat
     aaatgaaatc ttgttactag
2401 aacaagaaat gtcagatggc caaaaacaag atgaccagat
     ttgatctcag cctgatgacc
2461 ctacaggtcg tgctatgata tggagtcctc atgggtaaag
     caggaagaga gtgggaaaga
2521 gaaccacccc actctgtctt catatttgca tttcatgttt
     aacctccggc tggaaataga
2581 aagcattccc ttagagatga ggataaaaga aagtttcaga
     ttcaacaggg ggaagaaaat
2641 ggagatttaa tcctaaaact gtgacttggg gaggtcagtc
     atttacagtt agtcctgtgt
2701 ctttcgactt ctgtgattat taaccccact cactaccctg
     tttcagatgc atttggaata
2761 ccaaagatta aatccttgac ataagatctc atttgcagaa
     agcagattaa agaccatcag
2821 aaggaaatta tttaggttgt aatgcacagg caactgtgag
     aaactgttgt gccaaaaata
2881 gaattccttc tagttttct tgttctcatt tgaaaggaga
     aaattccact ttgtttagca
```

```
2941  tttcaagctt ttatgtatcc atcccatcta aaaactcttc
      aaactccact tgttcagtct 3001  gaaatgcagc tccctgtcca agtgccttgg agaactcaca
      gcagcacgcc ttaatcaaag 3061  gttttaccag cccttggaca ctatgggagg agggcaagag
      tacaccaatt tgttaaaagc 3121  aagaaaccac agtgtctctt cactagtcat ttagaacatg
      gttatcatcc aagactactc 3181  taccctgcaa cattgaactc ccaagagcaa atccacattc
      ctcttgagtt ctgcagcttc 3241  tgtgtaaata gggcagctgt cgtctatgcc gtagaatcac
      atgatctgag gaccattcat 3301  ggaagctgct aaatagccta gtctgggag tcttccataa
      agttttgcat ggagcaaaca 3361  aacaggatta aactaggttt ggttccttca gccctctaaa
      agcatagggc ttagcctgca 3421  ggcttccttg ggctttctct gtgtgtgtag ttttgtaaac
      actatagcat ctgttaagat 3481  ccagtgtcca tggaaacatt cccacatgcc gtgactctgg
      actatatcag tttttggaaa 3541  gcaggtcc tctgcctgct aacaagccca cgtggaccag
      tctgaatgtc tttcctttac 3601  acctatgttt ttaagtagtc aaacttcaag aaacaatcta
      aacaagtttc tgttgcatat 3661  gtgtttgtga acttgtattt gtatttagta ggcttctata
      ttgcatttaa cttgtttttg 3721  taactcctga ttcttccttt tcggatacta ttgatgaata
      aagaaattaa agtgatggtt 3781  ttggttt cctttccccc aattaaggcc aaataaagtc
      gtgagaacat tacccattta
```

An FSTL1 nucleic acid can be incorporated into a vector, such as an expression vector, using standard techniques known to one of skill in the art. Methods used to ligate the DNA construct comprising a nucleic acid of interest such as FSTL1, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express FSTL1 nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., *Molecular Cloning: A Laboratory Manual*, 2nd ed., Cold Spring Harbor, 2001.

A variety of host cells can be used to make a recombinant host cell that can express FSTL1. The host cell may be a cell that naturally produces FSTL1 or a cell that does not naturally produce FSTL1. For example, mammalian cells, such as, but not limited to, Chinese Hamster Ovary (CHO) cells or epicardium-derived cell cultures can be used to produce FSTL1. However, in other embodiments, cells derived from organisms that do not glycosylate proteins following translation (i.e. cells which do not post-translationally modify proteins with one or more carbohydrate moieties) are used to produce recombinant Fstl.

Non-limiting examples of cells that do not glycosylate proteins following translation include bacterial cells. As such, in one embodiment, the host cell is a bacterial cell. In another embodiment, the bacterial cell is a gram-positive bacterial cell or gram-negative bacterial cell. In another embodiment, the bacterial cell is selected from the group consisting of *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cells.

FSTL1-encoding nucleic acids or vectors containing them can be inserted into a host cell (e.g., a bacterial cell) using standard techniques for expression of the encoded FSTL1 polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are well known in the art (see, e.g., *Current Protocols in Molecular Biology* (F. M. Ausubel et al. (eds) Chapter 9, 1987; Sambrook et al., *Molecular Cloning: A Laboratory Manual*, 3rd ed., Cold Spring Harbor, 2001; and Campbell et al., *Curr Genet*, 16:53-56, 1989, which are each hereby incorporated by reference in their entireties, particularly with respect to transformation methods). The introduced nucleic acids may be integrated into chromosomal DNA of the host cell or maintained as extrachromosomal replicating sequences. In yet another embodiment, an FSTL1 polypeptide can be produced in a host cell via delivery of chemically modified mRNAs encoding the mutated Fstl1 glycosylation-deficient polypeptide. (see *Modified mRNA directs the fate of heart progenitor cells and induces vascular regeneration after myocardial infarction*. Zangi L, et al. *Nat Biotechnol*. 2013 October; 31(10):898-907, incorporated herein by reference in its entirety). Chemically modified RNAs, also referred to herein as modRNAs, may include, for example, modifications of phosphate into phosphorothioate internucleotidic linkages, modifications of the 2'-hydroxyl group of ribose, or other modifications to the phosphate backbone or sugar moieties of snRNA.

In some embodiments, FSTL1 is a hypoglycosylated FSTL1. Hypoglycosylated FSTL1 can be obtained by producing recombinant FSTL1 in host cells that naturally do not post-translationally modify proteins with carbohydrate moieties (such as bacteria, e.g. *E. coli*) or which have been engineered such that they are unable to post-translationally modify proteins with carbohydrate moieties. Alternatively, hypoglycosylated FSTL1 can be produced in mammalian or other eukaryotic cells that normally post-translationally modify proteins with carbohydrate moieties but which have been treated with one or more glycosylation inhibitors. Suitable glycosylation inhibitors include, without limitation, tunicamycin (which blocks all N-glycosylation of proteins), streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, a glucose analog, a mannose analog, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, a hydroxymethylglutaryl-CoA reductase inhibitor, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl-2-deoxyglucose, N-Acetyl-D-Glucosamine, hygoxanthine, thymidine, cholesterol, glucosamine, mannosamine, castanospermine, glutamine, bromoconduritol, conduritol epoxide, a conduritol derivative, aglycosylmethyl-p-nitrophenyltriazene, β-Hydroxynorvaline, threo-β-fluoroasparagine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, 2-deoxy-D-glucose, and fluoroacetate.

Alternatively, in other embodiments, recombinant FSTL1 is engineered such that it is unable to be glycosylated when produced using a eukaryotic or other glycosylation-competent host cell. In most biological contexts, glycosylation is either N-linked or O-linked. The N-linked glycosylation process occurs in eukaryotes and widely in archaea, but very rarely in eubacteria. In N-linked glycosylation, glycans (i.e. carbohydrate-containing moieties) are attached to the nitrogen atom of an asparagine or arginine amino acid side-chain. N-linked glycans are almost always attached to the nitrogen atom of an asparagine (Asn) side chain that is present as a part of Asn-X-Ser/Thr consensus sequence, where X is any amino acid except proline (Pro), serine (Ser), and threonine (Thr). O-linked glycosylation is a form of glycosylation that occurs in the Golgi apparatus in eukaryotes. In O-linked glycosylation, glycans are attached to the hydroxyl oxygen of serine, threonine, tyrosine, hydroxylysine, or hydroxyproline amino acid side-chains.

Consequently, in some embodiments, recombinant FSTL1 is engineered so that it is unable to be N-linked glycosylated. In this instance, some or all glycosylation-competent arginine or asparagine amino acids in the polypeptide sequence can be substituted with a glycosylation-incompetent amino acid (for example, glutamine). In other embodiments, recombinant FSTL1 is engineered so that it is unable to be O-linked glycosylated. In this instance, all glycosylation-competent serine, threonine, tyrosine, hydroxylysine, or hydroxyproline residues in the polypeptide sequence can be substituted with a glycosylation-incompetent amino acid (for example, alanine). In yet further embodiments, recombinant FSTL1 is engineered so that it is unable to be either O-linked glycosylated or N-linked glycosylated by substituting all glycosylation-competent amino acids with glycosylation-incompetent amino acids. In a further embodiment, one or more asparagine (N) residues located at positions X144, X180, X175, and/or X223 in the FSTL1 amino acid sequence are substituted with a glycosylation-incompetent amino acid (such as, but not limited to, glutamine (Q)). Engineered glycosylation-incompetent FSTL1 can be produced in host cells via transfection of a plasmid, viral vector carrying a gene encoding a glycosylation-incompetent FSTL1 or chemically synthetized mRNA or mRNA-mimetics. Alternatively, a gene encoding a glycosylation-incompetent FSTL1 can be integrated into a chromosome of the host cell under the control of an inducible or constitutively-expressing promoter. In yet another embodiment, a glycosylation incompetent FSTL1 polypeptide can be produced in a host cell via delivery of modified mRNAs encoding a glycosylation incompetent FSTL1 polypeptide.

The presently described invention contemplates FSTL1 incorporated into a pharmaceutical composition (e.g., a sterile pharmaceutical composition) containing one or more pharmaceutically acceptable carriers. As used herein, a "pharmaceutically acceptable carrier" or a "pharmaceutically acceptable excipient" according to the present invention is a component such as a carrier, diluent, or excipient of a composition that is compatible with the other ingredients of the composition in that it can be combined with the agents and/or compositions of the present invention without eliminating the biological activity of the agents or the compositions (for example, FSTL1, such as hypoglycosylated FSTL1), and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, sterile water, polyethylene glycol, polyvinyl pyrrolidone, lecithin, arachis oil, sesame oil, emulsions such as oil/water emulsions or water/oil emulsions, microemulsions, nanocarriers and various types of wetting agents. Additives such as water, alcohols, oils, glycols, preservatives, flavoring agents, coloring agents, suspending agents, and the like may also be included in the composition along with the carrier, diluent, or excipient. In one embodiment, a pharmaceutically acceptable carrier appropriate for use in the compositions disclosed herein is sterile, pathogen free, and/or otherwise safe for administration to a subject without risk of associated infection and other undue adverse side effects.

Any of the FSTL1-containing (such as hypoglycosylated FSTL1-containing) pharmaceutical compositions disclosed herein can be formulated for administration using any number of administrative methods available in the art. Administration can be by a variety of routes including patch, catheter, stent, oral, rectal, transdermal, subcutaneous, intravenous, intramuscular, intranasal, and the like. In some embodiments, the above methods of administration can be used for delivery of suspensions comprising FSTL1 (e.g., hypoglycosylated FSTL1 mixed with gelfoam particles.) These compositions are effective as both injectable and oral compositions. Such compositions are prepared in a manner well known in the pharmaceutical art and comprise at least one active compound. When employed as oral compositions, the polypeptide compositions are protected from acid digestion in the stomach by a pharmaceutically acceptable protectant.

In some embodiments, any of the FSTL1-containing (such as hypoglycosylated FSTL1-containing) pharmaceutical compositions disclosed herein can be incorporated into an engineered patch for administration directly to the epicardium or damaged tissue of the myocardium. In one embodiment, a compressed collagen gel is used to produce a three dimensional (3D) collagen patch to deliver hypoglycosylated FSTL1 directly to the epicardium. In some embodiments, highly hydrated collagen gels can be compressed in order to remove excess water and produce a dense biomaterial with improved biological and mechanical properties.

As described in Example 2 infra, highly hydrated collagen gels underwent unconfined compression via application of a static compressive stress of ~1,400 Pa for 5 minutes resulting in ~98-99% volume reduction. The elastic modulus of the compressed collagen approximates that of the embryonic epicardium which is optimal for contractility of immature cardiomyocytes. Elasticity of compressed collagen patches can be assessed by atomic force microscopy (AFM) in nano-indentation mode, using a force trigger resulting in a minimal local strain of less than about 10% (such as less than any of about 9%, 8%, 7%, 6%, 5%, 4%, 3%, 2% 1%, or 0.5%, inclusive of all values falling between these percentages) and having an indentation of ~100 nm to minimize the effect of substrate-related artifacts. The 3D collagen patches can be seeded with recombinantly-produced FSTL1 (such as hypoglycosylated FSTL1) followed by direct administration to the epicardium or to a damaged or injured area of the myocardium by, for example, suturing. In some embodiments, the 3D collagen patches have an elastic modulus comparable to that reported for the embryonic epicardium (E~12±4 kPa, such as any of about 8 kDa, 9 kDa, 10 kDa, 11 kDa, 12 kDa, 13 kDa, 14 kDa, 15 kDa, or 16 kDa). In other embodiments, the 3D collagen patches have an elastic modulus which is lower than those of mature epicardium (E>30-40 kPa). In other embodiments, the 3D collagen patches have an elastic modulus which is lower than those of fibrotic cardiac tissue (E>100 kPa), but higher than those for most of the currently used scaffolding biomaterials (E≤1 kPa). In another embodiment, the he 3D collagen patches have an elastic modulus of about any of 1 kPa, 2 kPa, 3 kPa, 4 kPa, 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 27 kPa, 28 kPa, or 29 kPa.

Further information related to constructing and using 3D collagen-based patches for delivery of substances directly to the heart can be found in Serpooshan, V. et al., *Acta Biomater*, 2010; 6, 3978-3987; Serpooshan, V. et al., *J Biomed Mater Res A*, 2011; 96, 609-620; and Abou Neel et al., *Soft Matter*, 2006; 2, 986-992, the disclosures of which are incorporated by reference herein.

Another option for the delivery of a hypoglycosylated FSTL1 polypeptide to cardiac tissue is as a component of a self-polymerizing hydrogel delivered by catheter technology. Further information related to this type of delivery can be found in Koudstaal et al., *J of Cardiovasc. Trans. Res.* (2014) 7:232-241, the disclosure of which is incorporated by reference herein. Catheter delivery may also be employed for suspensions comprising FSTL1 (e.g., hypoglycosylated FSTL1 mixed with gelfoam particles.)

III. Methods of the Invention

Provided herein are methods for repairing cardiac (e.g., myocardial) tissue following an injury in a subject in need thereof, the method comprising contacting the cardiac (e.g., myocardial) tissue with an epicardial-derived paracrine factor. In some embodiments, the epicardial-derived paracrine factor is a hypoglycosylated follistatin-like 1 (FSTL1) polypeptide. In other embodiments of the present invention, administration of hypoglycosylated FSTL1 does not activate Akt-1 signaling activity (see FIG. 20). In other embodiments of the present invention, administration of hypoglycosylated FSTL1 does not result in decreased apoptosis of cardiomyocytes (see FIG. 6).

The injury to the cardiac (e.g., myocardial) tissue can be associated with any number of diseases or conditions known to affect the heart or circulatory system and include, without limitation, coronary heart disease, cardiomyopathy, ischemic heart disease, heart failure, inflammatory heart disease, valvular heart disease and aneurysm. In one embodiment, the injury is caused by myocardial infarction (MI; such as acute myocardial infarction (AMI)). In another embodiment, the injury is caused by an ischemic event followed by reperfusion.

Repair of injured cardiac (e.g., myocardial) tissue can comprise increasing the number of cardiomyocytes that can be indirectly measure in the live subject by several methods of imaging (like delayed enhance MRI, DE-MRI) as decreased in myocardial infarct size. See for example: (Hendel R C et al, JACC 48(7); 1475-97) and (Sardella G et al, JACC 2009; 53(4):309-15, incorporated herein by reference in its entirety). In some embodiments, contacting the cardiac (e.g., myocardial) tissue with an epicardial-derived paracrine factor (such as hypoglycosylated FSTL1) results in any of about a 2%, 5%, 10%, 15%, 20%, 30%, 40% 50%, 60%, 90%, 100%, or about a 5-10%, 10-20%, 20-30%, 30-40%, 40-50%, 50-60%, 60-70%, 70-80%, 80-90%, 90-100% recovery of lost muscle and reduction of infarct size. In other embodiments, contacting the cardiac (e.g., myocardial) tissue with an epicardial-derived paracrine factor (such as hypoglycosylated FSTL1) results in any of about at least 2%, 5%, 10%, 15%, 20%, 30%, 40% 50%, 60%, 90%, 100%, or about a 5-10%, 10-20%, 20-30%, 30-40%, 40-50%, 50-60%, 60-70%, 70-80%, 80-90%, 90-100% recovery of lost muscle and reduction of infarct size. In other embodiments, contacting the cardiac (e.g., myocardial) tissue with an epicardial-derived paracrine factor (such as hypoglycosylated FSTL1) results in any of about at most 2%, 5%, 10%, 15%, 20%, 30%, 40% 50%, 60%, 90%, 100%, or about a 5-10%, 10-20%, 20-30%, 30-40%, 40-50%, 50-60%, 60-70%, 70-80%, 80-90%, 90-100% recovery of lost muscle and reduction of infarct size.

In some embodiments of any of the methods disclosed herein, the epicardial-derived paracrine factor (such as hypoglycosylated FSTL1) is infused, seeded, or embedded into a 3D collagen based-patch (such as any of those described herein). The collagen based patch can then be contacted directly to the epicardium or an injured area of myocardium (such as an area of the myocardium exposed to an ischemic event, such as myocardial infarction). The 3D collagen patch may be applied to the epicardium or myocardium via suturing or by any other means known in the art for contacting the patch to the injured tissue.

In yet other embodiments, the epicardial-derived paracrine factor (such as hypoglycosylated FSTL1) is a component of a hydrogel that is delivered to the epicardium, to the endocardium, or to an injured area of myocardium (by, for example, catheter technology; Koudstaal et al., *J. of Cardiovasc. Trans. Res.* (2014) 7:232-241, incorporated herein by reference in its entirety).

In some embodiments of any of the methods disclosed herein, about 1, 2, 3, 4, 5, 6, 7, 8, 9, 10, 20, 30, 40, 50, 60, 70, 80, 90, 100, or more fold increase in the number of cardiomyocytes is achieved compared to the number of cardiomyocytes in cardiac (e.g., myocardial) tissue that is not contacted by an epicardial-derived paracrine factor following an injury. Assessment of cardiomyocyte replication is routine in the art and can be measured by, for example, by determining the number of α-actinin positive cells in a cardiac (e.g., myocardial) tissue sample from a subject. In some other embodiments, the effect on the cardiac (e.g., myocardial) tissue could be achieved with placement of hypoglycosylated FSTL1 in proximity to the endocardial compartment (i.e. the endocardium), for example, by delivery via catheter technology. In some embodiments a suitable catheter may be a NOGA catheter (Johnson & Johnson).

In some embodiments, the effect on the cardiac (e.g., myocardial) tissue can be achieved with placement of hypoglycosylated FSTL1 endocardially into the heart by percutaneous catheter delivery systems, for example as the systems available developed by BioCardia (www.biocardia.com).

In some embodiments, the effect on the cardiac (e.g., myocardial) tissue can be achieved with placement of hypoglycosylated FSTL1 epicardially into the heart using catheter devices similar to those used in other applications (for example Epicardial Catheter System™, St. Jude Medical).

In some embodiments, the effect on the cardiac (e.g., myocardial) tissue can be achieved with placement of hypoglycosylated FSTL1 when impregnated in drug-diluting stents (for example, those available from Abbott Laboratories or Biosensors International, among others).

In some embodiments, the effect on the cardiac (e.g., myocardial) tissue can be achieved with placement of hypoglycosylated FSTL1 systemically, using approved formulation.

In some embodiments, the effect on the cardiac (e.g., myocardial) tissue can be achieved with placement of hypoglycosylated FSTL1 can be achieved by the use of compound or drugs that inhibit the glycosylation of the endogenous glycosylated FSTL1 protein, which is readily available and known to one of skill in the art.

In some embodiments, the effect on the cardiac (e.g., myocardial) tissue can be achieved with placement of hypoglycosylated FSTL1 can be achieved by introduction of modRNAs encoding for specific mutagenesis targeting N-glycosylation sites in the FSTL1 mRNA sequence.

In some embodiments, the effect on the cardiac (e.g., myocardial) tissue can be achieved with placement of hypoglycosylated FSTL1 can be achieved by genome editing using CRISPR/Cas9 technology or similar, (see for example Genome editing with Cas9 in adult mice corrects a disease mutation and phenotype. Hao Yin, et al. *Nature Biotechnology* 32, 551-553 (2014) doi:10.1038/nbt.2884, incorporated by reference herein in its entirety.)

In some other embodiments, the effect on the cardiac (e.g., myocardial) tissue can be achieved with delivery of small molecule mimetic of hypoglycosylated FSTL1

In other embodiments, repair of injured cardiac (e.g., myocardial) tissue includes an improvement in the percent fractional shortening of cardiac (e.g., myocardial) tissue compared to the amount of percent fractional shortening in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated Fstl1) results in any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% or greater improvement in percent fractional shortening of cardiac (e.g., myocardial) tissue compared to same subject prior treatment, inclusive of all values falling in between these percentages. In some embodiments, contacting the cardiac (e.g., myocardial) tissue with an epicardial-derived paracrine factor (such as hypoglycosylated Fstl1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% improvement in percent fractional shortening of cardiac (e.g., myocardial) tissue compared to same subject prior treatment, inclusive of all values falling in between these percentages. In some embodiments, contacting the cardiac (e.g., myocardial) tissue with an epicardial-derived paracrine factor (such as hypoglycosylated Fstl1) results in any of about at least 1-100%, 5-95%, 10-90%, 20-80%, 30-70%, 5-10%, 10-20%, 20-30%, 30-40%, 40-50%, 50-60%, 60-70%, 70-80%, 80-90%, 90-100% improvement in percent fractional shortening of cardiac (e.g., myocardial) tissue compared to same subject prior treatment, inclusive of all values falling in between these percentages. In some embodiments, contacting the cardiac (e.g., myocardial) tissue with an epicardial-derived paracrine factor (such as hypoglycosylated Fstl1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, 90-100% improvement in percent fractional shortening of cardiac (e.g., myocardial) tissue compared to same subject prior treatment, inclusive of all values falling in between these percentages. Repair of injured cardiac (e.g., myocardial) tissue can also comprise an increase in the amount of cardiomyocyte cytokinesis compared to the amount of cardiomyocyte cytokinesis in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% or greater improvement the amount of cardiomyocyte cytokinesis. In some embodiments, contacting the cardiac (e.g., myocardial) tissue with an epicardial-derived paracrine factor (such as hypoglycosylated FSTL1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% or greater improvement the amount of cardiomyocyte cytokinesis. In some embodiments, contacting the cardiac (e.g., myocardial) tissue with an epicardial-derived paracrine factor (such as hypoglycosylated FSTL1) results in any of about at least 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% improvement the amount of cardiomyocyte cytokinesis. In some embodiments, contacting the cardiac (e.g., myocardial) tissue with an epicardial-derived paracrine factor (such as hypoglycosylated FSTL1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% improvement the amount of cardiomyocyte cytokinesis. Assessment of cardiomyocyte cytokinesis is routine in the art and can be measured by, for example, determining the expression level of Aurora B kinase in a cardiac (e.g., myocardial) tissue sample from a subject. Current methods allow these studies to be performed only post-mortem or after biopsy or after transplantation.

In some embodiments, repair of injured cardiac (e.g., myocardial) tissue can comprise decreased cardiomyocyte apoptosis compared to the amount cardiomyocyte apoptosis in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about a at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100% or greater reduction in cardiomyocyte apoptosis in cardiac (e.g., myocardial) tissue, inclusive of all values falling in between these percentages. In some embodiments, contacting the cardiac (e.g., myocardial) tissue with an epicardial-derived paracrine factor (such as hypoglycosylated FSTL1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% reduction in cardiomyocyte apoptosis in cardiac (e.g., myocardial) tissue, inclusive of all values falling in between these percentages. In some embodiments, contacting the cardiac (e.g., myocardial) tissue with an epicardial-derived paracrine factor (such as hypoglycosylated FSTL1) results in any of about a at least 1-100%, 5-95%, 10-90%, 20-80%, 30-70%, 5-10%, 10-20%, 20-30%, 30-40%, 40-50%, 50-60%, 60-70%, 70-80%, 80-90%, 90-100% or greater reduction in cardiomyocyte apoptosis in cardiac (e.g., myocardial) tissue, inclusive of all values falling in between these percentages. In some embodiments, contacting the cardiac (e.g., myocardial) tissue with an epicardial-derived paracrine factor (such as hypoglycosylated FSTL1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% reduction in cardiomyocyte apoptosis in cardiac (e.g., myocardial) tissue, inclusive of all values falling in between these percentages. Assessment of cardiomyocyte apoptosis is routine (post-mortem or ex-vivo, after heart separation) in the art and can be measured by, for example, TUNEL staining of a cardiac (e.g., myocardial) tissue sample from a subject.

Repair of injured cardiac (e.g., myocardial) tissue can also comprise increased levels of one or more transcripts encoding cardiac-specific contractile proteins in cardiomyocytes compared to the transcriptional level of these contractile proteins in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated Fstl1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100% or greater increased level of one or more transcripts encoding cardiac-specific contractile proteins. In some embodiments, contacting the cardiac (e.g., myocardial) tissue with an epicardial-derived paracrine factor (such as hypoglycosylated Fstl1) results in any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% increased level of one or more transcripts encoding cardiac-specific contractile proteins. In some embodiments, contacting the cardiac (e.g., myocardial) tissue with an epicardial-derived paracrine factor (such as hypoglycosylated Fstl1) results in any of about at least 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% increased level of one or more transcripts encoding cardiac-specific contractile proteins. In some embodiments, contacting the cardiac (e.g., myocardial) tissue with an epicardial-derived paracrine factor (such as hypoglycosylated Fstl1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% increased level of one or more transcripts encoding cardiac-specific contractile proteins. In some embodiments, the cardiac-specific contractile proteins are selected from the group consisting of myh6, mlc2v, and mlc2a. Assessment of cardiac-specific contractile protein transcript is routine in the art and can be measured by, for example, Northern blot, Western blot, reverse transcriptase (RT) PCR, FACS analysis, immunohistochemistry, or in situ hybridization.

Repair of injured cardiac (e.g., myocardial) tissue can comprise increased actinin$^+$ cells with rhythmic contractile Ca$^{2+}$ in cardiomyocytes. In some embodiments, contacting the cardiac (e.g., myocardial) tissue with an epicardial-derived paracrine factor (such as hypoglycosylated Fstl1) results in any of about 1, 2, 3, 4, 5, 6, 7, 8, 9, 10, 20, 30, 40, 50, 60, 70, 80, 90, 100, or more fold increase in the amount of actinin$^+$ cells with rhythmic contractile Ca$^{2+}$ in cardiomyocytes compared to the number of actinin$^+$ cells with rhythmic contractile Ca$^{2+}$ in cardiac (e.g., myocardial) tissue that is not contacted by an epicardial-derived paracrine factor following an injury. Assessment of actinin$^+$ cells with rhythmic contractile Ca$^{2+}$ in cardiomyocytes is routine in the art (See Example 1, infra).

The injured cardiac (e.g., myocardial) tissue can be contacted with any of the epicardial-derived paracrine factor (such as hypoglycosylated FSTL1) compositions (such as pharmaceutical compositions) disclosed herein before, during, or subsequent to the injury to the cardiac (e.g., myocardial) tissue. In some embodiments, the cardiac (e.g., myocardial) tissue is contacted with the epicardial-derived paracrine factor composition in a subject deemed at risk for cardiovascular disease, MI, or another myocardial ischemic event in order to mitigate or prevent injury to the myocardium by the event. In other embodiments, the cardiac (e.g., myocardial) tissue is contacted with the epicardial-derived paracrine factor composition immediately following the onset of an ischemic event caused by cardiovascular disease or MI, such as about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 45 minutes, 1 hour, 1.5 hours, 2 hours, 2.5 hours, 3 hours, 3.5 hours, 4 hours, 4.5 hours, 5 hours 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, or 12 hours or more (inclusive of all time periods falling in between these values). In some embodiments, the composition is administered less than 1 minute after the cardiac injury. Alternatively, in other embodiments, the cardiac (e.g., myocardial) tissue is contacted with the epicardial-derived paracrine factor composition subsequent to the injury, such as at least 12 hours, 13 hours, 14 hours, 15 hours, 16 hours, 17 hours, 18 hours, 19 hours, 20 hours, 21 hours, 22 hours, 23 hours, 24 hours or 1 day, 2 days, 3 days, 4 days, 5 days, 6 days, 7 days, 8 days, 9 days, 10 days, 11 days, 12 days, 13 days, 14 days, three weeks, one month, 2 months, 3 months, 4 months, 6 months, 7 months, 8 months, 9 months, 10 months, 11 months, or one or more years (inclusive of all time periods falling in between these values) following the onset of an ischemic event caused by cardiovascular disease or MI.

Any of the methods of treating injuries to cardiac (e.g., myocardial) tissue disclosed herein can result in increased survival in a subject following injury. As used herein, increased survival includes, e.g., at least about a 5% (e.g., at least about 10%, 15%, 20%, 25%, 30%, 40%, 45%, 50%, 60%, 70%, 80%, 90%, 100%, 110%, 120%, 130%, 140%, 150% or more than 200% or greater) increase in the survival of a subject compared to relative survival in subjects who have not been subject to the instantly described methods. Survival time can be measured, e.g., in days, weeks, months, or years. In some embodiments, contacting injured cardiac (e.g., myocardial) tissue with an epicardial-derived paracrine factor in accordance with any of the methods described herein can prolong the survival of subject by at least six months, seven months, eight months, nine months, 10 months, 12 months, 18 months, 24 months, 36 months, or more.

In some embodiments, repair of injured cardiac (e.g., myocardial) tissue can comprise decreased or attenuated fibrosis in cardiac (e.g., myocardial) tissue compared to the amount of fibrosis in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or greater reduction in fibrosis in cardiac (e.g., myocardial) tissue, inclusive of all values falling in between these percentages. In some embodiments, contacting the cardiac (e.g., myocardial) tissue with an epicardial-derived paracrine factor (such as hypoglycosylated FSTL1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% reduction in fibrosis in cardiac (e.g., myocardial) tissue, inclusive of all values falling in between these percentages. In some embodiments, contacting the cardiac (e.g., myocardial) tissue with an epicardial-derived paracrine factor (such as hypoglycosylated FSTL1) results in any of about at least 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% reduction in fibrosis in cardiac (e.g., myocardial) tissue, inclusive of all values falling in between these percentages. Assessment of cardiomyocyte fibrosis is routine in the art and can be measured by DE-MRI, or by histologic examination of cardiac (e.g., myocardial) tissue (post-mortem, or biopsy). In some embodiments, contacting the cardiac (e.g., myocardial) tissue with an epicardial-derived paracrine factor (such as hypoglycosylated FSTL1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% reduction in fibrosis in cardiac (e.g., myocardial) tissue, inclusive of all values falling in between these percentages. Assessment of cardiomyocyte fibrosis is routine in the art and can be measured by DE-MRI, or by histologic examination of cardiac (e.g., myocardial) tissue (post-mortem, or biopsy).

Repair of injured cardiac (e.g., myocardial) tissue can additionally comprise increased vascularization of the injured region of the cardiac (e.g., myocardial) tissue. In some embodiments, contacting the cardiac (e.g., myocardial) tissue with an epicardial-derived paracrine factor (such as hypoglycosylated FSTL1) results in any of about at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or greater recovery or blood-perfused increase in the amount of vascularization in cardiac (e.g., myocardial) tissue compared to the relative amount of vascularization in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about at most 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% recovery or blood-perfused increase in the amount of vascularization in cardiac (e.g., myocardial) tissue compared to the relative amount of vascularization in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about at least 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% recovery or blood-perfused increase in the amount of vascularization in cardiac (e.g., myocardial) tissue compared to the relative amount of vascularization in cardiac (e.g., myocardial) tissue that is not contacted by an epicardial-derived paracrine factor following an injury. In some embodiments, contacting the cardiac (e.g., myocardial) tissue with an epicardial-derived paracrine factor (such as hypoglycosylated FSTL1) results in any of about at most 1-100%, 5-95%, 10-90%, 20-80%, 30-70%, 5-10%, 10-20%, 20-30%, 30-40%, 40-50%, 50-60%, 60-70%, 70-80%, 80-90%, or 90-100% recovery or blood-perfused increase in the amount of vascularization in cardiac (e.g., myocardial) tissue compared to the relative amount of vascularization in cardiac (e.g., myocardial) tissue that is not contacted by an epicardial-derived paracrine factor following an injury. Assessment of vascularization in cardiac (e.g., myocardial) tissue is routine in the art and may be assessed by measuring the expression of proteins such as von Willebrand factor (vWF) or smooth muscle actin in blood vessel cells (See Example 4, infra).

In further embodiments, repair of injured cardiac (e.g., myocardial) tissue encompasses increased cardiomyocyte cell cycle entry. In some embodiments, contacting the cardiac (e.g., myocardial) tissue with an epicardial-derived paracrine factor (such as hypoglycosylated Fstl1) results in any of at least about 1, 2, 3, 4, 5, 6, 7, 8, 9, 10, 20, 30, 40, 50, 60, 70, 80, 90, 100, or more fold increase in the amount of cardiomyocyte cell cycle entry in cardiac (e.g., myocardial) tissue compared to the amount of cardiomyocyte cell cycle entry in cardiac (e.g., myocardial) tissue that is not contacted by an epicardial-derived paracrine factor following an injury. Assessment of cardiomyocyte cell cycle entry in cardiac (e.g., myocardial) tissue is routine in the art and may be assessed by measuring the expression of, for example, phosphor-Histone H3 (See Example 5, infra).

In some embodiments of any of the methods disclosed herein, the epicardial-derived paracrine factor (such as hypoglycosylated Fstl1) is infused, seeded, or embedded into a 3D collagen based-patch (such as any of those described herein). The collagen based patch can then be contacted directly to the epicardium or an injured area of myocardium (such as an area of the myocardium exposed to an ischemic event, such as myocardial infarction). The 3D collagen patch may be applied to the epicardium or myocardium via suturing or by any other means known in the art for contacting the patch to the injured tissue.

In yet other embodiments, the epicardial-derived paracrine factor (such as hypoglycosylated Fstl1) is a component of a hydrogel that is delivered to the epicardium, to the endocardium, or to an injured area of myocardium (by, for example, catheter technology; Koudstaal et al., *J. of Cardiovasc. Trans. Res.* (2014) 7:232-241).

IV. Kits

Also provided herein are kits comprising (i) an epicardial-derived paracrine factor (such as a hypoglycosylated FSTL1 polypeptide); and (ii) one or more pharmaceutically acceptable excipients. One or both of these kit components can be made to be sterile so that it can be administered to an individual in need (e.g., an individual with cardiac injury, such as MI). The kits may optionally contain a 3D collagen patch (such as any of these disclosed herein) that can be seeded or infused with the epicardial-derived paracrine factor prior to administration to a subject. Alternatively, a pre-seeded or pre-infused 3D collagen patch may be included in the kit along with written instructions regarding its use and application to injured cardiac (e.g., myocardial) tissue or the epicardium of a subject in need thereof. The kit may further comprise means for adhering the 3D collagen patch to the epicardium or to injured cardiac (e.g., myocardial) tissue such as, without limitation, suturing material.

Any of the kits disclosed herein can also include a hydrogel (such as a self-polymerizing hydrogel) as a carrier for an epicardial-derived paracrine factor (such as a hypoglycosylated FSTL1 polypeptide). In one embodiment, the kits also include one or more catheters for delivery of the hydrogel (such as a hydrogel infused with a hypoglycosylated FSTL1 polypeptide) to the endocardium, epicardium, and/or one or more damaged areas of the myocardium.

The kit can also include written instructions for using the kit, such as instructions for infusing an epicardial-derived paracrine factor into a 3D collagen patch, suturing the patch to the myocardium or epicardium, infusing an epicardial-derived paracrine factor into a hydrogel (such as a self-polymerizing hydrogel) as well as delivery of the hydrogel to the epicardium or one or more damaged areas of the myocardium via catheter technology.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

Example 1: Epicardial Paracrine Signaling Activates Cardiomyocyte Amplification The epicardium of the heart is an external epithelial layer that contributes to myocardial growth during development by providing progenitor cells[1,2] as well as mitogens, including FGFs, IGF2, and PDGFs[3-5]. Recent studies suggest that the epicardium might also preserve function of the adult myocardium following injury, possibly as a source of myogenic progenitors[6,7]. However, no epicardial-derived paracrine factors have been shown to support myocardial regeneration in mammals, although their identity and mechanism of action would provide insight into this poorly understood and inherently inefficient process[8]. This example describes the identification of such an epicardial-derived paracrine factor.

Materials and Methods

Progenitor Cells

Sca1$^+$, Myh6$^-$ cardiomyocyte progenitors were obtained by the Schneider laboratory as described[19].

Epicardial Mesothelial Cells (EMCs) were maintained in DMEM with 10% FBS and antibiotics/antimycotic as described[33]. EMCs are stably transduced with H2B-mCherry lentivirus for nuclei labeling.

Mouse Embryonic Stem Cell-Derived Cardiomyocytes (mCMs$^{ESC}$):

A stable mouse ESC line for drug resistance selection of cardiomyocytes (Myh6-Puror;Rex-Blastr) was generated by lentiviral transduction and blasticidin selection, similarly to our previously reported human line[34].

mCMs$^{ESC}$ were obtained by differentiation of Myh6-Puror;Rex-Blastr mESCs in a differentiation media containing: Iscove's Modified Dulbecco Media (IMDM) supplemented with 10% FBS, 2 mM glutamine, $4.5 \times 10^{-4}$ M monothioglycerol, 0.5 mM ascorbic acid, 200 µg/mL transferrin (Roche), 5% protein-free hybridoma media (PFHM-II, Invitrogen) and antibiotics/antimycotic as embryoid bodies (EBs) until day 4 and plated onto adherent cell culture plate until 9, one day after the onset of spontaneous beating. To purify Myh6$^+$ cardiomyocytes, puromycin was added at differentiation day 9 for 24 hours. Subsequently cells were trypsinized and plated as monolayer cardiomyocytes. Conditioned media and FSTL1 treatments were typically performed 24 hours after monolayer plating. The length of the treatments is indicated in each figure legends.

Embryonic Cardiomyocytes.

Fluorescence activated cell sorting (FACS) was used to purify cardiomyocytes from Tnt-Cre;Rosa26$^{mTmG/+}$ hearts from e12.5 embryos. Hearts were dissociated collagenase IV digestion and GFP$^+$ cells for FACS purification. The GFP$^+$ cells were cultured and confirmed to be cardiomyocytes by their expression of the cardiomyocyte specific markers alpha actinin (ACTN2) and cardiac troponin T (TNNT2). They were rhythmically beating when cultured in vitro.

Rat Epicardial Mesothelial Cells (EMC) Conditioned Media.

EMC 33 cells were cultured in 10% FBS DMEM with pen/strep until confluent ($\sim 1 \times 10^6$/cm$^2$), then washed with PBS 3 times and media is changed to serum free DMEM with pen/strep without phenol red and cultured for 2 additional days before the media was collected as conditioned media (20 ml of media is added for conditioning and 18 ml is collected after 2 days). Collected media was filtered through 0.22 µm pore membrane (Millipore). Control conditioned media were prepared the same way but without EMC cells.

Adult mouse EPDC conditioned media was generated in the Zhou laboratory[9]. Briefly, eight-week old adult Wt1CreERT2/+;Rosa26mTmG/+ hearts mice were injected orally 4 mg tamoxifen by gavage, four to five oral injections were administered during a two-week period. Myocardial infarction was then induced by ligation of left anterior descending coronary artery on (11 weeks old) adult mice. One week after injury, wt1$^{CreERT2/+}$;Rosa26$^{mTmG/+}$ hearts were collected, which were then digested with collagenase IV into single cells. Digestion solution was made by adding 4 ml 1% collagenase IV and 1 ml 2.5% trypsin into 44.5 ml Hanks' Balanced salt solution, and supplemented with 0.5 ml chicken serum and 0.5 ml horse serum. Cells were re-suspended in Hank's balanced salt solution, 4 ml digestion solution was added to each tube and rocked gently in 37° C. shaker for 6 minutes. After removing the supernatant containing dissociated cells, another 4 ml digestion solution was added to repeat the digestion 6 times. After final digestion, the cells were filtered through 70 μm filter and pellet cells by centrifuging at 200 g for 5 minutes at 4° C. Cells were then re-suspended by Hanks' balanced salt solution for FACS isolation. Dissociated cells from GFP- hearts were used as a control for gate setting in FACS. GFP+ cells (epicardium-derived cells, EPDCs) were isolated from GFP$^+$ Wtl$^{CreERT2/+}$; Rosa26$^{mTmG/+}$ hearts by FACS and these GFP$^+$ purified populations were confirmed to be GFP$^+$ cells under fluorescence microscope. FSTL1 expression (determined by PCR) was restored in cultured GFP+EDPCs. Complete conditioned media from EPDCs was then added to the myocytes assay. Dilutions are as indicated in the figure legend.

Proliferation of cardiomyocytes treated with conditional medium was measured by MTT assay using Celltiter 96 Aqueous One solution (Promega) as previously described[9]. After adding the Celltiter 96 Aqueous One reagent into the cell culture medium, the plate was incubated at 37° C. for 3-4 hours, and then record the absorbance at 490 nm using a 96-well plate reader. Absorbance at 490 nm is tightly correlated with cell number. The MTT readout on the y-axis, labeled MTT assay (A490), thus reflects the relative number of cells from each well between groups of treatment.

Calcium Imaging:

Contractile calcium transients were recorded using a Kinetic Image Cytometer (KIC, Vala Sciences) using Fluo4 NW calcium indicator (Life Science). Data was processed using Cyteseer software containing the KIC analysis package (Vala Sciences) as described[38].

RNA Extraction and Q-RT-PCR:

Total RNA was extracted with TRIzol (Invitrogen) and reverse transcribed to cDNA with QuantiTect Reverse Transcription Kit (Qiagen) according to the manufacturer's instructions. cDNA samples synthesized from 100 ng of total RNA were subjected to RT-QPCR with LightCycler 480 SYBR Green I Master kit (Roche) performed with LightCycler 480 Real-Time PCR System (Roche). Primer sequences used in this Example as well as the other Examples disclosed herein are listed below:

| Gene | Forward Primer | Reverse Primer |
|---|---|---|
| Gapdh | aatggatacggctacagc (SEQ ID NO: 3) | gtgcagcgaactttattg (SEQ ID NO: 4) |
| Myh6yh6 | catgccaatgacgacct (SEQ ID NO: 5) | cctacactcctgtactgcc (SEQ ID NO: 6) |
| Myh7 | gccaaaacaccaacctgtcca agttc (SEQ ID NO: 7) | ctgctggagaggttattcc tcg (SEQ ID NO: 8) |
| Mlc2v | aggtccaattaacttcaccgt (SEQ ID NO: 9) | gtcagcatctcccggacata (SEQ ID NO: 10) |
| Mlc2a | accgtcttcctcacact (SEQ ID NO: 11) | cttgtctgcctgggtca (SEQ ID NO: 12) |
| Ki67 | cctttgctgtccccgaaga (SEQ ID NO: 13) | ggcttctcatctgttgctt cct (SEQ ID NO: 14) |
| Myc | ccctatttcatctgcgacgag (SEQ ID NO: 15) | gagaaggacgtagcgaccg (SEQ ID NO: 16) |
| Ccnd1 | acttgaagtaagatacggagg (SEQ ID NO: 17) | gcgtaccctgacaccaatct c (SEQ ID NO: 18) |
| Cdkn1a | cgctgtcttgcactctggt (SEQ ID NO: 19) | cgttttcggccctgagatgt t (SEQ ID NO: 20) |
| Cdkn1b | tcaaacctgagagtgtctaac g (SEQ ID NO: 21) | ccgggccgaagagatttctg (SEQ ID NO: 22) |
| Cdkn2b | ccctgccacccttaccaga (SEQ ID NO: 23) | gcagatacctcgcaatgtca c (SEQ ID NO: 24) |
| Cdkn2a | acatcaagacatcgtgcgata tt (SEQ ID NO: 25) | ccagcggtacacaaagacca (SEQ ID NO: 26) |
| Atp2a2 | tcagcaggaactttgtcacc (SEQ ID NO: 27) | aatatgagcctgaaatgggc (SEQ ID NO: 28) |
| Nppa | tgacacaccacaagggctta (SEQ ID NO: 29) | gggggtaggattgacaggat (SEQ ID NO: 30) |
| Nppb | gaggtcactcctatcctctgg (SEQ ID NO: 31) | gccatttcctccgactttc tc (SEQ ID NO: 32) |
| Vegfa | aatgctttctccgctctgaa (SEQ ID NO: 33) | gatcatgcggatcaaacctc (SEQ ID NO: 34) |

Results

Figure 1:
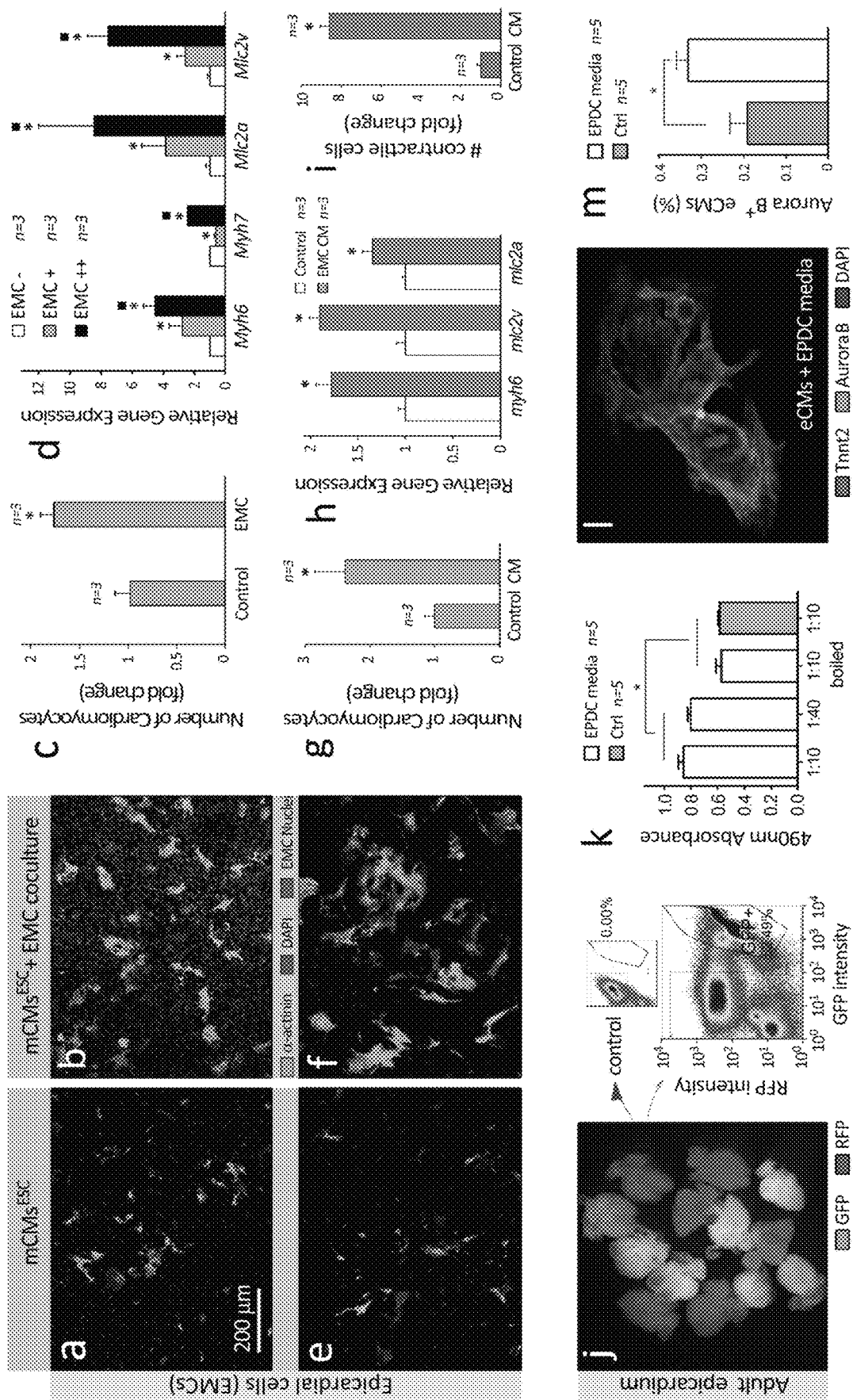
FIG. 1 depicts cardiogenic activity in the epicardial secretome. a-d) Cardiogenic effect of co-culturing ESC-derived cardiomyocytes (mCMs$^{ESC}$) with an epicardial (EMC) cell line. a,b) mCMs$^{ESC}$ only (a) and mCMs$^{ESC}$ co-cultured with EMCs for 4 days (b). Cardiomyocytes are visualized by α-actinin immunofluorescence (green) and EMCs by H2B-mCherry fluorescence (red). c) Quantification of cardiomyocyte numbers (as in a and b) expressed as fold change (n=3). d) Cardiogenic response of mCMsESC relative to the number of EMCs added to the co-culture (+: 1×10$^5$ EMCs per well, ++: 5×10$^5$ EMCs per well), quantified using the myocyte markers Myh6, Myh7, Mlc2a and Mlc2v (n=3) normalized to Gapdh gene expression. * Statistically significant difference compared to control (p<0.05), ■: p<0.05 compared to "+" condition. e-i) Effect of epicardial EMC conditioned media on cardiogenesis. e,f) α-actinin staining (green) of mCMs$^{ESC}$ after 8 days of treatment with control (e) or EMC-conditioned media (f). g) Quantification of the number of cardiomyocytes. h) Quantification of cardiac-specific markers in mCMs$^{ESC}$, normalized to Gapdh expression. i) Quantification of the number of cardiomyocytes with rhythmic calcium transient measured automatically using a Kinetic Imaging Cytometer (Vala Sciences). Quantification in g-i represented as fold change. n=3 in all experiments. * Statistically significant difference compared to control (p<0.05). j-m) Conditioned media from adult epicardial-derived cells (EPDCs) promotes cytokinesis in embryonic cardiomyocytes j) Isolation of embryonic cardiomyocytes from E12.5 GFP positive hearts (Tnnt2-Cre;Rosa26$^{MTmG/+}$). k) EPDC conditioned media promote cardiomyocyte proliferation, and boiling of conditioned media (boiled) abolished the growth-promoting effects. l, m) Cytokinesis analysis by immunostaining of Aurora B and cardiac marker Tnnt2 showed increased cardiomyocyte cytokenesis after treatment with adult EPDC media (vehicle group: 38 positive cells among 19668; conditional medium group: 74/22143); *P<0.05; n=5.
Figure 8:
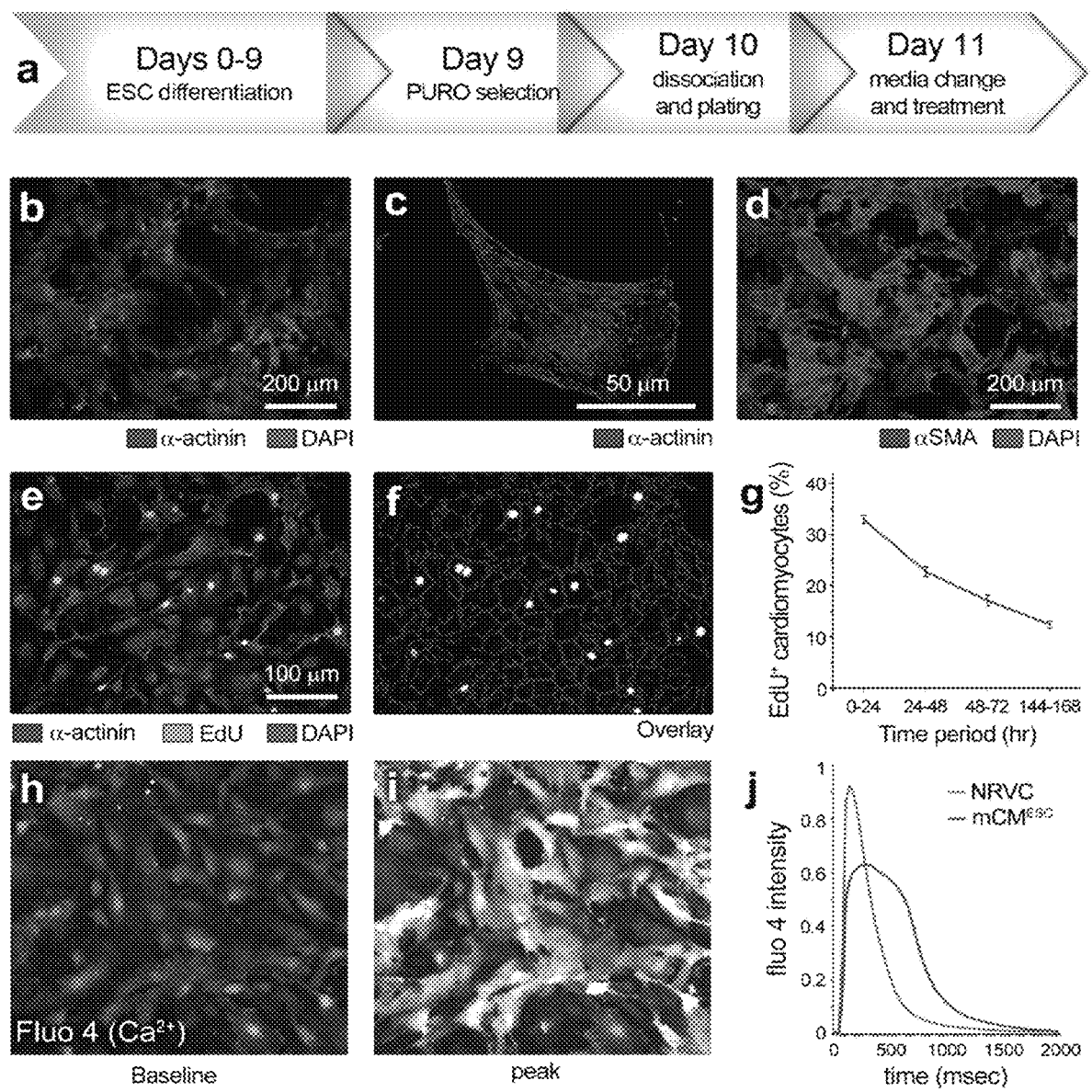
FIG. 8 depicts Characterization of mCMs$^{ESC}$ cells used in this study. a) Schematic time-line of cell preparation and treatment. b-d) Immunostaining of α-actinin of mcMs$^{ESC}$, showing that the majority of the cells are α-actinin$^+$ (b), and the α-actinin lacks striation structures (c). d) Immunostaining of a-smooth muscle actin (αSMA) of mCMs$^{ESC}$, showing the majority of the cells are αSMA$^+$, unlike mature cardiomyocytes with no SMA expression$^{42}$. e-f) Automatic detection of EdU incorporation in mCMs$^{ESC}$. Captured image of mCMs$^{ESC}$ treated with 10 µg/ml EdU for 24 hours, stained with EdU, α-actinin and DAPI using InCell 1000 General Electric) (e). Overlay of masks of EdU, α-actinin and DAPI channels with automatic detection software (f). g) EdU incorporation profile of mCMs$^{ESC}$ over time. mCMs$^{ESC}$ are treated with 10 µg/ml EdU for 24 hours at time 0 hour, 24 hours, 48 hours, and 144 hours. The percentage of EdU$^+$/α-actinin$^+$ cardiomyocytes of all α-actinin$^+$ cardiomyocytes is calculated for each time period. Note the decrease of EdU incorporation rate over time. h,i) Fluo 4 calcium images of mCMs$^{ESC}$, with baseline background image (h) and peak image (i). j) Comparison of representative calcium transients of mCMs$^{ESC}$ (red) and neonatal rat ventricular cardiomyocytes (NRVC, blue). Note the reduced amplitude, slower rate of up and down strokes, and elongated duration of the calcium transient in mCMs$^{ESC}$ compared to NRVC, suggesting immature calcium handling in mCMsESC. In all experiments, FSTL1 was added one day after plating of the mCMs$^{ESC}$ (time 0-24 in this figure).

To search for epicardial signals that promote cardiogenesis, the epicardial mesothelial cell (EMC) line was co-cultured with Myh6$^+$ mouse embryonic stem cell (ESC)-derived cardiomyocytes (referred to as mCMs$^{ESC}$). mCMs$^{ESC}$ were prepared from puromycin selection of differentiated Myh6-Puro$^r$ mouse ESCs (FIG. 8 and Materials and Methods for details and cell phenotype). Co-culture with EMCs consistently increased the number of α-actinin$^+$ myocytes (FIG. 1a-c) and expression of cardiomyocyte markers including Myh6, Myh7, Mlc2a and Mlc2v (FIG. 1d). Undiluted EMC-conditioned media recapitulated the effect of the co-culture by increasing the number of myocytes (2.4-fold α-actinin$^+$ cells detected, FIG. 1e-g) and of Myh6 (1.8-fold), Mlc2v (1.9-fold), and Mlc2a (1.3-fold) expression (FIG. 1h). Furthermore, EMC conditioned media increased the number of α-actinin$^+$ cells that exhibited rhythmic contractile Ca$^{2+}$ transients (8.6-fold) relative to standard media (FIG. 1i). Thus, secreted factor(s) from epicardial-like cultures increased the number of contractile cells in the ESC-derived cardiomyocyte cultures. Co-cultures did not promote cardiogenesis of undifferentiated (Myh6-) ESCs (not shown).

To evaluate whether adult epicardium also contains such an activity, conditioned media from epicardial derived cells (EPDCs) that had been FACS-isolated from 3-4 month-old WT1$^{CreERT2/+}$;Rosa26 m$^{TmG/+}$ mice), was prepared (FIG. 1j and Materials and Methods). When added to E12.5 embryonic cardiomyocytes (also previously FACS-isolated based on eGFP fluorescence from TNT-Cre;Rosa$^{26mTmGi+}$ mice), adult EPCD conditioned media significantly enhanced proliferation of cardiomyocytes in serum-free media (p<0.05, FIG. 1k). Boiling of the EPDC-media prior to incubation abolished the effect, consistent with the essential activity being proteinaceous. EPDC conditioned media nearly doubled the incidence of Aurora B Kinase in the cleavage furrow connecting adjacent Tnnt2$^+$ cells (0.19 to 0.33%, P<0.05, FIG. 1l,m), indicating an activity in the adult epicardium that promotes cytokinesis of embryonic cardiomyocytes.

Example 2: Engineered Epicardium Attenuates Remodeling and Improves Cardiac Function This Example describes the effect of epicardial-secreted factors in the adult heart.

Materials and Methods

Adult ventricular myocytes were isolated from 3 mo old FVB mice as previously published[35]. Briefly, mice were anesthetized with pentobarbital sodium (100 mg/kg ip). The heart was removed and retrograde perfused at 37° C. with a Ca$^{2+}$ free solution (in mM, 120 NaCl, 14.7 KCl, 0.6 KH$_2$PO$_4$, 0.6 Na$_2$HPO$_4$, 1.2 MgSO$_4$-7H$_2$O, 4.6 NaHCO$_3$, 10 Na-HEPES, 30 taurine, 10 BDM, 5.5 glucose) followed by enzymatic digestion with collagenase. Ventricles were cut into small pieces and further digested. Stop buffer (Ca$^{2+}$ free solution+CaCl$_2$ 12.5 μM+10% bovine calf serum) was added and the cell suspension was centrifuged at 40 g for 3 min. Myocytes were resuspended in stop buffer in increasing CaCl2 concentrations until 1 mM was achieved. Cells were then resuspended in MEM+5% bovine calf serum+10 mM BDM+2 mM L-Glutamine and added to the collagen solution, pre-polymerization (250,000 cells per ml or per patch). Following collagen gelation and plastic compression, cellular patches were cultured in aforementioned (plating) media overnight and then transferred into culture media: MEM+1 mg/ml bovine serum albumin+25 μM blebbistatin+2 mM L-Glutamine, in presence or absence of recombinant FSTL1 (AVISCERA BIOSCIENCE, 10 ng/ml). At day 7, fluorescent ubiquitination-based cell-cycle indicator (FUCCI, Premo™ FUCCI Cell Cycle Sensor, Life Technologies, US) assay was conducted on the 3D culture specimens as previously described[36]. In this assay, G1 and S/G2/M cells emit red and green fluorescence, respectively. The volume of Premo™ geminin-GFP and Premo™ Cdt1-RFP were calculated using the equation below:

$$\text{Volume of Premo™ geminin } GFP \text{ or Premo™ } Cdt1 \text{ } RFP \text{ reagent (mL)} = \frac{\text{number of cells} \times PPC}{1 \times 10^8}$$

where the number of cells is the estimated total number of cells at the time of cell labeling (equal to CM seeding density, PPC (particles per cell) is the number of viral particles per cell (=40 in this assay), and 1×10$^8$ is the number of viral particles per mL of the reagent. The volumes of reagents calculated above were directly added to the cellular patches in complete cell medium, mixed gently, and incubated overnight in the culture incubator (≥16 hrs). Patch samples were imaged using a conventional fluorescence microscope, utilizing GFP and RFP filter sets.

Figure 9:
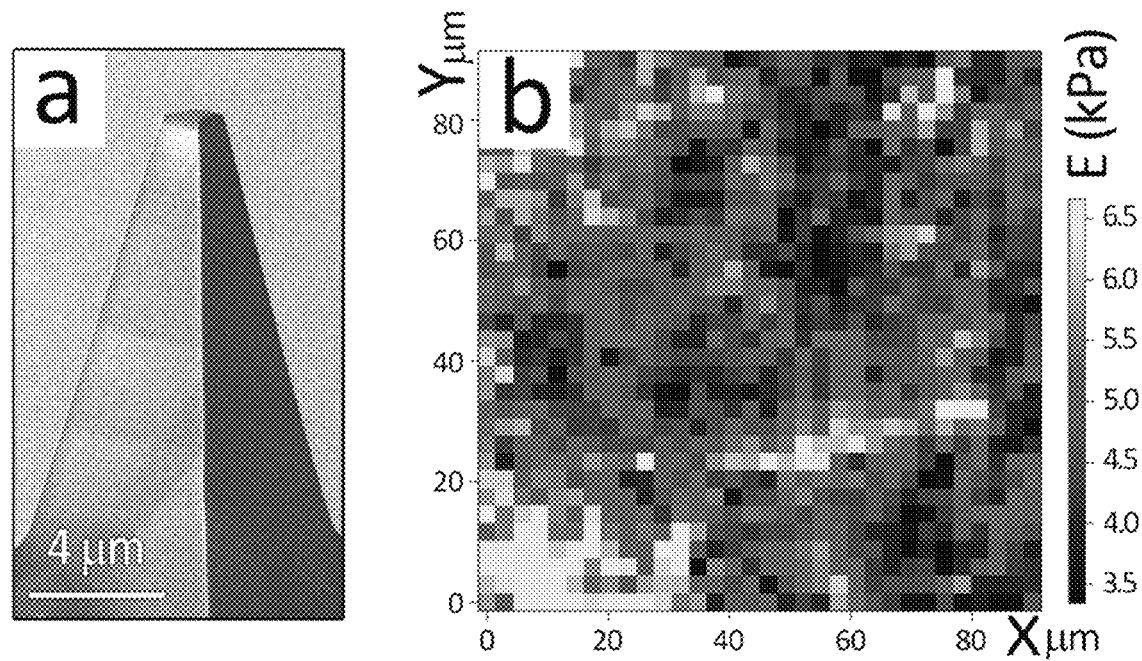
FIG. 9 depicts an atomic force microscopy (AFM) analysis of the engineered epicardial patch. The custom-made flat tip used in atomic force microscopy of the patch (a), manufactured using electron beam deposition, and utilized to probe the stiffness of the gels in scanning areas of 90 µm×90 µm (b,c).
Figure 9:
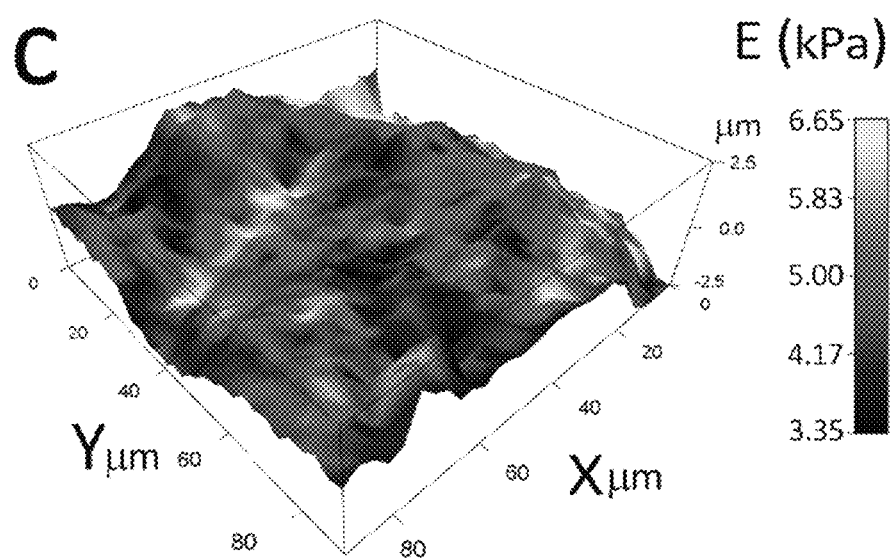

Compressed Collagen Gel for Use as an Engineered Epicardial Patch:

Highly hydrated collagen gels—used as cardiac patch in this study—were produced by adding 1.1 ml 1×DMEM (Sigma, MO, US) to 0.9 ml of sterile rat tail type I collagen solution in acetic acid (3.84 mg/ml, Millipore, Mass., US). The resulting 2 ml collagen-DMEM mixture was mixed well and neutralized with 0.1 M NaOH (~50 μl). The entire process was conducted on ice to avoid premature gelation of collagen. In the case of patches containing epicardial factors, the EMC culture media was collected as above and 0.6 ml of that was mixed with 0.5 ml DMEM. The collagen solution (0.9 ml) was then distributed into the wells of 24-well plates (15.6 mm in diameter) and placed in a tissue culture incubator for 30 min at 37° C. for polymerization. Plastic compression was performed as described previously[39,40] in order to remove excess water and produce a dense biomaterial with improved biological and mechanical properties. Briefly, as cast, highly hydrated collagen gels (at ~0.9 ml volume) underwent unconfined compression via application of a static compressive stress of ~1,400 Pa for 5 minutes (see[39,41] for details), resulting in ~98-99% volume reduction. The elastic modulus of the compressed collagen, aimed to approximate that of the embryonic epicardium which is optimal for contractility of immature cardiomyocytes[32]), was assessed by atomic force microscopy (AFM) in nano-indentation mode, using a force trigger that resulted in a minimal local strain of less than 10% (indentation of ~100 nm) to minimize the effect of substrate-related artifacts. A custom-made flat AFM tip was manufactured using focused ion beam milling and utilized to probe the stiffness of the gels by scanning areas of 90 μm×90 μm (FIG. 9 a-c).

Permanent LAD Occlusion (MI):

Male 10-12 weeks old C57BL/6J mice were purchased from Jackson Laboratories (Bar Harbor, Me., USA). The procedures involving animal use and surgeries were approved by the Stanford Institutional Animal Care and Use Committee (IACUC). Animal care and interventions were provided in accordance with the Laboratory Animal Welfare Act. Mice were anesthetized using an isoflurane inhalational chamber, endotracheally intubated using a 22-gauge angio-catheter (Becton, Dickinson Inc., Sandy, Utah) and connected to a small animal volume-control ventilator (Harvard Apparatus, Holliston, Mass.). A left thoracotomy was performed via the fourth intercostal space and the lungs retracted to expose the heart. After opening the pericardium, a 7-0 suture was placed to occlude the left anterior descending artery (LAD) ~2 mm below the edge of the left atrium. Ligation was considered successful when the LV wall turned pale. In the case of experimental groups treated with patch, immediately after the ligation, prepared collagen patch was sutured (at two points) onto the surface of ischemic myocardium. Animals were kept on a heating pad until they recovered. Another group of mice underwent sham ligation; they had a similar surgical procedure without LAD ligation. A minimum number of n=8 was used in each study group.

TTC Staining:

At day 2 post MI/patch treatment, the mouse hearts from all four groups were harvested and sectioned perpendicularly to the long axis into four sections (approximately 2 mm thick). The sections were placed in the wells of a 12-well cell culture plate and incubated with 1% 2,3,5-triphenyltetrazolium chloride (TTC, Sigma-Aldrich) solution for 15 mins at 37° C. Subsequently sections were washed with PBS and visualized using a stereomicroscope and photographed with a digital camera.

Echocardiography:

In vivo heart function was evaluated by echocardiography two and four weeks after LAD ligation. Two-dimensional (2D) analysis was performed on mice using a GE Vivid 7 ultrasound platform (GE Health Care, Milwaukee, Wis.) equipped with 13 MHz transducer. The mice were sedated with isoflurane (100 mg/kg, inhalation), and the chest was shaved. The mice were placed on a heated platform in the supine or left lateral decubitus position to facilitate echocardiography. 2D clips and M-mode images were recorded in a short axis view from the mid-left ventricle at the tips of the papillary muscles. LV internal diameter (LVID) and posterior wall thickness (LVPW) were measured both at end diastolic and systolic. Fractional shortening (FS, %) and ejection fraction (EF, %, via extrapolation of 2D data) were calculated from LV dimensions in the 2D short axis view. A minimum number (n) of 8 mice per experimental group was used for the echo evaluations. Measurements were performed by two independent groups in a blind manner.

Results

Figure 2:
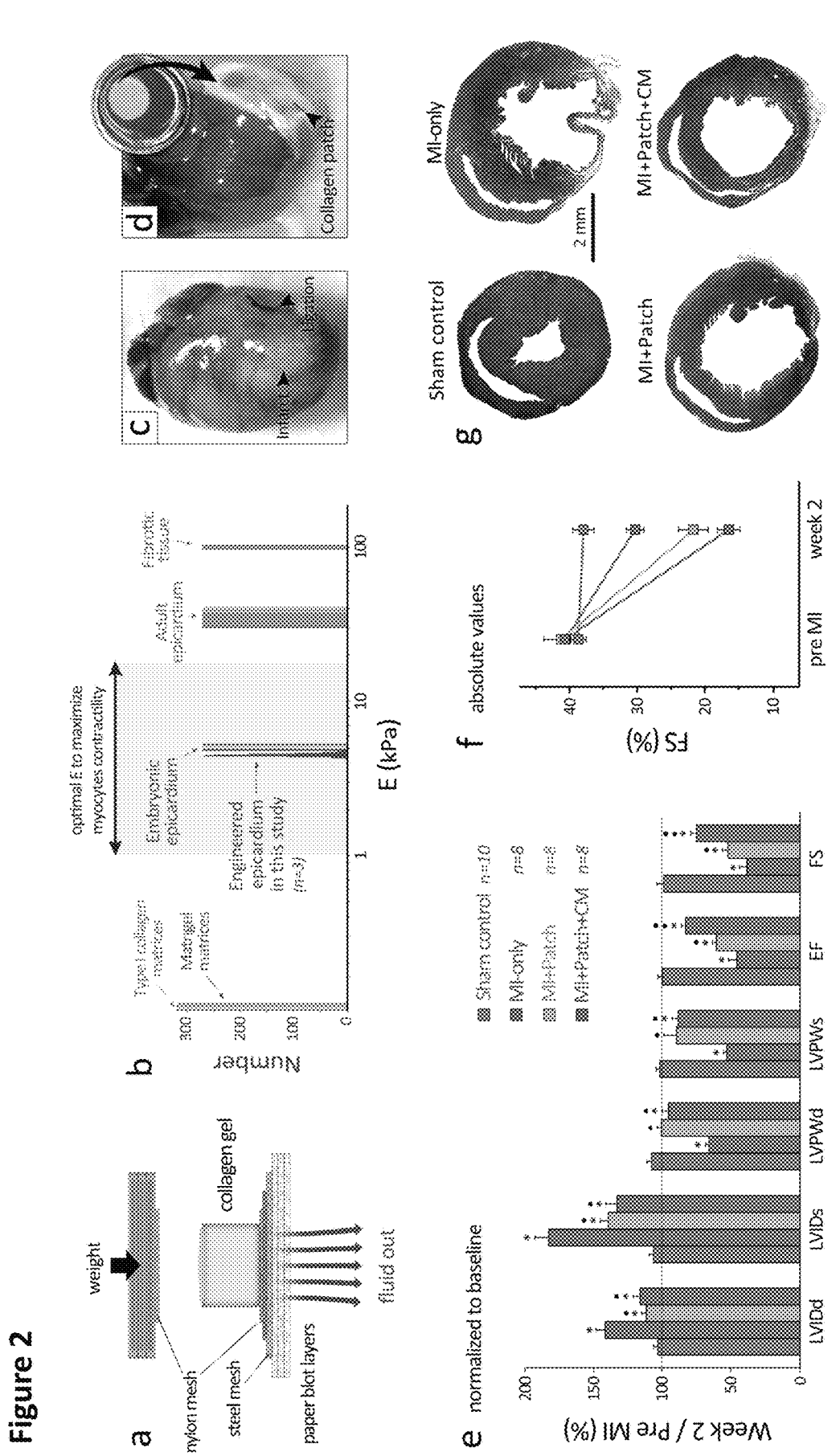
FIG. 2 depicts embryonic epicardium-like patches improve cardiac function after permanent LAD ligation. a) Schematic illustration of collagen patch generation (plastic compression procedure, reconstructed from [30]). b) Evaluation of mechanical properties of engineered patch, measured by atomic force microscopy. Histogram of the distribution of measured microstiffness of the patch is shown in red. These values are plotted relative to the range of elasticity reported for common scaffolding biomaterials[31]. Gray area depicts the previously described[32], optimal range of elasticity to maximize myocyte contractility. c, d) Epicardial-mimetic patch implantation. After permanent LAD ligation to induce myocardial infarction (c), the epicardial patch was sutured at two points onto the surface of ischemic myocardium (d). The inset in panel demonstrates a prepared patch immersed in the culture media before implantation. e-g) Physiological effects of epicardial-conditioned media-loaded patches after myocardial infarction (MI). All samples were collected at week-2 after patch implantation. e) Summary of echocardiography analysis 2 weeks after infarction, including: sham (Sham control), infarcted mice without treatment (MI-only), MI treated with patch-only (MI+Patch), and infarcted animals treated with patch laden with epicardial conditioned media (MI+Patch+CM). All data are normalized to individual pre-surgery baseline values. f) Absolute values of fractional shortening (FS %) from e. g): Gross histological analysis of Masson's trichrome stained hearts; samples are as indicated. A minimum number (n) of 8 mice per experimental group was used. *: p<0.05 compared to Sham control, ●: p<0.05 compared to MI-only, and ■: p<0.05 compared to MI+Patch.

The effect of epicardial-secreted factors in the adult heart was next evaluated by delivering conditioned media using epicardial 3D-collagen patches. The 3D collagen patches (FIG. 2a) were designed to have an elastic modulus comparable to that reported for the embryonic epicardium (E~12±4 kPa)[10], which is lower than those of mature epicardium (E>30-40 kPa) and fibrotic cardiac tissue (E>100 kPa), but higher than those for most of the currently used scaffolding biomaterials (E<1 kPa) (FIG. 2b and FIG. 9). The engineered patches were seeded with EMC conditioned media and sutured onto the epicardium of infarcted adult murine hearts (FIG. 2c,d). Patch implantation was performed immediately following permanent ligation of the left anterior descending (LAD) coronary artery (Myocardial Infarction (MI)). Two weeks later, hearts treated with epicardial-media-patch (MI+Patch+CM cohort) and empty patch (MI+Patch, no conditioned media) showed significantly better morphometric parameters including left ventricular internal diameter at end-diastole and systole (LVIDs and LVIDs, respectively), and left ventricular posterior wall dimension at end-diastole and systole (LVPWd and LVPWs, respectively) relative to MI-only animals (FIG. 2e and Table 1), consistent with a model in which the collagen patch provides mechanical support that inhibits pathological remodeling[10]. Notably, MI+Patch+CM treatment provided an additional benefit relative to all other conditions, with significantly better parameters of ventricular contractility (FIG. 2e, f and Table 1), thus indicating an epicardial-secreted activity involved in function preservation.

Example 3: FSTL1 is an Epicardial Factor Capable of Inducing Cardiomyocyte Proliferation This Example provides data suggesting that FSTL1 plays a role in epicardial-myocardial cross-talk to promote cardiomyogenesis.

Materials and Methods

LC-MS/MS Analysis of Conditioned-Media:

First, Tris(2-carboxyethyl)phosphine (TCEP) was added into 1 mL of conditional media to 10 mM and the protein sample was reduced at 37° C. for 30 min. Then iodoacetamide was added to 20 mM and the solution was alkylated at 37° C. for 40 min in the dark. Mass Spectrometry Grade of trypsin (Promega) was then added to the solution as 1:100 ratio. After overnight digestion at 37° C., the sample was then desalted using a SepPack cartridge, dried using a SpeedVac and resuspended in 100 μL of 5% formic acid. The resulting peptides were analyzed on-line by an LC-MSMS system, which consisted of a Michrom HPLC, a 15 cm Michrom Magic C18 column, a low flow ADVANCED Michrom MS source, and a LTQ-Orbitrap XL (Thermo Scientific, Waltham, Mass.). A 120-min gradient of 0-30% B (0.1% formic acid, 100% acetonitrile) was used to separate the peptides, and the total LC time was 141 min. The LTQ-Orbitrap XL was set to scan the precursors in the Orbitrap at a resolution of 60,000, followed by data-dependent MS/MS of the top 4 precursors. The raw LC-MSMS data was then submitted to Sorcerer Enterprise (Sage-N Research Inc.) for protein identification against the IPI rat protein database, which contains semi-tryptic peptide sequences with the allowance of up to 2 missed cleavages and precursor mass tolerance of 50.0 ppm. A molecular mass of 57 Da was added to all cysteines to account for carboxyamidomethylation. Differential search includes 16 Da for methionine oxidation. The search results were viewed, sorted, filtered, and statically analyzed using PeptideProphet and ProteinProphet (ISB). The minimum trans-proteomic pipeline (TPP) probability score for proteins and peptides was set to 0.95, respectively, to assure TPP error rate of lower than 0.01.

Recombinant FSTL1 was purchased from AVISCERA BIOSCIENCE (00347-02-100, produced in *E. Coli*) and R&D system (1694-FN-050, produced in mouse myeloma cell line, NSO-derived).

Histology and Immunohistochemistry:

Histological analysis for this and other Examples was performed according to standard protocols for paraffin embedding. For immunohistochemistry, embedded embryos were sectioned at a thickness of 7 μm, unless described otherwise. Antibodies used in this Example and in the other Examples disclosed herein were as follows: 1:200 α-actinin (Sigma, A7811), 1:300 α-smooth muscle actin (Sigma A2547) 1:100 phospho-Histone3 (rabbit Millipore 06-570), 1:300 phospho-Histone3 (mouse Abcam ab14955) 1:100 WT1 (Abcam, ab15249), 1:250 AuroraB Millipore 04-1036 (batch 221196), 1:200 PCM1 (Sigma-Aldrich HPA023370), 1:200 FSTL1 (R&D MAB17381). At least 5 sections per staining were used for histology and 3 for immunohistochemistry studies, respectively. An inclusion criterion for the patch engraftment was that the patch covered>70% of the infarct (controlled by histology). TUNEL assays were performed on frozen sections as instructed (Roche 11684795910).

Results

To identify bioactive epicardial secreted protein(s), EMC-conditioned media was analyzed by mass spectrometry. Comparison of spectra to the IPI rat database identified 1596 peptide reads corresponding to 311 unique proteins, of which 95 reads were due to 16 discrete secreted proteins. Ten proteins with the highest spectral counts were selected for testing in the mCMsESC assay. Of these, cardiogenic activity was noted only with Follistatin-like-1 (also known as FSTL1, FRP or TSC36) (FIG. 3a), which is a secreted glycoprotein of the BM-40/SPARC/Osteonectin family that shares a single cysteine-rich domain with Follistatin. Unlike Follistatin, FSTL1 does not block Activin and its biochemical and biological functions are poorly characterized[11]. Delivery of FSTL1 in the heart results in short-term anti-apoptotic effects[12,13], but no myocardial repair function has been attributed to FSTL1; indeed, FSTL1 levels increase in the blood stream following acute MI and for this reason it has been considered a biomarker for acute coronary syndrome[14].

Treating mCMs$^{ESC}$ for 8 days with bacterially-synthetized recombinant human FSTL1 (10 ng/ml) increased the number of cardiomyocytes by 3-fold (FIG. 3b-d), as well as increased the levels of transcripts encoding cardiac-specific contractile proteins by 2-fold (myh6, mlc2v, and mlc2a, FIG. 3e) and the number of α-actinin$^+$ cells with rhythmic contractile Ca$^{2+}$ transients by 7-fold (FIG. 3f) without inducing hypertrophy. Indeed FSTL1 decreased myocyte cell size in a dose-dependent manner (FIG. 3g). Together, these data suggest that FSTL1 plays a role in epicardial-myocardial cross-talk to promote cardiomyogenesis.

Figure 3:
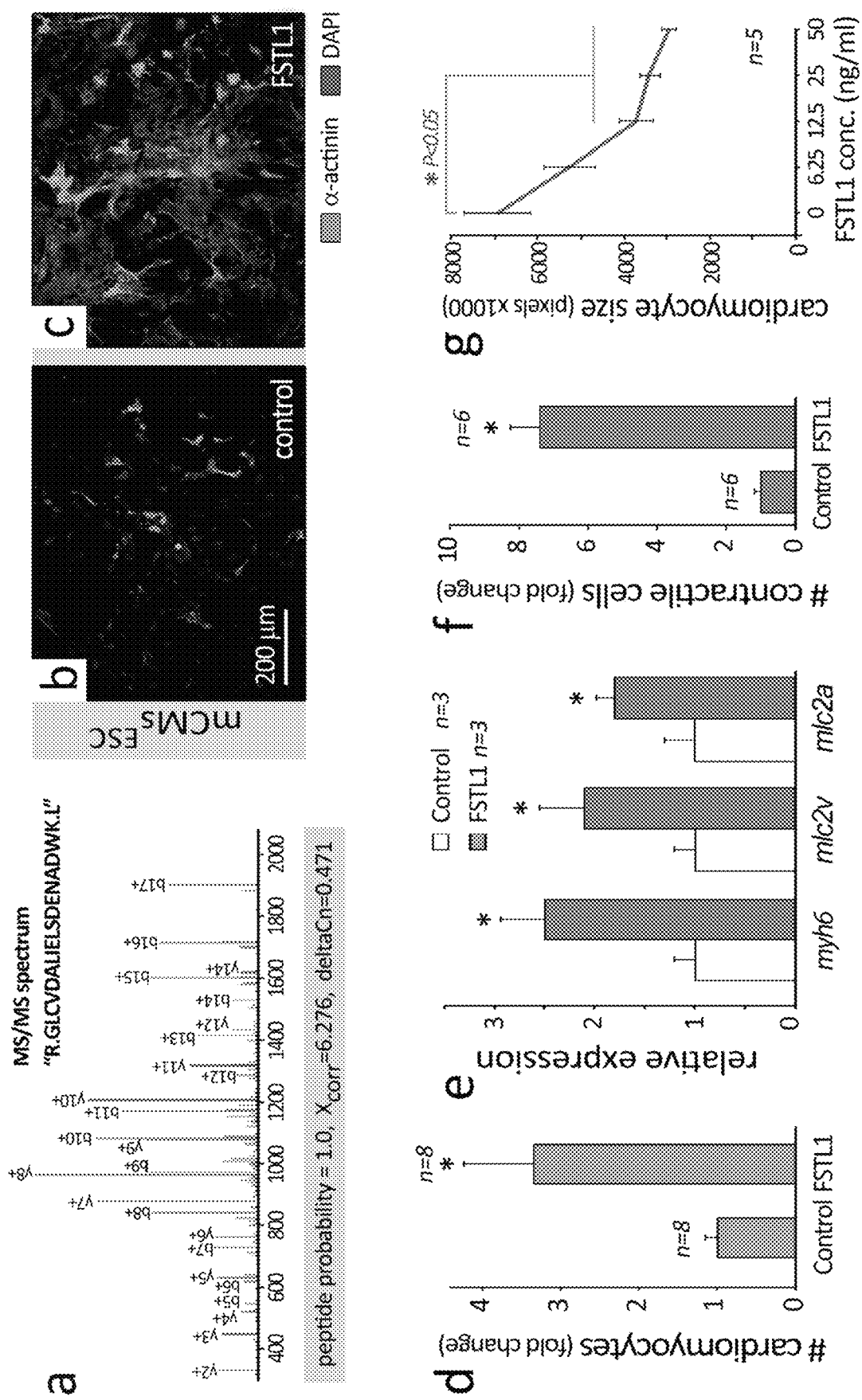
FIG. 3 depicts that FSTL1 is an epicardial cardiogenic factor with dynamic expression after injury. a) MS/MS spectrum of R.GLCVDALIELSDENADWK.L, identified as FSTL1. Peptide probability=1.0, Xcorr=6.276, delta Cn=0.471. b-f) Effect of recombinant FSTL1 on mouse embryonic stem cell-derived cardiomyocytes (mCMs$^{ESC}$) after 8 days of treatment with control media alone (control) or media containing human FSTL1 (FSTL1, 10 ng/ml). Media in all experiments and conditions were changed every 2 days. b, c) Cardiomyocytes are identified by α-actinin immunostaining (green). d) Quantification of the number of cardiomyocytes (n=8) in b, c expressed as fold change. e) Expression of cardiac-specific markers in b, c, normalized to Gapdh expression (n=3), as fold change. f) Quantification of the number of cardiomyocytes (fold change relative to control) with rhythmic calcium transient with or without FSTL1 treatment using Kinetic Image Cytometer (KIC) analysis (n=6). g) Measurement of individual cardiomyocyte cell size (in pixels) after 2 days of culture in the indicated concentrations of FSTL1 (n=5). *: statistically significant difference from control (p<0.05). h) Epicardial expression of FSTL1 after mid-gestation. Direct protein visualization using an FSTL1 antibody (red) demonstrates that FSTL1 is expressed in the mouse epicardium at embryonic days E12.5, E15.5 and E17.5. Some interstitial expression is also detected. Images of E12.5 show co-localization of FSTL1 with the epicardial transcription factor Wilm's tumor 1 (Wt1, green nuclear staining, white arrowheads). Images of E15.5 and E17.5 are co-stained with the myocyte marker α-actinin (green) and display no overlap of FSTL1 (white arrowheads) and the myocyte marker (yellow arrowhead). i-l) Dynamic expression of FSTL1 in the injured adult epicardium. i) Upper panels: Histological (Masson's Trichrome stain) evaluation of the induced fibrotic tissue at sequential times after myocardial infarction (MI). Lower panels: FSTL1 immunohistochemistry (brown) at sequential times after MI. Insets demonstrate FSTL1 expression in the epicardium of sham operated heart, and depletion of FSTL1 in the epicardium of the injured hearts. FSTL1 is also undetectable in the fibrotic tissue, while it becomes upregulated in the myocardium after MI (observe brown FSTL1 immunostaining in the myocardium post-MI). j-l) High resolution immunofluorescent images: Co-localization of FSTL1 (red) with the epicardial marker Wt1 (green) in the un-injured (sham) adult heart (j). Selective epicardial localization of FSTL1 (red) in the adult sham heart (k). FSTL1 is absent in epicardial cells and their derivatives after MI (l). Epicardial lineage labeling (green) following oral delivery of tamoxifen in Wt1-CreER;Rosa26RFP/+ mice (delivered 6 times for duration of 3 weeks and stopped 1 week before MI). Hearts were collected at 2 weeks after MI. Immunostaining of RFP for Wt1 linage cells (gray), FSTL1 (red) and Tnni3 (green) shows that FSTL1 is absent in epicardial cells and their derivatives (gray), but abundant in the myocardium (green) after MI.
Figure 10:
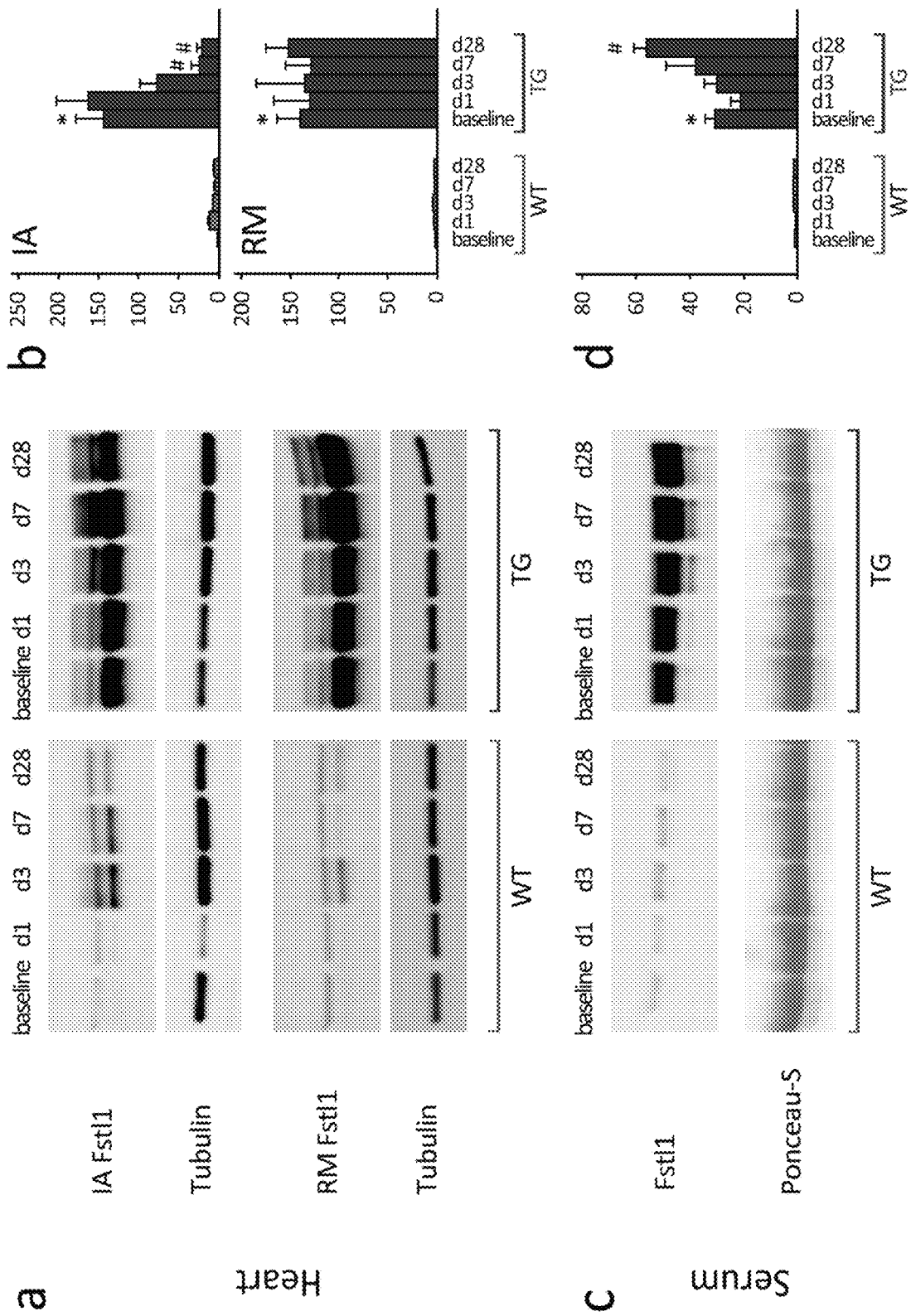
FIG. 10 depicts myocardial overexpression of FSTL1 (FSTL1-TG) mice after permanent LAD ligation. a-d) FSTL1 protein expression kinetics after myocardial infarction. FSTL1-TG mice (C57/B16 background) and littermate wildtype (WT) mice underwent LAD ligation. Heart tissue and serum were collected at baseline, day 1, day 3, day 7 and day 28 after surgery. FSTL1 protein levels in ischemic area (IA) and remote area (RM) of heart were analyzed by Western blotting (a). FSTL1 expression expressed relative to tubulin levels is reported (b). FSTL1 serum levels were analyzed by Western blotting (c). Also shown in Ponceau-S staining to indicate equal loading of serum. Quantification of serum FSTL1 level is shown in (d). n>3 in all groups. *: P<0.05 compared to WT baseline, #: P<0.05 compared to FSTL1-TG baseline. ANOVA was used for statistical significance (P<0.05). e-j) Morphometric and functional e-j) Morphometric and functional response of FSTL1-TG mice to permanent LAD ligation at long-term. Representative Masson's trichrome staining of WT (e) and FSTL1-TG (f) 4 weeks after MI. Quantification of content in fibrotic tissue at week 4 after MI (g). Echocardiographic measurement of left ventricular internal dimension in systole (LVIDs) (h), and left ventricular internal diameter in diastole (LIVDd) (i) at weeks 2, 4 after MI. Echocardiographic determination of fractional shortening (FS %) in the indicated genotypes at 2 and 4 weeks after MI (j). (k-n) Double immunofluorescent staining of α-actinin (cardiomyocytes) and pH3 (mitosis) (k) and α-actinin (cardiomyocytes) and vonWillebrand factor (vascular endothelial cells) (m) in the FSTL1-TG and WT mice, quantified in (1, n). n=5, *, significantly different (P<0.05) from WT.

Direct visualization by immunostaining revealed that FSTL1 is restricted to the epicardium as early as mid-gestation (FIG. 3h), although it is present earlier in the myocardium of the primitive heart tube[15]. Epicardial expression had not been noted previously, although it persists throughout adulthood (FIG. 3i-k). Remarkably, FSTL1 localization shifts dramatically following ischemic injury, such that it becomes abundant in the myocardium (FIG. 3 i-l) and strikingly absent in the epicardium and infarcted area (FIG. 3i,l and FIG. 10).

Example 4: Localized FSTL1 Delivery Improves Cardiac Function after MI

Prior studies have shown that transient overexpression of FSTL1 in cardiomyocytes, or direct systemic infusion of human recombinant FSTL1, is anti-apoptotic following acute ischemia/reperfusion[12,13]. Whether it confers any long-term benefit, however, is examined in this Example.

Materials and Methods

In Vivo Delayed-Enhanced Magnetic Resonance Imaging (DEMRI):

To prepare for scanning, induction of anesthesia was accomplished with 2% and maintained with 1.25-1.5% isoflurane with monitoring of the respiratory rate. ECG leads were inserted subcutaneously to monitor the heart rate while the body temperature was maintained at 37° C. Using 3T GE Signa Excite clinical scanner with a dedicated mouse coil (Rapid MR International, Germany), functional parameters were recorded on weeks 1 and 4 after treatment. The following sequences were performed for MRI acquisitions: (1) DEMRI was performed following IP injection of 0.2 mmol/kg gadopentetate dimeglumine (Magnevist, Berlex Laboratories) using gated fGRE-IR sequences with FOV 3.4 cm, slice thickness 0.9 mm, matrix 128×128, TE 5 ms, TI 150-240 ms, and FA 60°; and (2) cardiac MRI of volumes were performed using fSPGR with FOV 7 cm, slice thickness 0.9 mm, matrix 256×256, TE 5.5 ms, and FA 30. Coronal and axial scout images were used to position a 2-dimensional imaging plane along the short axis of the left ventricular (LV) cavity. A minimum number (n) of 2 mice per experimental group was used for this qualitative study.

Vessel Counting:

Blood vessel density parameters were measured from histological sections of heart samples stained for von Willebrand factor (vWF) as a marker of endothelial cells in the vessel wall. Up to 60 sections were analyzed for each treatment group (4 mice in each group). Analysis was performed using ImageJ to calculate: 1) the total luminal area of blood vessels, and 2) the number of vessels that stained+for the vWF. In each case, a histogram of the vessel parameters as a fraction of total surface area analyzed was obtained and the mid-values plotted for each treatment group. Statistical significance (p<0.05) of the differences from sham group was determined by one-tailed ANOVA.

Enzyme-Linked Immunosorbent Assay:

In order to assess the FSTL1 retention within the engineered patch system in vitro, collagen scaffolds laden with FSTL1 (5 μg/ml) were immersed in PBS and shaken for various times (0, 12 hours, 1 day, and 21 days) at 37° C. and the FSTL1 concentration was determined using Enzymelinked Immunosorbent Assay kit (USCN Life Science, Inc., Houston, USA). The detection limit for this technique was 0.50 ng/ml. Scaffolds were pretreated with 1 mg/ml collagenase type I (Sigma Aldrich, MO, US) and 5 mg/ml hyaluronidase (Sigma Aldrich, MO, US) dissolved in phosphate buffered saline for 5 minutes followed by centrifugation at 5,000×g for 20 minutes. Aliquots of 100 μl of the collected samples were added to the 96-well plates and incubated for 2 hours at 37° C. Then, 100 μL of the prepared detection reagent A were added to the wells followed by 1 hour incubation at same temperature. After aspiration and washing 3 times, 100 μl of the prepared detection reagent B was added to the wells and incubated for 30 minutes at 37° C. After aspiration and washing 5 times, 90 μL of substrate solution was added to the wells following by incubation for 25 minutes at 37° C. 50 μL of stopping solution was added to the wells and the absorbance of each well was read at 450 nm, immediately. The concentration of FSTL1 was defined using standard curve of the standard solutions. The test was performed 4 times.

Ischemia Reperfusion (I/R):

Male C57/BL6, aged 10 to 11 weeks, were anesthetized and intubated as described above. A left lateral thoracotomy was then performed. Pericardium was gently pulled off and an 8-0 Nylon suture (Ethicon, Inc. Johnson & Johnson Co., USA) was used to ligate the left anterior descending coronary artery against a PE10 tubing, which was removed after 30 minutes occlusion. Successful performance of coronary artery occlusion was verified by visual inspection (by noting the development of a pale color in the distal myocardium upon ligation). The chest was then closed using 7-0 sutures around adjacent ribs, and the skin was closed with 6-0 suture. Buprenorphine was administered subcutaneously for a minimum of 1 day at BID dosing. For the animal group treated with patch, a second thoracotomy was performed one week post the incidence of FR and the prepared collagen patch was sutured (at two points) onto the surface of ischemic myocardium. Sham-operated controls consisted of age-matched mice that underwent identical surgical procedures (two thoracotomies) with the exception of LAD ligation. In ischemia reperfusion study, in vivo heart function was evaluated pre-surgery baseline), 1 week after the incidence of FR, and two and four weeks post-implantation.

FSTL1-TG mice used in MI experiments are C57BL6 background, female and male mice age 12-15 weeks old. And the study protocol was approved by the Institutional Animal Care and Use Committee (IACUC) of Boston University.

Results

Figure 11:
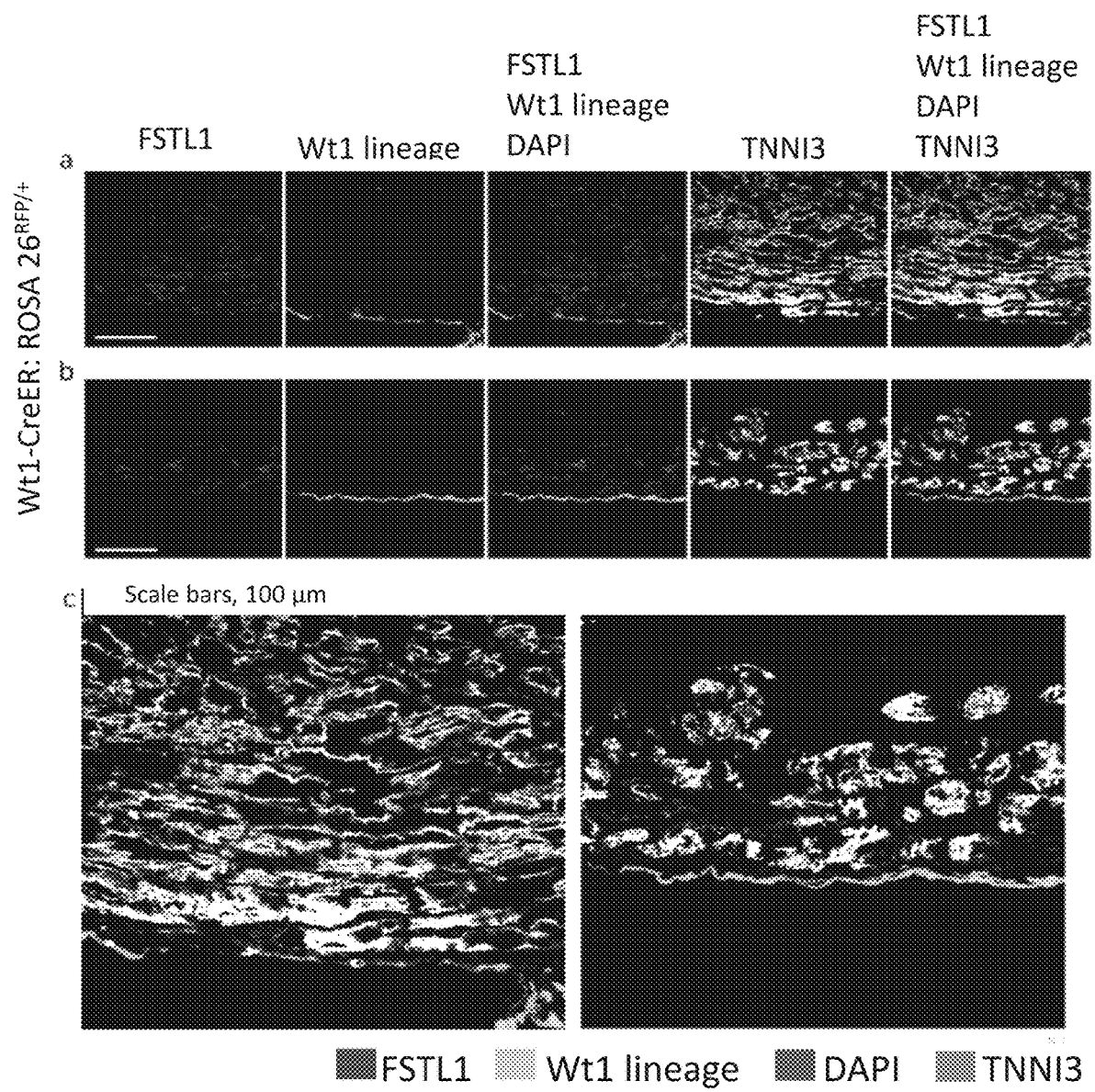
FIG. 11 shows that FSTL1 is absent from epicardium and expressed in myocardium after myocardial infarction. a-c) detection of FSTL1 after MI in lineage labeled Wt1-CreER; Rosa26$^{RFP/+}$ mice. Epicardial lineage labeling (green) following oral delivery of tamoxifen in Wt1-CreER; Rosa26$^{RFP/+}$ mice (delivered 6 times for duration of 3 weeks and stopped 1 week before MI). Hearts were collected at 2 weeks after MI. Immunostaining of RFP for Wt1 linage cells (green), FSTL1 (red) and Tnni3 (white) shows that FSTL1 is absent in epicardial cells and their derivatives (green), but abundant in the myocardium (gray) after MI (high magnification images in a, b are shown in c).
Figure 12:
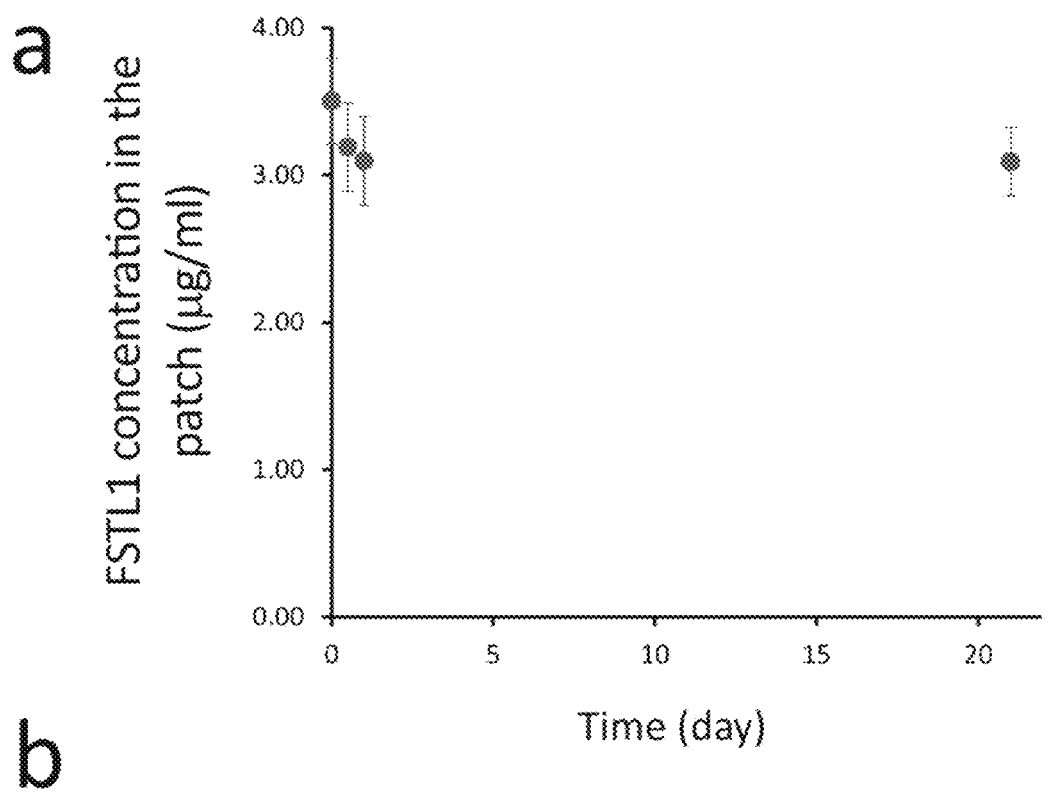
FIG. 12 depicts FSTL1 retention in the patch in vitro and in vivo. a,b) Enzyme-linked immunosorbent assay used to measure the amount of FSTL1 retained within collagen scaffolds exposed to PBS in vitro for different time intervals (0-21 days) (a). The Table lists the initial and final FSTL1 concentration, as well as the release values within the first 24 hours (b). c-f) FSTL1 retention in the patch in vivo. Representative images of FSTL1 immunostaining in the indicated animal treatment groups, week 4 after surgery. Note that, while FSTL1 is expressed in the uninjured epicardium (arrow in the inset in c), its expression became undetectable within the infarct area after MI (d). Similarly, no FSTL1 was detected in the MI+Patch animals (e), while it still persists (red staining) in the patch area of the MI+Patch+FSTL1 group (f).

Cardiac function was evaluated in transgenic mice, which expresses FSTL1 under control of the striated-muscle restricted MCK promoter (FSTL1-TG16, FIG. 11a, b). The FSTL1-TG mice displayed a small but significant improvement in contractility following permanent LAD ligation, however they showed no long-term amelioration of morphometric parameters or scar size, despite abundant FSTL1 overexpression (FIG. 11a-j). Thus, myocardial overexpression of FSTL1 is insufficient to recapitulate the cardioprotective effect of epicardial-conditioned media delivered to the epicardial surface. The effect of epicardial hFSTL1 delivery on cardiac function was assessed next. Collagen patches were prepared as before, but this time loaded with 10 µg of recombinant bacterial-synthetized hFSTL1/patch prior to polymerization and application onto the epicardial surface of infarcted hearts (see Material and Methods for details). Patches retained immune-detectable hFSTL1 up to 21 days in vitro, and 28 days in vivo, the longest times tested (FIG. 12). Freshly made hFSTL1 patches (patch+FSTL1) were applied onto the epicardial surface of hearts immediately after MI. Patch+FSTL1 resulted in significantly improved survival of animals compared to animals with MI only and patch alone (FIG. 4a).

Echocardiographic time-course measurements of contractility (% fractional shortening, FS %) demonstrated that the patch+FSTL1 caused a steady recovery of cardiac function between 2 weeks to 3 months post-MI, when FS % approached that of sham-operated animals (FIG. 4b and Table 1). In contrast, animals with no treatment showed a severe decline in FS % after 4 weeks with no subsequent improvement. Treatment with patch alone attenuated the decline in cardiac function relative to no treatment, but unlike with FSTL1, there was no subsequent improvement in cardiac function (FIG. 4b and Table 1).

reaching an improvement up to 50% by week 4 (FIG. 4c), compared to the patch-only treatment. Thus, epicardial delivery of recombinant FSTL1 is effective even in the context of myocardial transgenic overexpression of FSTL1, and further points to the specific benefits of epicardial FSTL1 delivery, beyond the patch alone or myocardial FSTL1 overexpression.

Figure 13:
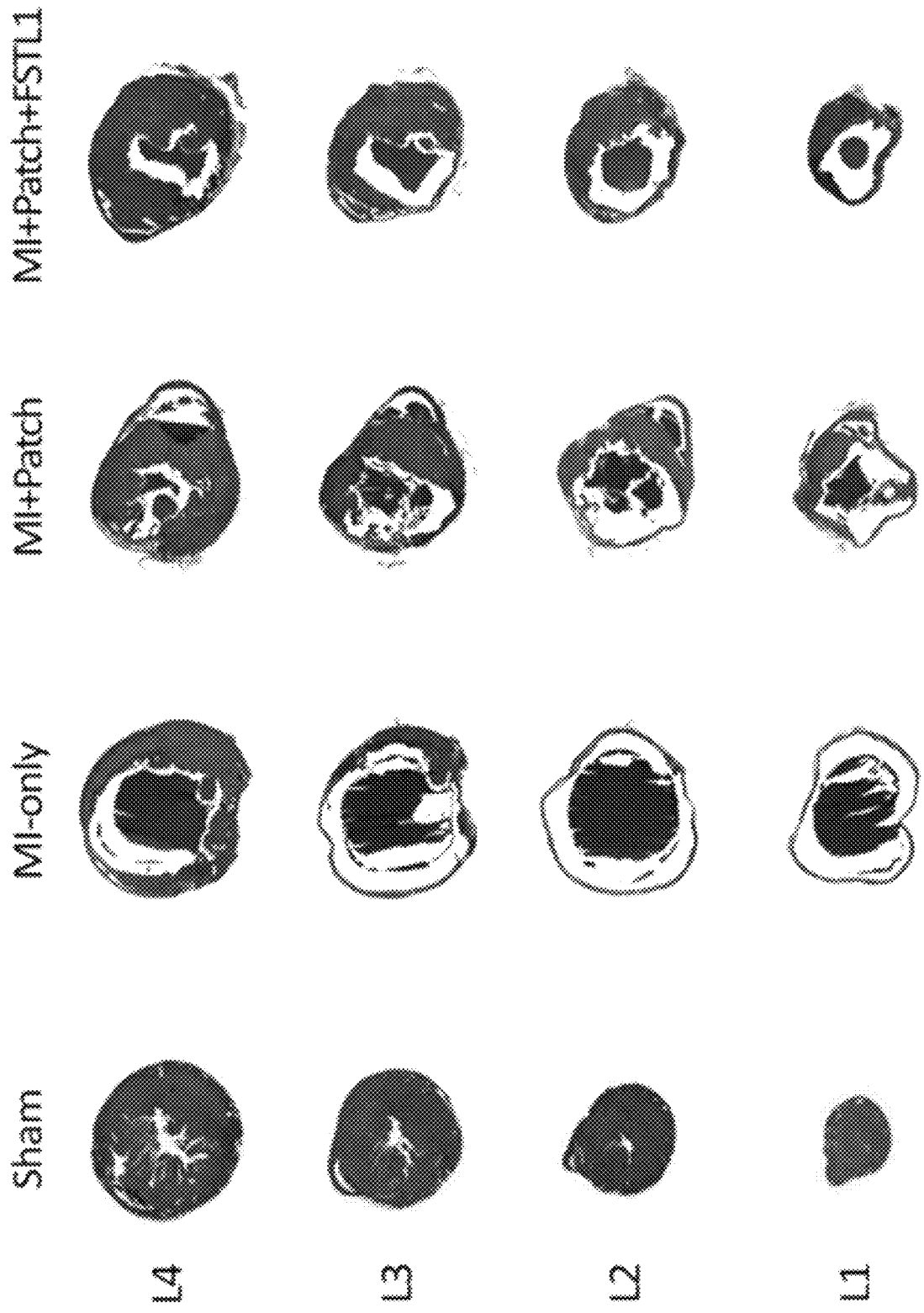
FIG. 13 depicts Patch+FSTL1 attenuated fibrosis after MI. Representative Masson's Trichrome staining on serial cross sections of hearts under 4 conditions (sham, MI only, MI+patch and MI+patch+FSTL1) 4 weeks after MI. Note the severe fibrosis in MI only condition, and reduced fibrosis in MI+Patch condition, and further reduction in MI+Patch+FSTL1 condition, quantified in FIG. 4d.
Figure 14:
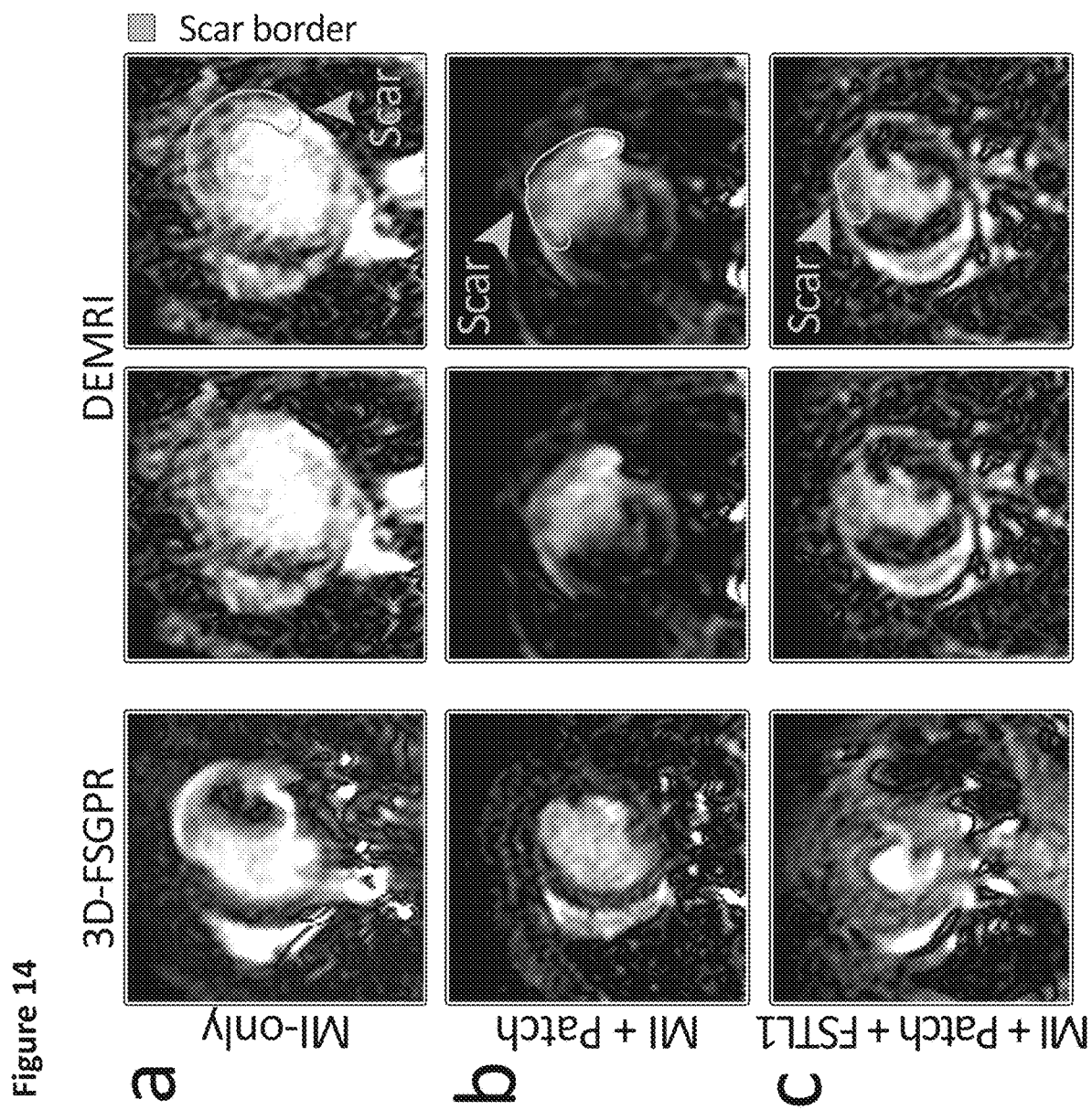
FIG. 14 depicts MRI imaging following treatment. Representative MRI images from the mouse MI-only, MI+patch and MI+Patch+FSTL1 treatment groups showing the 3D-FSPGR (fast spoiled gradient-echo) images and the delayed enhancement images utilizing gadolinium contrasting agents, confirming a reduction in infarct area (demarcated in green) and preserved contractility.

Improved cardiac function and survival were accompanied by significantly attenuated fibrosis after patch+FSTL1 implantation (FIG. 4d, FIG. 13). LV thinning was similar in the patch+FSTL1 and patch-only cohorts, with both treatments reducing LV thinning significantly relative to the MI-only condition (FIG. 4d, e and Table 1). In an independent experimental group, delayed enhanced magnetic resonance imaging (DEMRI) analysis 4 weeks post-injury confirmed that the MI+Patch+FSTL1 treatment reduced scar size (FIG. 14).

Whether the patch+FSTL1 would have a similarly beneficial effect if applied after cardiac function had declined was also investigated. For this purpose, an ischemia-reperfusion (FR) model was used and patches were implanted one

TABLE 1

Raw echocardiography values (average ± SEM) obtained at days 0 (baseline), 14, and 28 post treatment in a mouse model of permanent LAD ligation. The patch was implanted simultaneously with injury.

| | LVIDd (mm) | LVIDs (mm) | LVPWd (mm) | LVPWs (mm) | EF (%) | FS (%) |
|---|---|---|---|---|---|---|
| Sham Baseline, n = 10 | 3.89 ± 0.07 | 2.44 ± 0.07 | 1.10 ± 0.06 | 1.44 ± 0.04 | 75.40 ± 1.33 | 37.76 ± 1.48 |
| MI-only Baseline, n = 10 | 3.94 ± 0.06 | 2.28 ± 0.09 | 1.29 ± 0.09 | 1.68 ± 0.11 | 78.53 ± 1.68 | 43.50 ± 1.82 |
| MI + Patch Baseline, n = 10 | 4.08 ± 0.10 | 2.50 ± 0.16 | 1.07 ± 0.03 | 1.49 ± 0.12 | 77.75 ± 2.67 | 41.54 ± 1.98 |
| MI + Patch + CM Baseline, n = 10 | 3.84 ± 0.09 | 2.28 ± 0.07 | 1.19 ± 0.04 | 1.60 ± 0.05 | 77.63 ± 0.71 | 40.72 ± 0.66 |
| MI + Patch + FSTL1 Baseline, n = 10 | 4.04 ± 0.14 | 2.42 ± 0.11 | 1.19 ± 0.05 | 1.47 ± 0.08 | 73.12 ± 2.52 | 39.12 ± 2.04 |
| Sham Week 2, n = 10 | 3.96 ± 0.17 | 2.53 ± 0.11 | 1.14 ± 0.04 | 1.43 ± 0.07 | 73.33 ± 2.21 | 38.01 ± 1.58 |
| MI-only Week 2 post injury, n = 8 | 5.31 ± 0.23 | 4.08 ± 0.22* | 0.85 ± 0.05 | 0.91 ± 0.09 | 35.58 ± 3.57 | 16.48 ± 1.67 |
| MI + Patch Week 2 post injury, n = 8 | 4.63 ± 0.08*• | 3.56 ± 0.16*• | 1.11 ± 0.05• | 1.36 ± 0.09• | 48.17 ± 3.52*• | 21.69 ± 2.17*• |
| MI + Patch + CM Week 2 post injury, n = 8 | 4.45 ± 0.16*• | 3.10 ± 0.15*• | 1.12 ± 0.04*• | 1.40 ± 0.06*• | 64.18 ± 1.90*•■ | 30.35 ± 1.30*•■ |
| MI + Patch + FSTL1 Week 2 post injury, n = 9 | 4.77 ± 0.23*• | 3.72 ± 0.33*• | 1.02 ± 0.07*• | 1.14 ± 0.08*• | 50.31 ± 5.64*•▲ | 23.17 ± 3.05*•▲ |
| Sham Week 4, n = 10 | 3.98 ± 0.09 | 2.55 ± 0.12 | 1.02 ± 0.07 | 1.41 ± 0.07 | 71.32 ± 2.63 | 35.17 ± 1.60 |
| MI-only Week 4 post injury, n = 8 | 5.27 ± 0.20* | 4.55 ± 0.24* | 0.70 ± 0.04* | 0.78 ± 0.06* | 35.32 ± 2.64* | 12.71 ± 1.28* |
| MI + Patch Week 4 post injury, n = 8 | 5.04 ± 0.12*• | 3.77 ± 0.11*• | 1.02 ± 0.08• | 1.28 ± 0.08• | 51.43 ± 1.62*• | 22.71 ± 0.92*• |
| MI + Patch + CM Week 4 post injury, n = 8 | 4.35 ± 0.18*■ | 3.20 ± 0.24*•■ | 1.23 ± 0.05• | 1.53 ± 0.06• | 62.15 ± 4.36*■ | 27.52 ± 2.50*•■ |
| MI + Patch + FSTL1 Week 4 post injury, n = 9 | 4.24 ± 0.12*■ | 2.86 ± 0.13*• | 1.15 ± 0.06• | 1.50 ± 0.08• | 67.73 ± 1.79*■ | 32.87 ± 1.26*•■ |

*statictically significant difference (P < 0.05) in comparison with Sham.
•statictically significant difference (P < 0.05) in comparison with MI-only.
■statictically significant difference (P < 0.05) in comparison with MI + Patch.
▲statictically significant difference (P < 0.05) in comparison with MI + Patch + CM.

Figure 15:
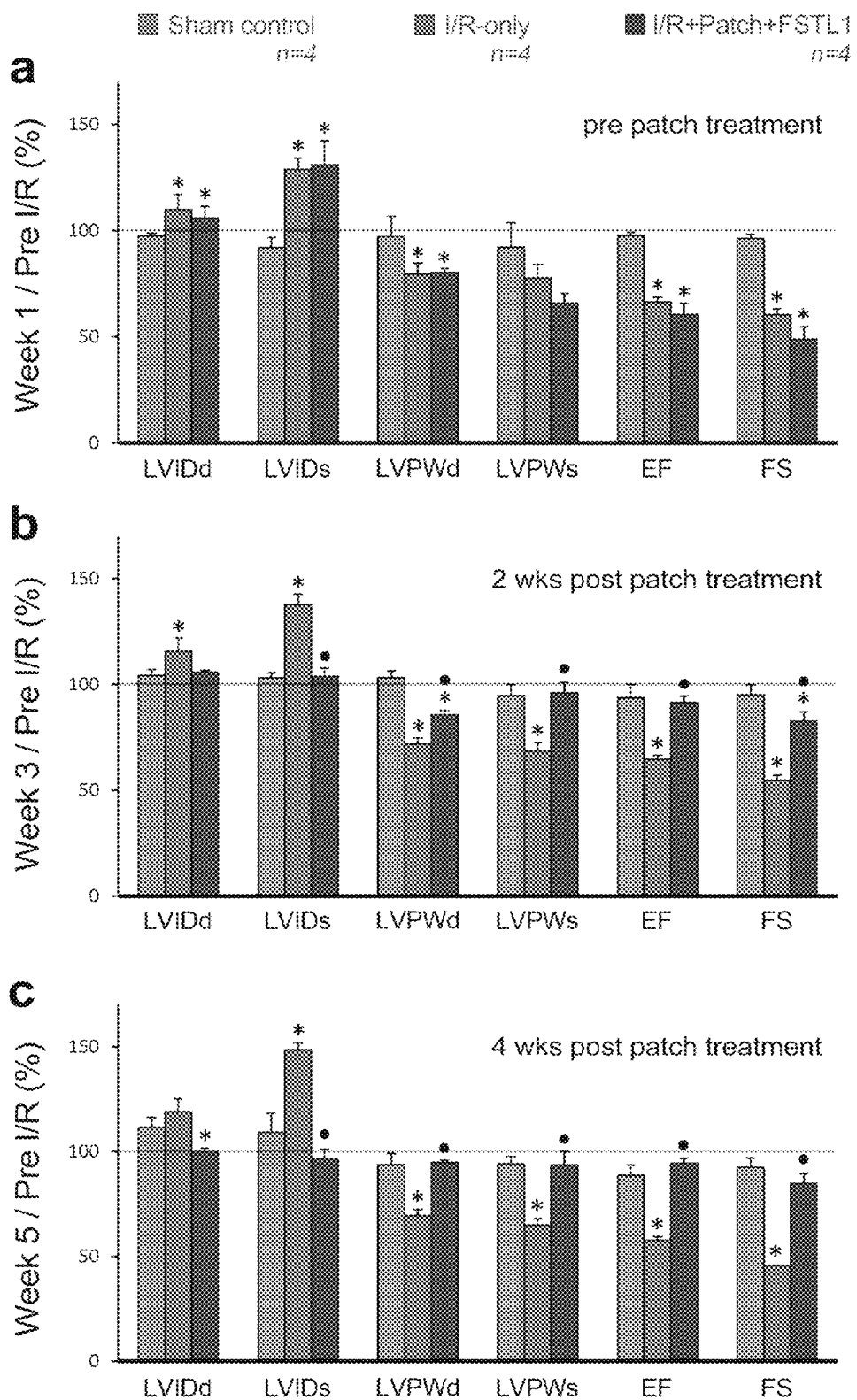
FIG. 15 depicts Analysis of patch+FSTL1 function in the mouse model of ischemia/reperfusion (FR) with delayed patch grafting a-c) Heart function evaluation for sham, FR, and FR treated with patch+FSTL1, at end-diastolic and systolic, pre-grafting (a, 1 week post injury), 2 weeks post patch implantation (b), and 4 weeks post grafting (c). Values were normalized by dividing to pre-surgery baseline values for each individual animal. d) Absolute values of fractional shortening (FS, %) at different times pre and post FR as evaluated by echocardiography of mice from a-c. Abbreviations same as in FIG. 4. *: $p<0.05$ compared to sham and ●: $p<0.05$ compared to FR. e) co-immunofluorescence staining of DNA duplication marker phospho-Histone3 Ser10 (pH3, green) and α-actinin (red) in the border zone of Patch+FSTL1 treated heart 4 weeks after MI. f) Quantification of incidence of pH3$^+$, α-actinin$^+$ double positive cells in the 3 experimental groups. Data collected from 3 hearts in each group with 3 different cross sections counted for total pH3$^+$, α-actinin$^+$ cells in each heart. *: statistically different from all other groups, $P<0.05$.
Figure 15:
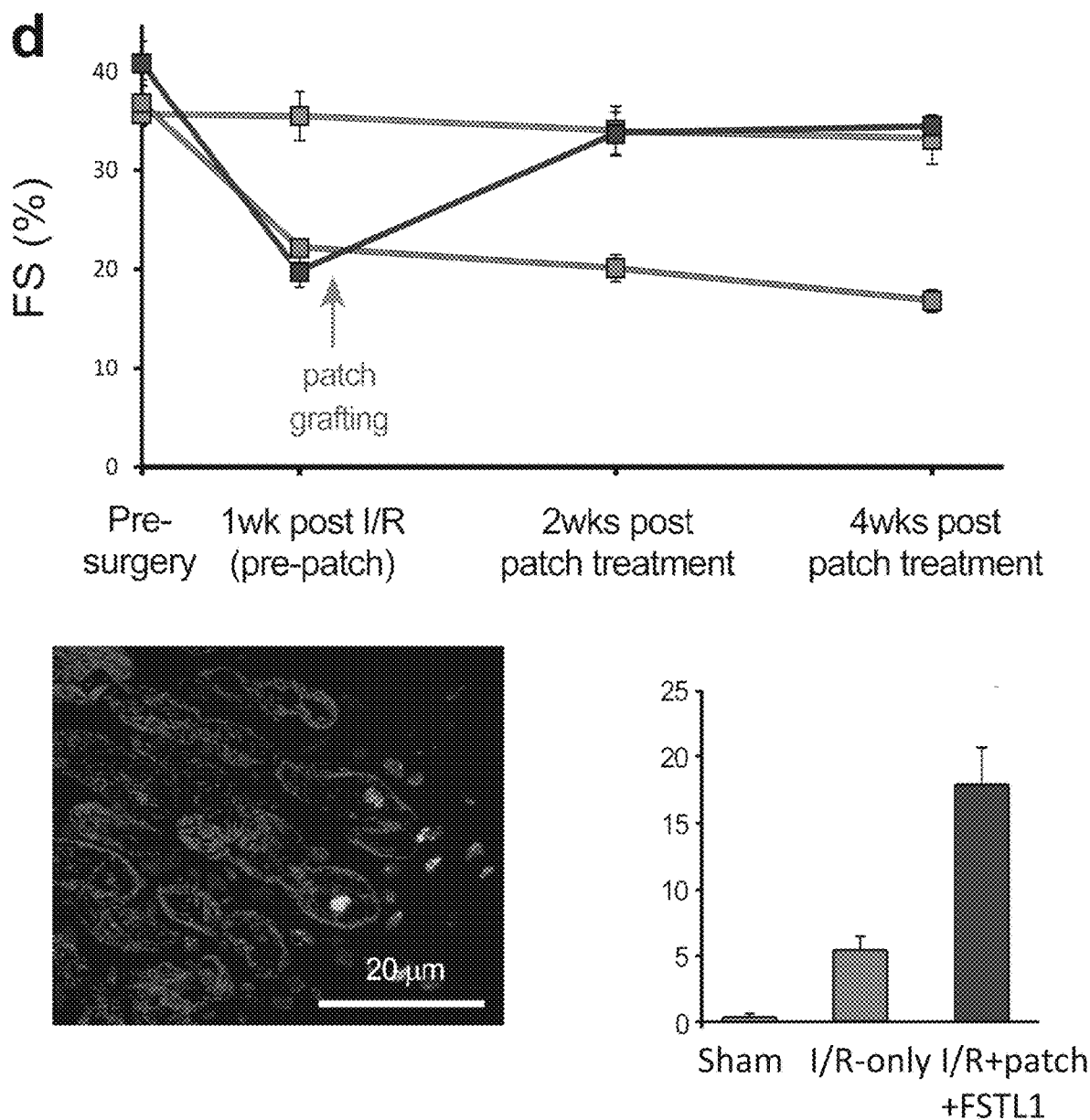
Figure 16:
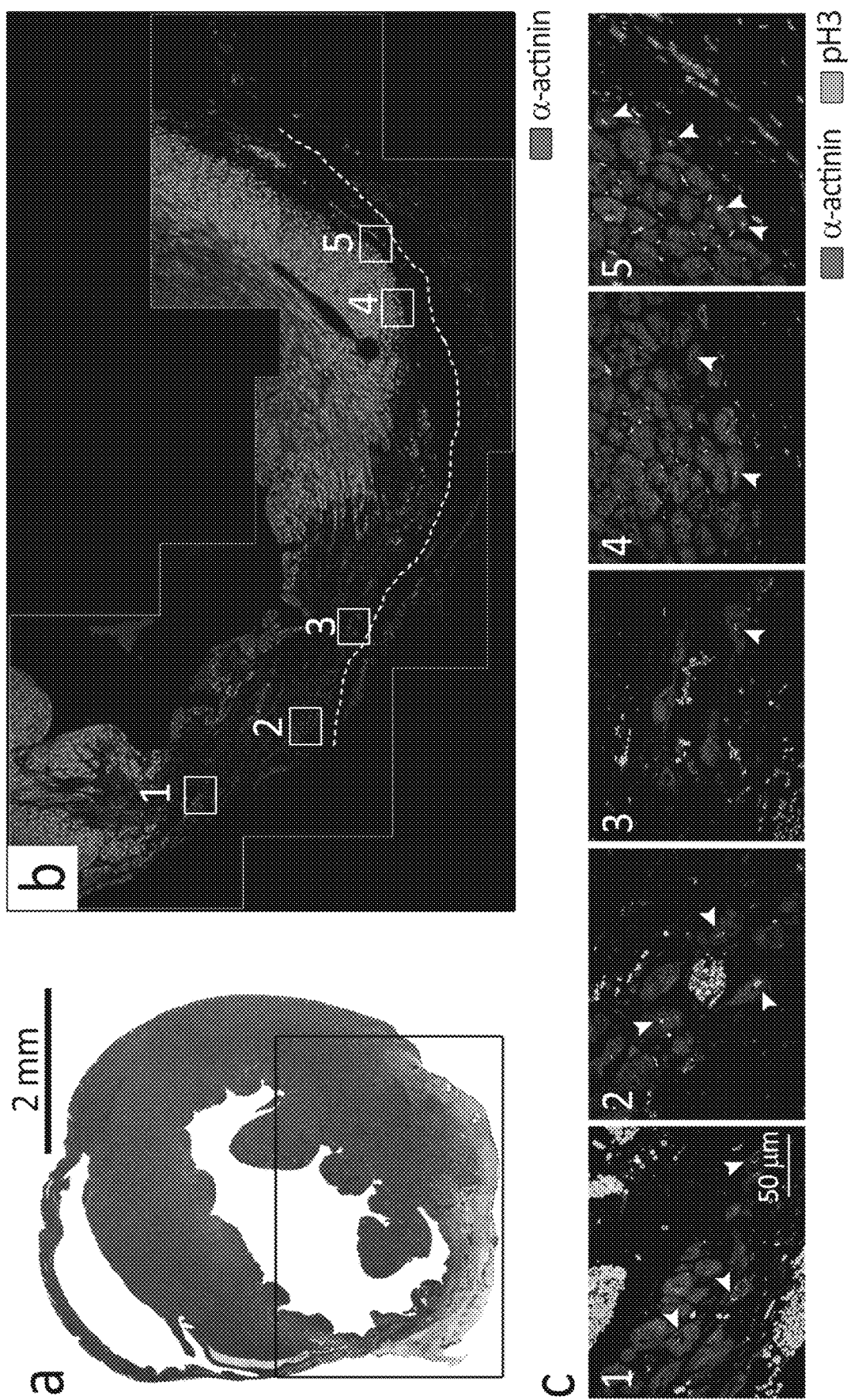
FIG. 16 depicts a representative of all pH3$^+$ cardiomyocytes detected in one section of Patch+FSTL1 Treated heart. Masson's Trichrome staining of a heart after MI 4 weeks treated with Patch+FSTL1 (a). The adjacent slide was stained for α-actinin in (b), corresponding to the black box area with infarction and the patch in (a). The spotted line in (b) indicates the boundary between the heart and the patch. The adjacent slide was stained for α-actinin and pH3, and all α-actinin$^+$, pH3$^+$ double positive cardiomyocytes found were shown in (c) (white arrowhead), with each image corresponding to the area in numbered white boxes in (b).

Whether epicardial delivery of FSTL1 is necessary to induce the beneficial effects, given that FSTL1 is upregulated in the myocardium after MI[16] was subsequently tested. This was performed by implanting patch-only or patch+FSTL1 on myocardial infarcted FSTL1-TG mice[16]. Contractility parameters were dramatically and specifically increased in the transgenic animals seeded with patch+FSTL1, with changes noticeable at week 2 of treatment and week after injury. All animals displayed reduced contractility (from 37% FS pre-injury to 22% one week after FR prior to patch placement). Cardiac function of untreated animals progressively declined (22%, 20% and 16% FS at 1, 3 and 5 weeks post-FR). In contrast, the patch+FSTL1 cohort recovered to 34% three weeks post-FR and stabilized, corresponding to a complete FS recovery (FIG. 15 and Table 2). Similar to the permanent ligation model (FIG. 4), functional recovery was accompanied by restoration of morphometric parameters (FIG. 15 and Table 2). These data indicate that epicardial-delivered FSTL1 leads to reversion of damage after ischemic injury.

TABLE 2

Raw echocardiography values (average ± SEM) in a long term (months 2 and 3) post treatment, in a mouse model of permanent LAD ligation. The patch was implanted simultaneously with injury.

|  | LVIDd (mm) | LVIDs (mm) | LPWd (mm) | LVPWs (mm) | EF (%) | FS (%) |
|---|---|---|---|---|---|---|
| Sham Month 2, n = 4 | 4.26 ± 0.05 | 2.68 ± 0.03 | 1.20 ± 0.03 | 1.41 ± 0.07 | 72.00 ± 0.41 | 35.75 ± 0.02 |
| MI Month 2, n = 4 | 5.53 ± 0.17* | 4.76 ± 0.19* | 0.73 ± 0.04* | 0.91 ± 0.09* | 33.98 ± 3.24* | 13.88 ± 1.56* |
| MI + Patch Month 2, n = 4 | 5.05 ± 0.09*• | 3.92 ± 0.04*• | 0.92 ± 0.09* | 1.27 ± 0.08* | 51.13 ± 2.70*• | 21.50 ± 1.44*• |
| MI + Patch + FSTL1 Month 2, n = 4 | 3.96 ± 0.16•■ | 2.58 ± 0.09•■ | 1.27 ± 0.04•■ | 1.50 ± 0.09•■ | 68.25 ± 0.75•■ | 33.19 ± 0.70•■ |
| Sham Month 3, n = 4 | 4.41 ± 0.13 | 3.01 ± 0.13 | 1.12 ± 0.02 | 1.34 ± 0.01 | 67.00 ± 1.74 | 32.38 ± 1.28 |
| MI Month 3, n = 4 | 4.93 ± 0.27* | 4.14 ± 0.16* | 0.90 ± 0.03* | 0.99 ± 0.09* | 38.00 ± 2.65* | 15.33 ± 1.20* |
| MI + Patch Month 3, n = 4 | 4.94 ± 0.23 | 3.68 ± 0.22* | 0.90 ± 0.10 | 1.18 ± 0.02* | 53.50 ± 2.63*• | 23.58 ± 1.57*• |
| MI + Patch + FSTL1 Month 3, n = 4 | 4.65 ± 0.04• | 3.19 ± 0.06•■ | 0.93 ± 0.09 | 1.17 ± 0.07•■ | 66.19 ± 1.12•■ | 31.38 ± 1.46•■ |

*statistically significant difference (P < 0.05) in comparison with Sham.
•statistically significant difference (P < 0.05) in comparison with MI-only.
■statistically significant difference (P < 0.05) in comparison with MI + Patch.
▲statistically significant difference (P < 0.05) in comparison with MI + Patch + CM.

FSTL1 in the patch increased vascularization of both the collagen patch and underlying myocardium at the border of the infarcted region as evaluated by von Willebrand factor (vWF) and smooth muscle actin ($\alpha$SMA) immunostaining (FIG. 4f-i). Approximately 1.5% of the patch area and subjacent myocardium were occupied by vessels in the MI+Patch+FSTL1 group, compared to a 0.9% in the MI+Patch, 0.4% area in MI-only groups (FIG. 4g). This value indicates restoration of nearly half of the vasculature observed in the comparable region of the distal LV wall of sham operated animals (3.1% area). The number of vessels (of any size) per unit surface area of histological sections also increased in the MI+Patch+FSTL1 group (82 vessels/mm$^2$) relative to the MI+Patch (35 vessels/mm$^2$) and MI-only (15 vessels/mm$^2$) treatment groups (FIG. 4i). In contrast, sham-operated animals exhibited 136 vessels/mm$^2$, again indicating that the Patch+FSTL1 restored vascularization to levels approximately half that of un-infarcted mice. Furthermore, smooth muscle cells surrounded numerous vessels, particularly in MI+Patch+FSTL1 group (FIG. 4h). Masson's trichrome staining showed contiguous engraftment of the patch+FSTL1 onto the host myocardium, and demonstrated migration of host cells into the patch including evidence of striated cells by 4 weeks after MI and patch placement (green arrows, last two columns in FIG. 4j).

Example 5: FSTL1 Induces Cardiomyocyte Cell Cycle Entry In Vivo

This Example shows that epicardial-delivered FSTL1 might have a different function that FSTL1 produced in the myocardium.

Figure 5:
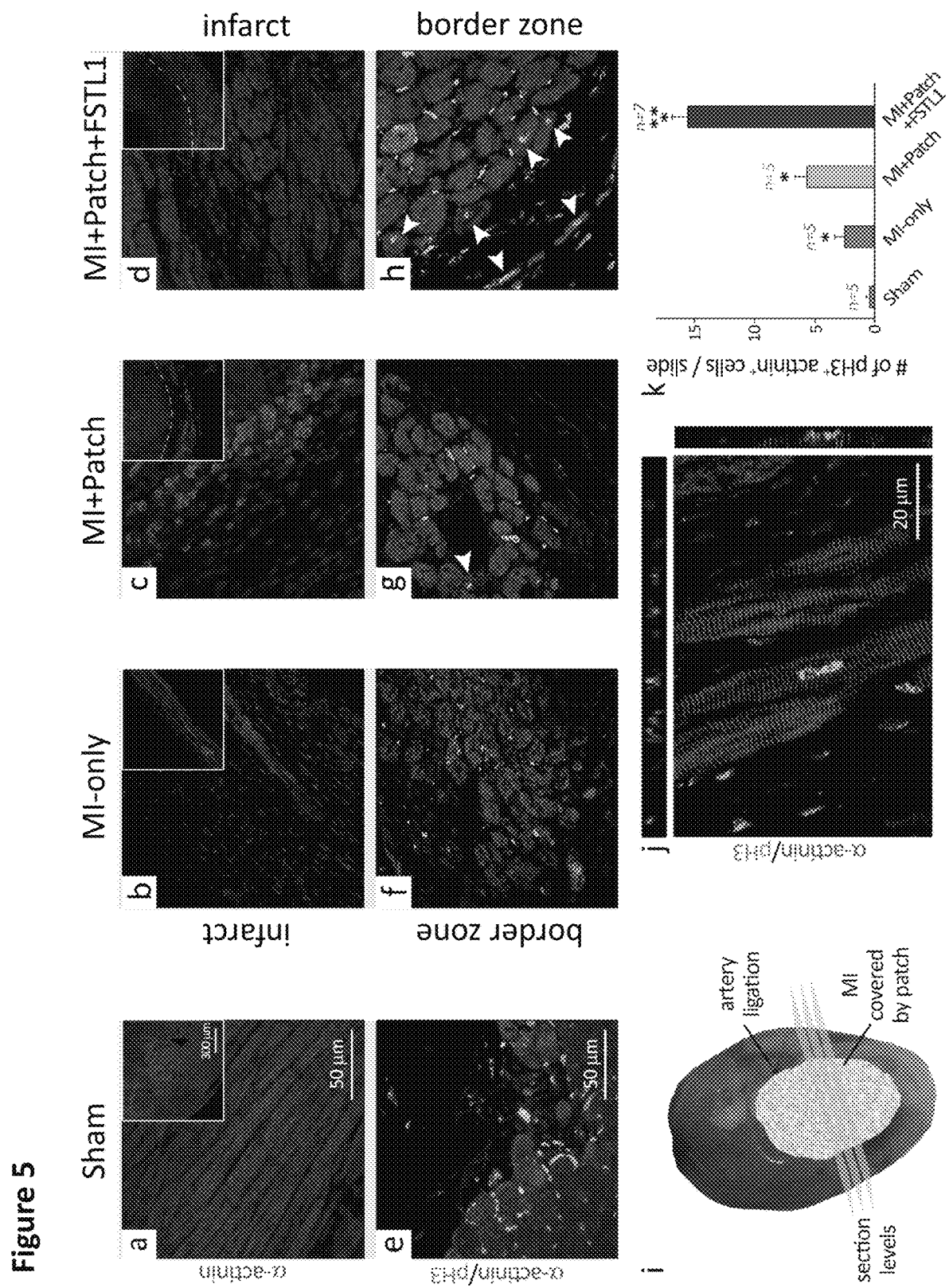
FIG. 5 depicts restored epicardial expression of FSTL1 promotes cardiomyocyte proliferation. All experiments were performed following permanent LAD ligation. Samples were analyzed at week 4 of treatment unless otherwise indicated. a-h) Immunostaining. Immunostaining of the cardiomyocyte marker α-actinin (red) in the infarct area (b-d) and co-immunofluorescence staining of DNA duplication marker phospho-Histone3 Ser10 (pH3, green) and α-actinin (red) in the border zone (f-h), in the 4 treatment groups analyzed 4 weeks post-MI, compared to sham-operated animals (a,e). Insets in (a-d) show lower magnification images with broken lines demarcating the border between the patch and host tissues. Arrowheads in (g, h) indicate α-actinin$^+$ cardiomyocytes with pH3$^+$ nuclei. i-o) Quantification of cardiomyocyte proliferation. i) Illustration of cross sections used for quantification analysis, each section covered the infarct, patch, and separated by 250 μm, between 1-2 mm from the apex. j) High magnification image of pH3 (green) and α-actinin (red) with 3D rendering showing colocalization of the cardiomyocyte nucleus with pH3 staining. k) Quantification of incidence of pH3$^+$, α-actinin$^+$ double positive cells in the 4 experimental groups. Data collected from 5-7 hearts in each group with 3 different cross sections counted for total pH3$^+$, α-actinin$^+$ cells in each heart. 1-m) Cytokinesis determination. 1) Coimmunofluorescence of cardiomyocytes (α-actinin, green) and the cytokinesis marker Aurora B kinase (red) in the patch+ FSTL1 cohort, with 3D rendering showing Aurora B kinase$^+$ cleavage furrow between α-actinin$^+$ cardiomyocytes in the Z axis. m) Quantification of incidence of Aurora B+/α-actinin$^+$ cells in the 4 experimental groups. Data collected from 5-7 hearts in each group with 3 different cross sections counted for total Aurora B+/α-actinin$^+$ cells in each heart. n-o) Proliferation determination using cardiomyocyte nuclei marker n) Co-immunofluorescence of cardiomyocyte nuclei marker PCM1 (red) and pH3 (green) in the patch+FSTL1 cohort, with 3D rendering showing colocalization of the cardiomyocyte nucleus with pH3 staining. o) Quantification of incidence of PCM1$^+$/pH3$^+$ cells in the 4 experimental groups. Data collected from 5-7 hearts in each group with 3 different cross sections counted for total PCM1$^+$/pH3$^+$ cells in each heart. *: statistically different from sham, P<0.05. **: statistically different from all other groups, P<0.05. p-v) Lineage tracing of newly generated myocytes. 4-OH-tamoxifen (OH-Tam) treatment of αMHC-mERCre-mER;Rosa26$^{Z/EG/+}$ (MCM$^+$/ZEG) mice induced eGFP expression in pre-existing cardiomyocytes (diagrammed in p). Collagen patches loaded with FSTL1 were applied simultaneously to coronary ligation (MI). The hearts were dissected, fixed and stained 4 weeks post-MI. q) LV area in sham-operated hearts showing efficient labeling of cardiomyocytes (α-actinin white; eGFP green). r-t) LV area in infarcted hearts showing eGFP+ (pre-existing, green) cardiomyocytes at 4 weeks post-surgery in intact area (r), in the infarct area (s), and in the border zone (t, u). White arrowheads indicate pH3+ non-cardiomyocytes. Yellow arrowheads show pH3$^+$, eGFP$^+$ double positive cells, indicating pre-existing cardiomyocytes in the midst of cell cycle. Observe clusters of pH3$^+$, eGFP$^+$ double-positive cells in border zone and infarct area.
Figure 17:
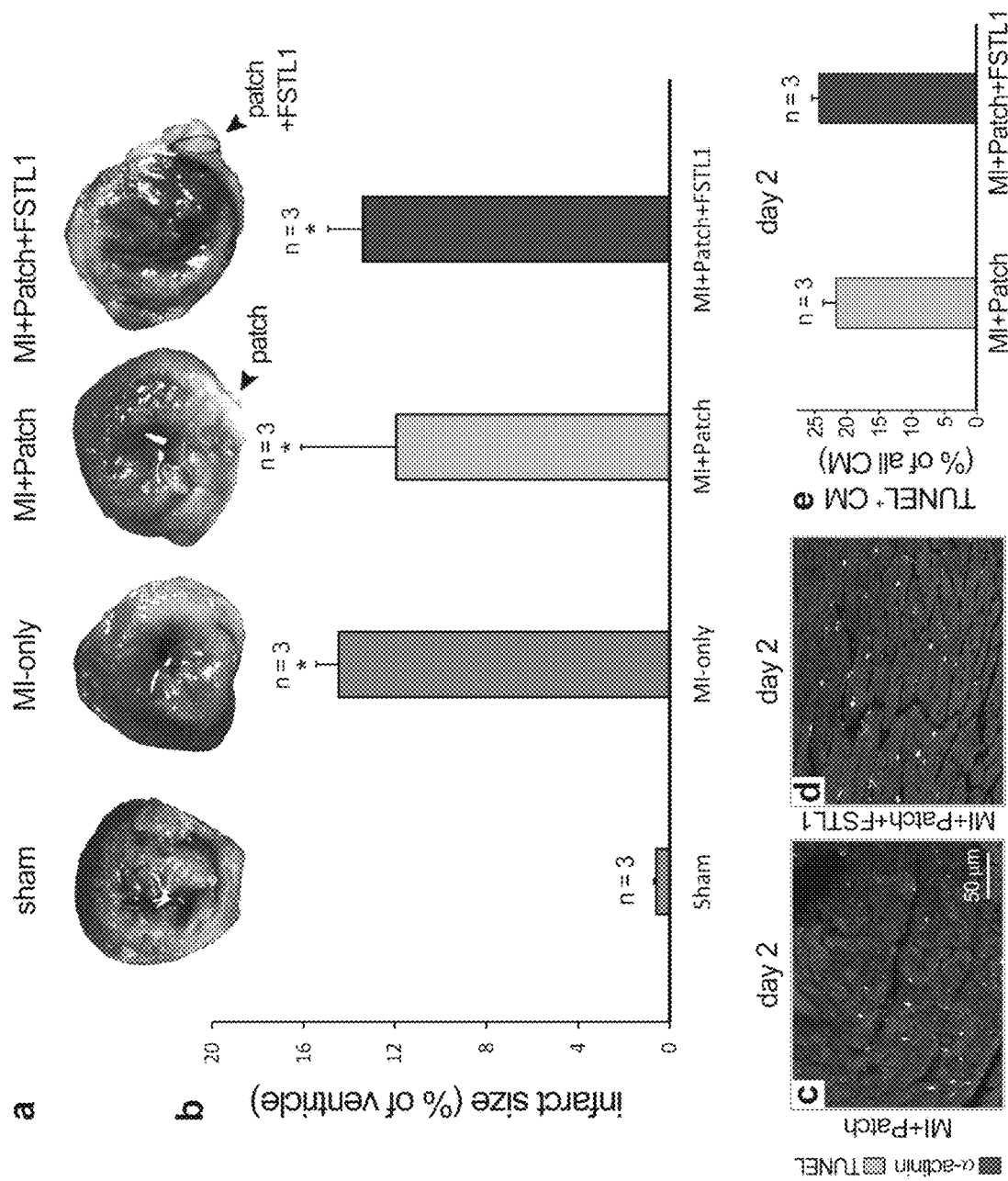
FIG. 17 depicts the effect of implantation of patch+FSTL1 on apoptosis and inflammation. a) Representative TTC staining of day 2 post MI/patch treatment of all four groups (sham, MI, MI+Patch, MI+Patch+FSTL1). b) Quantification of area at risk comparing all 4 groups. Data collected from 4 hearts in each group, with 4 cross sections, approximately 2 mm thick each, encompassing each heart. *: statistically different from the sham, $P<0.05$. c, d) Representative image of TUNEL assays (TUNEL, green, α-actinin, red) comparing hearts 2 days after MI with patch alone and patch+FSTL1. e) Quantification of TUNEL$^+$, α-actinin$^+$ in infarcted area, as percentage of total number of cardiomyocyte. No difference is observed between MI+Patch and MI+Patch+FSTL1 conditions. Data collected from 3 hearts in each group with 3 different cross sections (same as in FIG. 5 i) Ten 0.09 mm$^2$ images were taken from infarcted area of each section and counted for TUNEL+, α-actinin$^+$ and total α-actinin$^+$ cells. a-e) TUNEL staining for cell death and α-actinin staining for cardiomyocytes were performed on hearts treated with patch-only and patch+FSTL1 at day 4 and day 8 after MI (a-d). Minial TUNEL$^+$, α-actinin$^+$ cells are detected while there are signification amount of TUNEL$^+$, α-actinin cells. Quantification of all TUNEL$^+$ nuclei showed no significant differences between Patch and Patch+FSTL1 treated hearts at both time points (e). f-j) Immunostaining of F4/80 for macrophages and α-actinin for cardiomyocyte were performed on the same hearts as in panels a-d (f-i). Quantification of F4/80$^+$ cells showed no significant differences between Patch and Patch+FSTL1 treated hearts at both time points (j).
Figure 18:
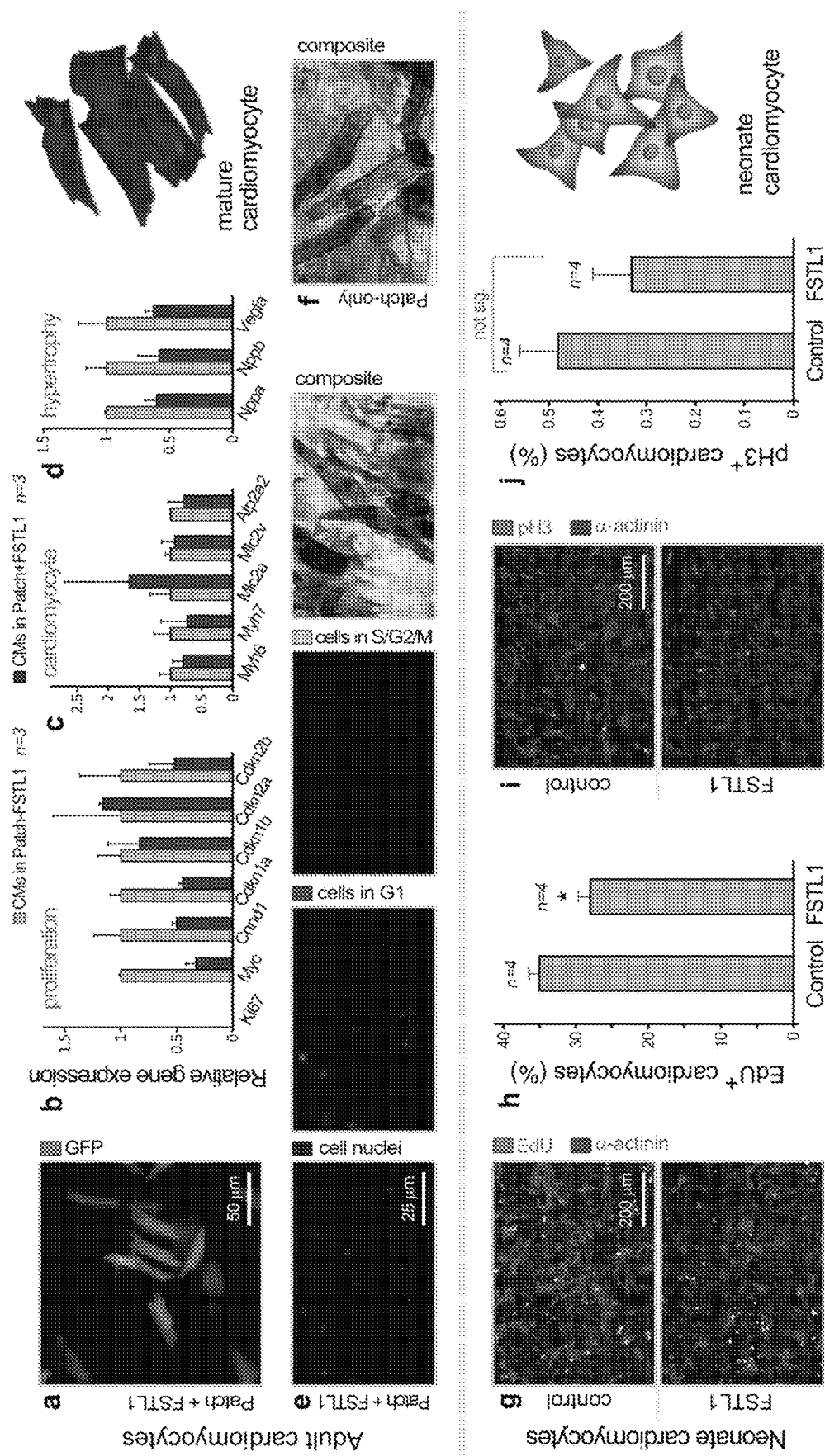
FIG. 18 shows that FSTL1 does not induce proliferation in adult and neonatal cardiomyocytes, or cardiac progenitor cells. a-f) Adult cardiomyocytes derived from mouse primary isolation. a) Visualization of GFP$^+$ cardiomyocytes isolated from MCM$^+$/ZEG$^+$ mice treated with 4-OH-tamoxifen (OH-Tam) in 3D collagen patches. b-d) Gene expression changes in adult cardiomyocyte treated with FSTL1, including proliferation (b), cardiac-specific (c), and hypertrophy (d) markers. Note no changes in expression of cardiac specific genes, no increase in cell cycle markers (consistent with undetectable Ki67 immunostaining), and decreased hypertrophy markers. Cardiomyocytes were embedded within 3D patch were treated with FSTL1 (10 ng/ml) for duration of 7 days with media change every 2 days. e,f) FUCCI assay in 3D-cultured adult cardiomyocytes, conducted 1 week after the 3D culture. e) Treatment with FSTL1 was performed for 7 days with media change every 2 days. f) Adult cardiomyocytes 3D-cultured control in absence of FSTL1. Note no detectable sign of cardiomyocytes in S/G2/M phases (GFP$^+$) in either condition. Purple arrows point to purple-colored nuclei resulting from co-localization of Hoechst (blue) and G1 phase FUCCI (red) labeling. (g-j) Primary neonatal rat ventricular cardiomyocytes (NRVC). g,h) Freshly isolated NRVCs stimulated with FSTL1 for 48 hours with 10 µg/ml EdU, and stained for α-actinin (red) and EdU (green). Percentages of EdU+/α-actinin+cardiomyocytes of all α-actinin+cardiomyocytes are quantified (h). i, j) NRVCs stimulated with FSTL1 for 48 hours, and stained for α-actinin (red) and pH3 (green). Percentages of pH3+/α-actinin+cardiomyocytes of all α-actinin+cardiomyocytes are quantified (j). No increase of proliferation is found upon FSTL1 treatment. (n=4) *: statistically different from control, $P<0.05$. k-m) Sca1$^+$ progenitor cells[19] were starvation-synchronized for 48 hours and stimulated with FSTL1 or control growth medium for 72 hours in presence of EdU. Clone 3 was obtained by clonal growth from the Lin-Sca1$^+$ SP fraction. Sca1 pool was obtained from lin-Sca1$^+$ without clonal growth. k) EdU and DAPI staining of Sca1$^+$ cells after 72 hours treatment. l) Percentage of EdU$^+$ Sca1$^+$ cells after 72 hours treatment. FSTL1 concentration: 0, 1, 10, 100 ng/ml. Abbreviations: SS, serum starvation; CGM, control growth medium. m)

Materials and Methods
Methods use in Example 5 are as described herein.
Results
The patch+FSTL1 cohort showed evidence of $\alpha$-actinin$^+$, striated myocytes within the patch (FIG. 5a-d). Striated cells were rarely observed in the patch in the absence of FSTL1. Importantly, FSTL1 caused a 6.2-fold increase in the incidence of $\alpha$-actinin$^+$ cardiomyocytes that were also positive for phospho-Histone H3(Ser10) (pH3) relative to that seen in the MI-only animals (from 2.5 per cross section (FIG. 5i) in the MI-only to 15.6 per section in MI+Patch+FSTL1 treatment group, p<0.05; FIG. 5e-k and FIG. 16), suggesting that FSTL1 promotes entry into S-phase and DNA replication. Localization to the midbody, which is the transient bridge connecting dividing cells, was confirmed by detection of Aurora B kinase immunoreactivity between $\alpha$-actinin-stained cells and non-overlapping with the nuclear DAPI stain in 3-dimensional reconstructions of confocal optical sections (FIG. 5l), and a significantly increased incidence of cardiomyocytes with midbody-localized Aurora B kinase in MI+Patch+FSTL1 hearts relative to other conditions (FIG. 5 m), which suggests that $\alpha$-actinin$^+$ cells are induced to undergo cytokinesis. Using PCM1 as a marker for cardiomyocyte nuclei[17], a significant increase of incidence of PCM1+ nuclei positive for pH3 was observed (FIG. 5n, o). Increased cardiomyocyte proliferation is also observed 4 weeks after engraftment in patch+FSTL1 treated hearts after FR injury (FIG. 15) There was no effect of FSTL1 on cardiomyocyte apoptosis or area of risk immediately after MI, or apoptosis and inflammation at day 4 and day 8 post-MI (FIG. 17), although FSTL1 has been shown to prevent apoptosis and might modulate inflammation acutely following ischemic injury[12,13,16].

In contrast to patch FSTL1 delivery, the number of pH3$^+$ cardiomyocytes in the border zone myocardium did not increase in FSTL1-TG mice compared to wildtype controls (FIG. 10k,l), despite increased vascularization (FIG. 10m,n and [16]), indicating that epicardial-delivered FSTL1 might have a different function that FSTL1 produced in the myocardium.

Example 6: Origin of the Proliferating FSTL1-Responsive Cardiomyocytes

This Example shows that the glyscosylation status of FSTL1 is linked to changes in its functional status.

Materials and Methods

Neonatal rat ventricular cardiomyocytes (NRVCs) were isolated with the neonatal rat cardiomyocyte isolation kit (Cellutron) and cultured at 37° C. with 5% CO2. In brief, ventricles were dissected from 1-2-d-old Hsd: SD rats (Sprague Dawley), then digested five times for 15 minutes each with the enzyme cocktail at 37° C. Cells were pooled, pre-plated for 90 minutes on an uncoated cell culture dish to remove fibroblasts, and plated on 1% gelatin-coated cell culture plastic dishes in high-serum media (DME/F12 [1:1], 0.2% BSA, 3 mM sodium-pyruvate, 0.1 mM ascorbic acid, 4 mg/liter transferrin, 2 mM L-glutamine, and 5 mg/liter ciprofloxacin supplemented with 10% horse serum and 5% fetal bovine serum (FBS)) at $3 \times 10^5$ cells/cm2. After 24 hours, media was changed to low-serum medium (same but with 0.25% FCS) and cells cultured until use.

Automated In Vitro Cell Proliferation and Cell Death Assay:

Cells (mCMs$^{ESC}$ and NRVC) were incubated with EdU (details of dosage and length of exposure are specified in figure legends) in a 384 plate format, and were fixed for 2 hours in 4% PFA, washed in PBS and stained for EdU using Click-it EdU assay kit (Life Technologies). The cells were then washed in PBS, immunostained with an α-actinin antibody (Sigma, A7811) to identify cardiomyocytes and stained with DAPI (4′,6-diamidino-2-phenylindole) to identify nuclei. The plates were then imaged using InCell 1000 system (GE Healthcare) and automatically analyzed in Developer Toolbox (GE Healthcare) as described[37]. Ratios of EdU+/α-actinin$^+$ nuclei and α-actinin$^+$ nuclei were generated for the percentage of cardiomyocyte incorporated EdU in the chromosomal DNA. Similarly, cells (mCMsESC and NRVC) in 384 plate format were fixed for 2 hours in 4% PFA, washed in PBS, and were immunostained with pH3 antibody (Millipore 06-570) for nuclei in mitosis, or Aurora B (Millipore 04-1036) for cytokinesis, or TUNEL (Roche) for cell death, and α-actinin antibody (Sigma, A7811) for cardiomyocytes and DAPI for nuclei. The same imaging and analysis were done as the EdU assays. The percentages of pH3$^+$, α-actinin$^+$ double positive nuclei, Aurora B$^+$, α-actinin$^+$ double positive cells, and TUNEL$^+$, α-actinin$^+$ double positive nuclei relative to the total number of α-actinin+ cell nuclei were calculated to determine the percentages of cardiomyocytes undergoing mitosis, cytokinesis and apoptosis, respectively.

FSTL1 Overexpression and Western Blot:

Hek293 cells were transiently transfected with human FSTL1 plasmid (GE Dharmacon, ID: ccsbBroad304_02639 pLX304-Blast-V5-FSTL1) using lipofectamine 2000 (mocked transfection was done with lipofectamine and no plasmid). 48 hs post-transfection serum containing media was replaced by serum free DMEM and incubated with the cells for 24 hs. Tunicamycin was used at 2 ug/ml. Conditioned media from tunicamycin samples was collected during 16 hs (cells looked healthy). Conditioned media was spun at 400 g 7 min and then concentrated approximately 20 times using Microcon-10 kDa cut off columns (Millipore). Samples were combined 1 to 1 ratio with 2×SDS sample buffer containing protease inhibitor, DTT and 5 mM EDTA, boiled 10 minutes at 95 C and run in a 4-15% acrylamide Mini-Protean TGX gel, transferred to nitrocellulose membrane and incubated with anti-V5 primary antibody MAB 15253 (Pierce) 1:1,000 dilution and anti-mouse 800 nm conjugated secondary antibody at 1:10,000 dilution (Odyssey). Neonatal rat ventricular cardiomyocytes were infected with adenovirus expressing un-tagged mouse FSTL1 at MOI 50. 24 hs postinfection culture media was replaced by serum free media. Serum free DMEM/F12 pen/strep media was conditioned with the infected NRVC and EMC cells for 24 hs. Tunicamycin was used at 1 ug/ml and media was conditioned for 16 hrs. Conditioned media was spun at 400 g 7 minutes and then concentrated using Microcon-10 kDa cut off columns (Millipore). Samples were combined 1 to 1 ratio with 2×SDS sample buffer containing protease inhibitor, DTT and 5 mM EDTA, boiled 10 minutes at 95 C and run in Any KD Mini-Protean TGX gel, transferred to nitrocellulose membrane and incubated with anti-FSTL1 MAB1694 (R&D) primary antibody 1:500 dilution and anti-rat 800 nm conjugated secondary antibody at 1:10,000 dilution (Odyssey). Blocking and antibody incubation was done in Odyssey blocker. The western blot for recombinant FSTL1 (100 ng each) was performed the same way.

Cardiomyocyte Lineage Labelling:

Cardiomyocyte lineage labelling was achieved by injecting 4-OH tamoxifen intraperitoneally into eight-week old Myh6$^{mERcremER}$:Rosa26$^{Z/EG}$ mice[18] of C57BL6 background at a dose of 20 mg per kg per day for 2 weeks, and stopped 1 week before harvesting cardiomyocytes (FIG. 5p), or MI operation and patch grafting. 4 weeks after MI, the animals were collect for immunostaining (FIG. 5q-u).

Results

In vivo, the cardiomyocytes induced by FSTL1 to enter into cell cycle might arise from pre-existing myocytes (Myh6$^+$ cells) or de novo from a progenitor population. To distinguish between these possibilities, pre-existing Myh6$^+$ cardiomyocytes were heritably labeled using a tamoxifen-inducible Cre under the control of the cardiomyocyte-specific Myh6 promoter[18] and their fate followed after MI and patch+FSTL1 engraftment (FIG. 5p). 4-OH tamoxifen injected into Myh6$^{mERCremER}$: Rosa26$^{Z/EG}$ mice efficiently labeled pre-existing cardiomyocytes with eGFP prior to MI (FIG. 5q). Four weeks after patch engraftment, eGFP$^+$, pH3$^+$ cells were clearly visible in the infarct area and border zone (FIG. 5r-u), indicating that the patch+FSTL1 acts on cells that expressed Myh6 prior to LAD ligation and patch engraftment.

What is the source of the cycling α-actinin$^+$ cells? Adult cardiomyocytes are generally refractory to cell cycle entry, and FSTL1 did not promote DNA replication or cell division of adult or neonatal murine ventricular cardiomyocytes in vitro (FIG. 18a-j). Similarly, FSTL1 did not stimulate proliferation or differentiation of clonally expanded primary cardiomyogenic progenitor cells (Lin$^-$, Sca1$^+$, SP$^+$) from the adult murine heart that can form cardiomyocytes upon re-implantation into the adult heart[19] (FIG. 18k-m). In contrast, mCMs$^{ESC}$ cells responded to FSTL1 in a dose dependent manner by increased incorporation of 5-ethynyl-2′-deoxyuridine (EdU) in α-actinin+mCMsESC (FIG. 6a,d), increased number of pH3$^+$, α-actinin$^+$ cells (FIG. 6b,e) and cleavage-furrow/midbody localized Aurora B kinase (FIG. 6c,f). These results, combining with the lineage tracing results showing Myh6$^+$ cells proliferating in vivo after patch+FSTL1 treatment (FIG. 5 p-u), suggest the existence of Myh6$^+$/α-actinin$^+$ cells, located proximal to the epicardium, that are proliferation-competent in response to epicardial FSTL1.

Figure 4:
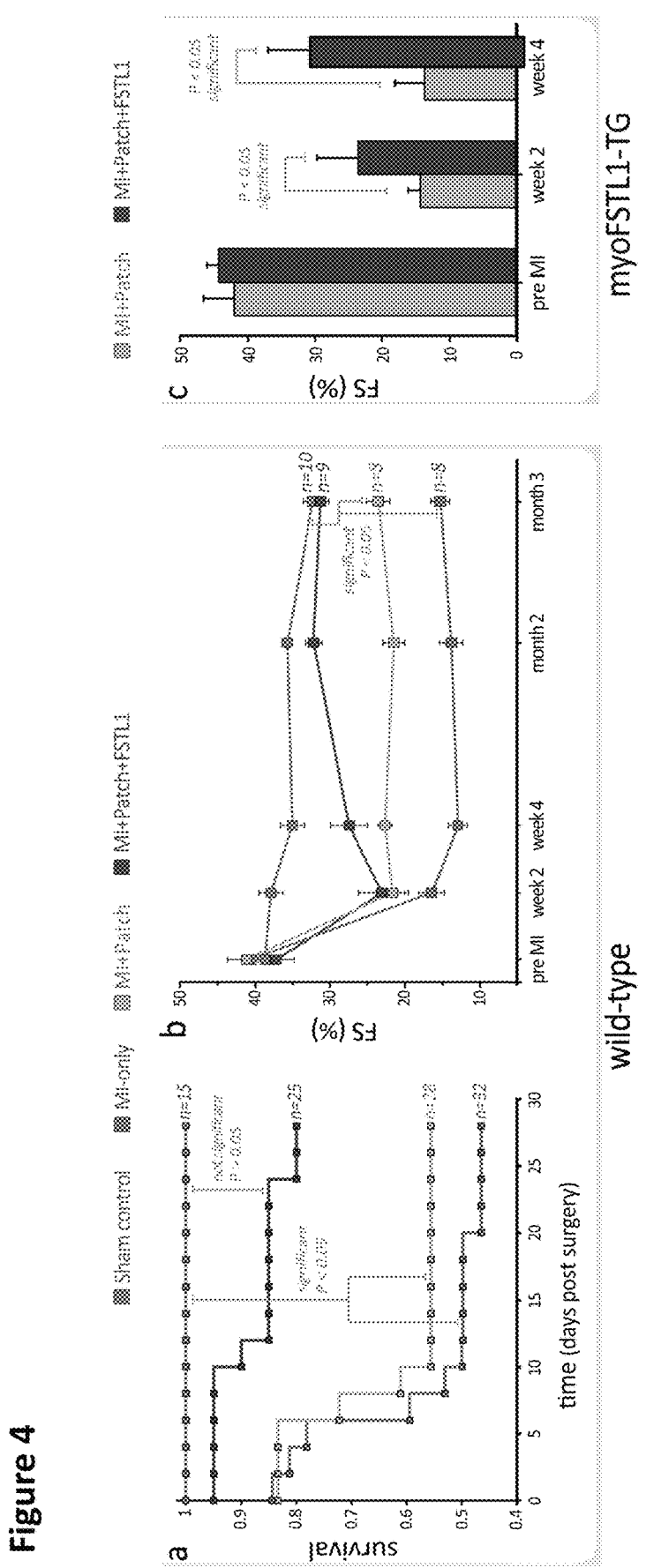
FIG. 4 depicts that FSTL1 recapitulates the in vivo restorative effect of epicardial conditioned-media in the engineered epicardial patch. a-c) Physiological analysis. a) Survival time course of each condition was analyzed using the Kaplan-Meier method. b) Kinetics of fractional shortening [FS (%)] as measured by echocardiography during the first 3 months of the indicated treatments. Data provided as absolute values of FS: sham (Sham control), infarcted mice without treatment (MI-only), MI treated with patch-only (MI+Patch), and infarcted animals treated with patch laden with FSTL1 (MI+Patch+FSTL1). c) FS % at 2 and 4 weeks post-MI in FSTL1-TG mice comparing MI+Patch and MI+Patch+FSTL1*: p<0.05 compared to Sham control, ●: p<0.05 compared to MI-only, and ■: p<0.05 compared to MI+Patch. d-e) Morphometric analysis. d) Representative Masson's trichrome staining of hearts 4 weeks post MI and quantification of the fibrotic area as a percentage of total LV wall (n>4). e) Echocardiography evaluation of left ventricular morphology. Abbreviations indicate: LVIDd (left ventricular internal diameter in end diastole); LVIDs (left ventricular internal diameter in end systole); LVPWd (left ventricular posterior wall dimension in end diastole); LVPWs (left ventricular posterior wall thickness in systole). *: p<0.05 compared to sham, ●: p<0.05 compared to MI-only, and ■: p<0.05 compared to MI+Patch. f-i) Analysis of the vasculature at week 4 post MI. f) Immunostaining for an endothelial marker (vWF). g) Vessel area quantified by measuring mean lumen area of individual vessels relative to overall area of histological sections. h) Immunostaining for a smooth muscle marker (αSMA). 1) Quantification of the number of vessels per area unit. *: p<0.05 compared to Sham control, ●: p<0.05 compared to MI-only, and ■: p<0.05 compared to MI+Patch. j) Visualization of patch-border zone at week 4 post MI. Trichrome staining of infarct and border zone of the indicated treatments demonstrates the integration of the patch with the host tissue and massive patch cellularization by the native cardiac cells. Observe the abundant muscle (red) inside the patch and in the border zone of the patch+FSTL1 treated animals (three right panels, green arrowheads).
Figure 6:
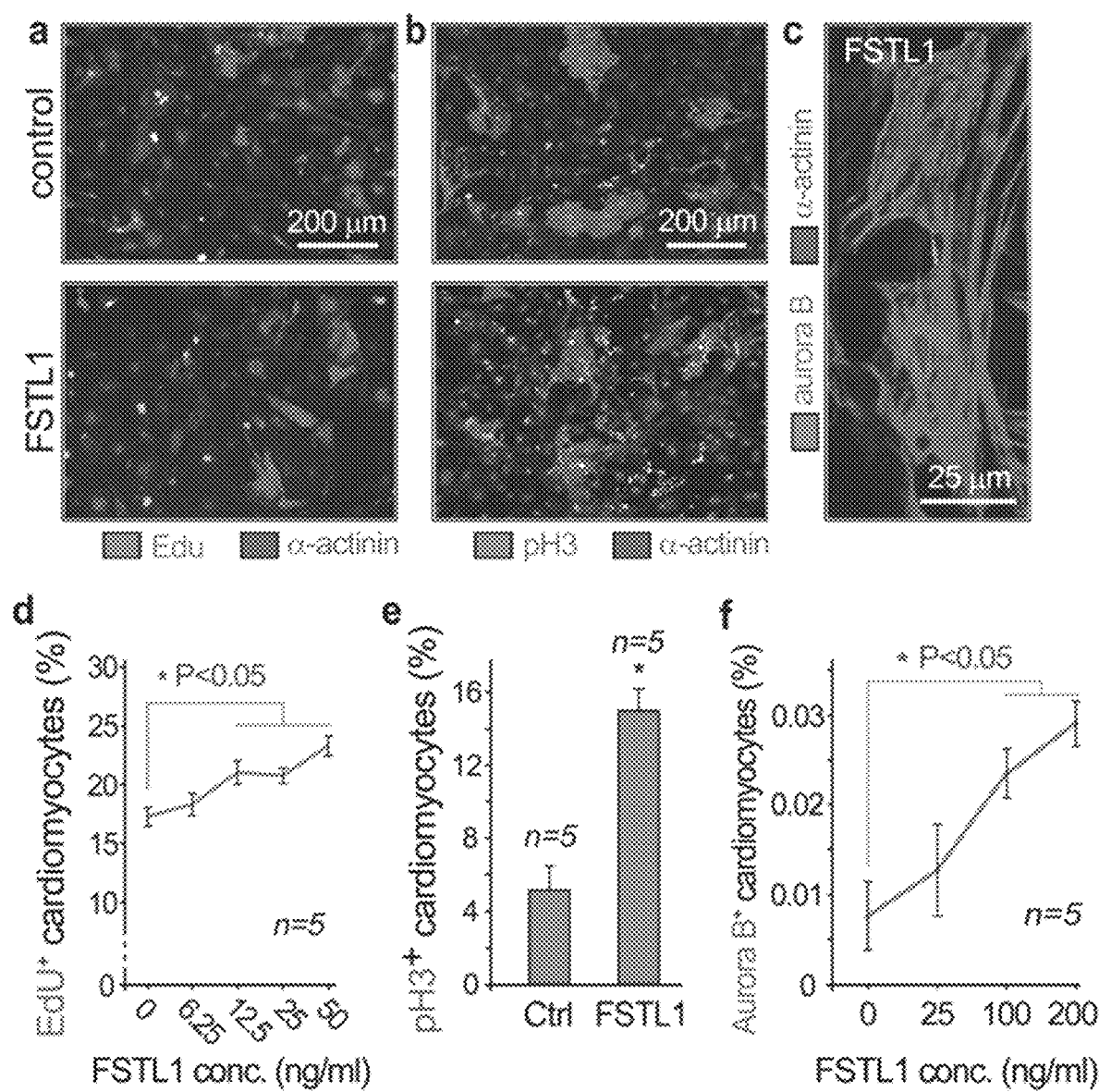
FIG. 6 depicts FSTL1 proliferative activity on early cardiomyocytes depends on cells-selective post-transcriptional FSTL1 modifications. a-f) FSTL1 promotes proliferation of Immature cardiomyocytes derived from mESCs. a, d) mCMs$^{ESC}$ were stimulated with indicated concentration of FSTL1 for 24 hours with 10 μg/ml EdU, and stained for α-actinin (red) and EdU (green). Percentages of EdU+, α-actinin+ cardiomyocytes of all α-actinin+ cardiomyocytes are quantified (d). b, e) mCMs$^{ESC}$ were stimulated with 10 ng/ml FSTL1 for 48 hours and stained for α-actinin (red) and phospho-Histone3 (green). Percentages of pH3+, α-actinin+ cardiomyocytes of all α-actinin+ cardiomyocytes are quantified (e). c, f) mCMsESC are stimulated with indicated concentration of FSTL1 for 48 hours, and stained for α-actinin (red) and cytokinesis marker Aurora B (green). Percentages of Aurora B+, α-actinin$^+$ cardiomyocytes of all α-actinin$^+$ cardiomyocytes are quantified (f). g, h) FSTL1 expressed in mammalian cells are glycosylated g) Western blot against FSTL1 of conditioned media of HEK293 cells+/−FSTL1 overexpression, and +/−Tunicamycin (Tuni.) blocking protein glycosylation, showing FSTL1 is glycosylated. h) Western blot against FSTL1 of recombinant human FSTL1 expressed in mammalian cells or in bacteria, showing differences in glycosylation (red arrow: glycosylated form; black arrow: unglycosylated form). i) mCMs$^{ESC}$ are stimulated with 10 nM H$_2$O$_2$, and 10 ng/ml bacteria and mammalian produced FSTL1 for 24 hours, and staining for α-actinin and TUNEL for cell death. Percentages of TUNEL$^{+}$ α-actinin$^+$ cardiomyocytes of all α-actinin$^+$ cardiomyocytes are quantified (i), showing mammalian-produced FSTL1 is able to attenuate H$_2$O$_2$ induced apoptosis, while bacterial-produced FSTL1 cannot, while both proteins have no effect on apoptosis without H$_2$O$_2$ stimulation. j, k) EdU incorporate and Aurora B quantification (the same assay as a, c, d, f) comparing bacteria and mammalian produced FSTL1, showing bacterial-produced FSTL1 promotes mcMs$^{ESC}$ proliferation, while mammalian-produced FSTL1 cannot. 1) FSTL1 is differentially glycosylated in cardiomyocytes and epicardial cells. Western blot against FSTL1 of conditioned media of NRVC infected with Adeno-FSTL1 and conditioned media of EMC, treated with or without Tunicamycin, showing unglycosylated protein with the same size while glycosylated FSTL1 with different sizes, suggesting cardiomyocytes and epicardial cells modify FSTL1 differently. m, n) EdU incorporation assay comparing the effect of conditioned media of NRVC infected with Adeno-FSTL1 and conditioned media of EMC. Normalized to the same amount of FSTL1 concentration using western blot, EMC conditioned media induced mCMs$^{ESC}$ proliferation to similar extent to bacterial-produced FSTL1, while conditioned media of NRVC infected with Adeno-FSTL1 cannot, suggesting glycosylation status determines the function of FSTL1. n=5 for all experiments. *: statistically different from control, P<0.05. o) Actions of FSTL1 during cardiac injury, working model. In ischemic heart disease FSTL1 becomes very highly expressed in the myocardium. Myocardial-secreted FSTL1 is highly glycosylated (glycoFSTL1) and protects from apoptosis, and does not display proliferative activity. FSTL1 is not expressed in the epicardium of the injured heart The hypo-glycosylated form, either secreted by the intact epicardium or delivered in the epicardial patch, activates proliferation in replication-competent cardiomyocyte precursor cells, located in the subepicardial space.

It remained paradoxical, however, that neither the endogenous myocardial induction of FSTL1 expression, nor direct transgenic over-expression of FSTL1 could activate regeneration (FIG. 4, FIG. 10). Thus, whether cell-specific modifications of FSTL1 could be involved, particularly important as all of our previous experiments were performed using bacterial-synthesized human FSTL1 was tested (FIGS. 4, 5, 6a-f). FSTL1 is highly glycosylated in mammalian cells (FIG. 6g), whereas the recombinant FSTL1 produced in bacteria is not (FIG. 6h). The function of recombinant FSTL1 produced in bacterial (naked) and mammalian cells (glycosylated) was therefore tested in apoptosis and proliferation assays on mCMs$^{ESC}$ cells. Mammalian expressed human FSTL1 protects mCMs$^{ESC}$ from $H_2O_2$ induced apoptosis whereas bacterial expressed FSTL1 does not (FIG. 6 i). Conversely, bacterial-expressed human FSTL1 promotes mCMs$^{ESC}$ proliferation, whereas mammalian-expressed human FSTL1 does not (FIG. 6 j, k), thus, these key functional differences correlate with FSTL1 glycosylation status. It was also compared whether overexpressed FSTL1 in neonatal rat ventricular cardiomyocytes (NRVC)—NRVCs do not produce detectable amount of endogenous FSTL1 (FIG. 19)—with endogenous FSTL1 expressed in EMC-epicardial cells. Western-blot analysis indicated significant size differences between the myocardial and epicardial forms of FSTL1, differences that "disappear" with tunicamycin treatment (inhibitor of glycosylation) (FIG. 6 i), suggesting that FSTL1 is post-transcriptionally modified (glycosylated) in a cell-specific manner. Subsequently, these Fstl forms produced in myocardial and epicardial cells were functionally tested in the proliferation assay on mCMs$^{ESC}$. Myocardial conditioned media from NRVC infected with an untagged FSTL1 Adeno-virus showed no effect on mCMsESC proliferation. In contrast EMC conditioned media significantly promoted mCMs$^{ESC}$ proliferation in a hypoglycosylated FSTL1-dependent manner (FIG. 6 m, n) to an extent comparable to the bacterial-synthesized hFSTL1, demonstrating that cell specific posttranscriptional modifications are linked to changes in FSTL1 functional status.

Example 7: Epicardial FSTL1 Delivery Activates Cardiac Regeneration in a Preclinical Swine Model This Example shows that the restorative effect of patch+FSTL1 delivery in the epicardium seems evolutionarily conserved.

Materials and Methods

Application of the Patch in a Swine Model of Ischemia-Reperfusion:

The swine study was performed by inflation of a percutaneous coronary angioplasty dilation catheter to occlude the LAD in Yorkshire pigs (45 days old). Occlusion time of 90 mins was followed by fully reperfusion to mimic the clinical MI disease model. One week after MI, a left thoracotomy was performed and the patch was sutured onto the infarct. Animal groups included: sham controls, FR with no treatment (n=3), FR treated with patch alone (I/R+Patch, n=1), and FR treated with patch laden with FSTL1 (I/R+Patch+FSTL1, n=2). EdU delivery: 250 mg/week EdU was infused into circulation during the 4-week time course of study (week 1 to week 5 post FR), using osmotic mini pumps.

Statistical Analysis:

The number of samples (n) used in this and all other Examples is recorded in the text and shown in figures. All in vitro experiments have been done at least twice independently. Gene expression experiments have been done 3 times independently and EdU proliferation assays and cell size measurement have been done more than 10 times independently. Sample size was not predetermined, with retrospective analysis of significantly different results in most in vitro studies using Gpower 3.1 produces power>0.8. Sample sizes for animal studies were estimated. Animals which did not survive up to 4 weeks after surgery were excluded from functional and histological studies. Randomization was not applied. Blinding to group allocation was practiced between animals surgery and results analysis of mouse myocardial infarction experiments. The values presented are expressed as means±SEM. The rationale to use means±SEM instead of SD is that SEM quantifies uncertainty in an estimate of the mean whereas SD indicates dispersion of the data from mean. In other words, the SEM provides an estimate of the reported mean value, while the SD gives an idea of the variability of single observations. One-way ANOVA and student T-test were used to test for statistical significance ($P<0.05$). Survival curve were generated using PRISM (GraphPad) and Log-rank (Mantel-Cox) test was used to test the significant differences between the survival of mice in different conditions.

Results

Figure 7:
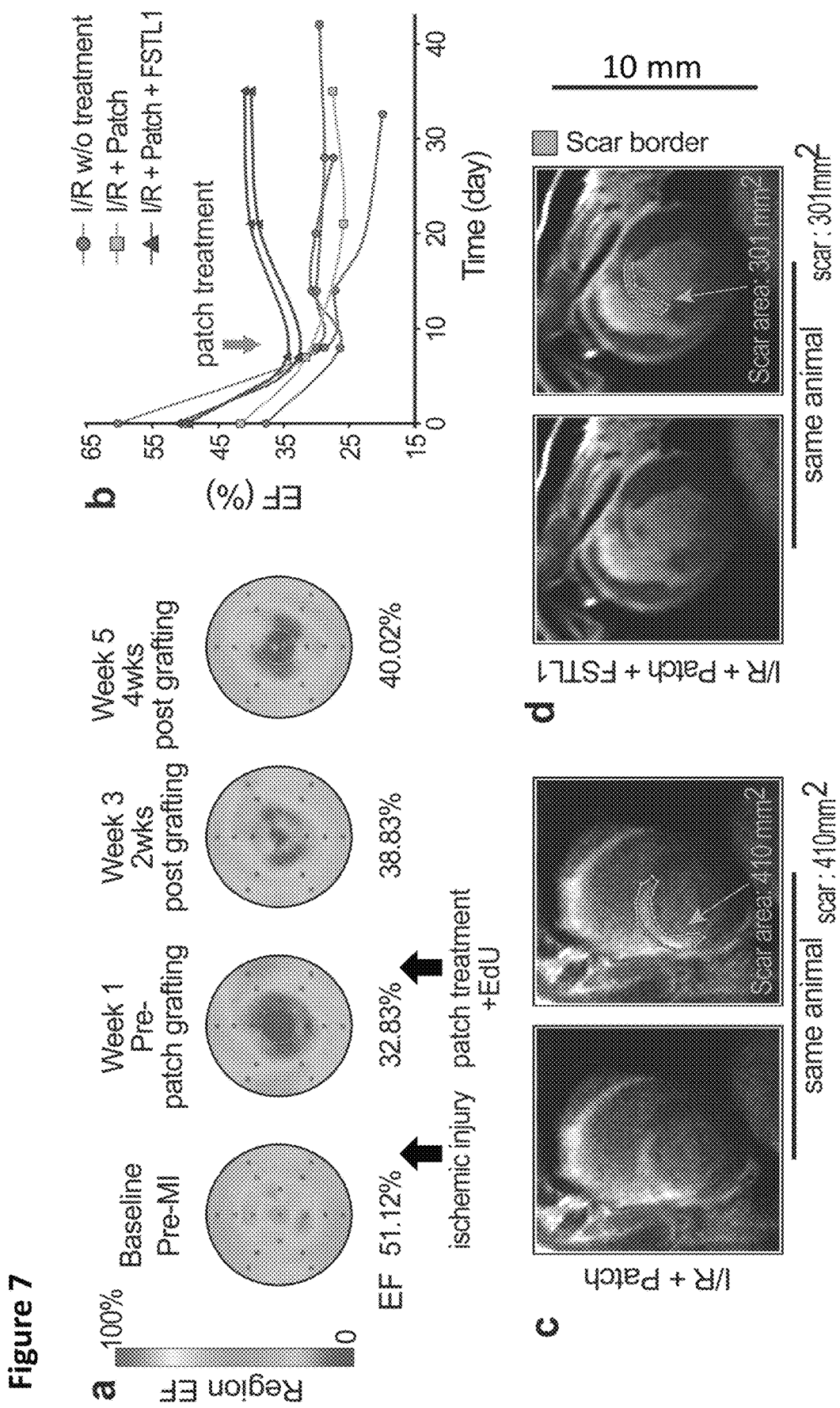
FIG. 7 depicts that Epicardial FSTL1 delivery activates cardiac regeneration in preclinical model of ischemic heart injury. a-d) Physiological effect of FSTL1 patch-delivery into the epicardium in the swine experimental model of ischemia reperfusion (FR). MIII measured a baseline ejection fraction (EF) ~50% that decreased after one week to ~30% (a-b). Pigs treated with Patch+FSTL1 one week after FR recovered contractility by 2 weeks of the treatment, with EF of ~40%. EF remained stable by the following 2 weeks, the longest time analyzed (a,b). This was in contrast to the steady decay of heart function in untreated animals (FR w/o treatment) or in the animal treated with patch alone (I/R+Patch) (b). c-d): Patch+FSTL1 treated pigs (c) demonstrated the smallest scar size (area) in all study groups including FR+Patch animal (d). The green lines and arrows highlight the scar perimeter. e-o) Evaluation of patch integration with the host cardiac tissue, angiogenesis, and cellularization and regeneration at week 4 post implantation. e) Masson's trichrome staining of the pig heart demonstrated Patch+FSTL1 attachment to the ischemic tissue and limited fibrosis. f-h) Immunostaining of smooth muscle marker (αSMA, red) and EdU (green) showing newly formed arterial smooth muscles. Pig hearts treated with Patch+FSTL1 showed evidences of new DNA formation in the vascular smooth muscle cells in the both ischemic area (f, g) and in the border zone with the patch laden with FSTL1 (h). The white line and arrow in panel h demarcate the approximate border of the patch with the host tissue. i-m) EdU incorporation analysis of cardiomyocytes residing in the infarct and border zone in pig hearts treated with Patch+FSTL1, demonstrating striated cardiomyoctes (aactinin+, red) some of which (arrows in 1) also stained positive for DNA synthesis (EdU, green, examples in high magnification in j-m). n) Co-immunofluorescence of cardiomyocytes (α-actinin, green) and the cytokinesis marker Aurora B kinase (red) in the patch+FSTL1 heart, with 3D rendering showing Aurora B kinase$^+$ midbody between α-actinin$^+$ cardiomyocytes in the Z axis.

The engineered epicardial delivery of FSTL1 was evaluated in the swine model of myocardial ischemia-reperfusion injury. Prior to infarction, ejection fraction (EF) was ~50% as determined by magnetic resonance imaging (MRI). One week after FR, EF % decreased to ~30%, after which patch+FSTL1 was applied to the epicardium of the injured tissue. Pigs treated with patch+FSTL1 recovered contractility by week 2 of treatment (week 3 of the experiment), achieving an EF of approximately 40%, and remained stable for 2 weeks, the longest time analyzed (FIG. 7a, b). This was in contrast to the steady decline of heart function in untreated animals and in the animal treated with patch alone (FIG. 7b). Patch+FSTL1 treated pigs demonstrated the lowest content in fibrotic tissue formation (scar size) of all treatments, including patch-only animal (see representative MRI images (FIG. 7c, d). Pig tissues, analyzed at week 4 post patch grafting (week 5 of the experiment), showed integration of the patch into the host tissue and limited fibrosis (FIG. 7e) and EdU labeling of vascular smooth muscle cells (FIG. 7f-h) and cardiomyocytes (FIG. 7i-m) in the border zone of ischemic area. Cardiomyocytes with midbody-localized Aurora B kinase (indicative of cytokinesis) were also detected in the border zone of the Patch+FSTL1 treated heart (FIG. 7n). Thus, the restorative effect of patch+FSTL1 delivery in the epicardium seems evolutionarily conserved.

Example 8: Administration of Hypoglycosylated FSTL1 does not Activate Akt-1 Signaling Activity This Example shows that FSTL1 treatment of mCMs$^{ESC}$ did not result in activation of Akt-1.

Treatment of mCMs$^{ESC}$ with FSTL1 as well as Western blot for phosphor-Akt were performed as described above.

The results are shown in FIG. 20 which depicts phosphor-Akt and PCNA detections in mCMs$^{ESC}$ after FSTL1 treatment. Western blot against phosphor-Akt (Ser473 and Thr308, both involved in survival response in cardiomyocytes) and PCNA (proliferation marker) after 1 hour and 24 hours of FSTL1 treatment at 10 ng/ml and 50 ng/ml, resulted in no significant change in either phosphor-Akt or PCNA upon FSTL1 treatment.

REFERENCES

1. Van Wijk, B., Gunst, Q. D., Moorman, A. F. & van den Hoff, M. J. Cardiac regeneration from activated epicardium. *PLoS One* 7, e44692, doi:10.1371/journal.pone.0044692 (2012).
2. Cai, C. L. et al. A myocardial lineage derives from Tbx18 epicardial cells. *Nature* 454, 104-108, doi:10.1038/nature06969 (2008).

3. Lavine, K. J. & Ornitz, D. M. Rebuilding the coronary vasculature: hedgehog as a new candidate for pharmacologic revascularization. *Trends in cardiovascular medicine* 17, 77-83, doi:10.1016/j.tcm.2007.01.002 (2007).
4. Brade, T. et al. Retinoic acid stimulates myocardial expansion by induction of hepatic erythropoietin which activates epicardial Igf2. *Development* 138, 139-148, doi: 138/1/139 [pii] 10.1242/dev.054239 (2011).
5. Mellgren, A. M. et al. Platelet-derived growth factor receptor beta signaling is required for efficient epicardial cell migration and development of two distinct coronary vascular smooth muscle cell populations. *Circ Res* 103, 1393-1401, doi:10.1161/CIRCRESAHA. 108.176768 (2008).
6. Smart, N. et al. Myocardial regeneration: expanding the repertoire of thymosin beta4 in the ischemic heart. *Ann N Y Acad Sci* 1269, 92-101, doi:10.1111/j.1749-6632.2012.06708.x (2012).
7. Kikuchi, K. et al. tcf21+ epicardial cells adopt non-myocardial fates during zebrafish heartdevelopment and regeneration. Development 138, 2895-2902, doi:10.1242/dev.067041 (2011).
8. Mercola, M., Ruiz-Lozano, P. & Schneider, M. D. Cardiac muscle regeneration: lessons from development. *Genes & development* 25, 299-309, doi:10.1101/gad.2018411 (2011).
9. Zhou, B. et al. Adult mouse epicardium modulates myocardial injury by secreting paracrine factors. *J Clin Invest* 121, 1894-1904, doi:10.1172/JCI45529 (2011).
10. Serpooshan, V. et al. The effect of bioengineered acellular collagen patch on cardiac remodeling and ventricular function post myocardial infarction. *Biomaterials* 34, 9048-9055, doi:10.1016/j.biomaterials.2013.08.017 (2013).
11. Tanaka, M. et al. DIP2 disco-interacting protein 2 homolog A (*Drosophila*) is a candidate receptor for follistatin-related protein/follistatin-like 1-analysis of their binding with TGFbeta superfamily proteins. *The FEBS journal* 277, 4278-4289, doi:10.1111/j.1742-4658.2010.07816.x (2010).
12. Oshima, Y. et al. Follistatin-Like 1 Is an Akt-Regulated Cardioprotective Factor That Is Secreted by the Heart. *Circulation* 117, 3099-3108, doi:10.1161/circulationaha.108.767673 (2008).
13. Ogura, Y. et al. Therapeutic impact of follistatin-like 1 on myocardial ischemic injury in preclinical models. *Circulation* 126, 1728-1738, doi:10.1161/CIRCULATIONAHA.112.115089 (2012).
14. Widera, C. et al. Identification of Follistatin-Like 1 by Expression Cloning as an Activator of the Growth Differentiation Factor 15 Gene and a Prognostic Biomarker in Acute Coronary Syndrome. *Clinical chemistry*, doi: 10.1373/clinchem. 2012.182816 (2012).
15. Adams, D., Larman, B. & Oxburgh, L. Developmental expression of mouse Follistatin-like 1 (FSTL1): Dynamic regulation during organogenesis of the kidney and lung. *Gene Expression Patterns* 7, 491-500 (2007).
16. Shimano, M. et al. Cardiac myocyte follistatin-like 1 functions to attenuate hypertrophy following pressure overload. *Proceedings of the National Academy of Sciences of the United States of America* 108, E899-906, doi:10.1073/pnas.1108559108 (2011).
17. Bergmann, O. et al. Identification of cardiomyocyte nuclei and assessment of ploidy for the analysis of cell turnover. *Experimental Cell Research* 317, 188-194, doi: http://dx.doi.org/10.1016/j.yexcr.2010.08.017 (2011).
18. Sohal, D. S. et al. Temporally regulated and tissue-specific gene manipulations in the adult and embryonic heart using a tamoxifen-inducible Cre protein. *Circ Res* 89, 20-25 (2001).
19. Oh, H. et al. Cardiac progenitor cells from adult myocardium: homing, differentiation, and fusion after infarction. *Proceedings of the National Academy of Sciences of the United States of America* 100, 12313-12318 (2003).
20. Ouchi, N. et al. Follistatin-like 1, a Secreted Muscle Protein, Promotes Endothelial Cell Function and Revascularization in Ischemic Tissue through a Nitric-oxide Synthase dependent Mechanism. *Journal of Biological Chemistry* 283, 32802-32811, doi:10.1074/jbc.M803440200 (2008).
21. Chong, J. J. et al. Adult cardiac-resident MSC-like stem cells with a proepicardial origin. *Cell Stem Cell* 9, 527-540, doi:10.1016/j.stem.2011.10.002 (2011).
22. Smart, N. et al. De novo cardiomyocytes from within the activated adult heart after injury. *Nature*, doi:nature10188 [pii] 10.1038/nature10188 (2011).
23. Limana, F. et al. Identification of myocardial and vascular precursor cells in human and mouse epicardium. *Circ Res* 101, 1255-1265, doi:CIRCRESAHA.107.150755 [pii] 10.1161/CIRCRESAHA.107.150755 (2007).
24. Masters, M. & Riley, P. R. The epicardium signals the way towards heart regeneration. *Stem cell research*, doi: 10.1016/j.scr.2014.04.007 (2014).
25. Bersell, K., Arab, S., Haring, B. & Kuhn, B. Neuregulin1/ErbB4 signaling induces cardiomyocyte proliferation and repair of heart injury. *Cell* 138, 257-270, doi:50092-8674(09)00522-4 [pii] 10.1016/j.cell.2009.04.060 (2009).
26. Chen, H. S., Kim, C. & Mercola, M. Electrophysiological challenges of cell-based myocardial repair. *Circulation* 120, 2496-2508, doi:120/24/2496 [pii] 10.1161/CIRCULATIONAHA.107.751412 (2010).
27. Senyo, S. E. et al. Mammalian heart renewal by pre-existing cardiomyocytes. *Nature* 493, 433-436, doi: 10.1038/nature11682 (2013).
28. Zhang, Y. et al. Dedifferentiation and proliferation of mammalian cardiomyocytes. *PLoS ONE* 5, e12559, doi: 10.1371/journal.pone.0012559 (2010).
29. Jopling, C. et al. Zebrafish heart regeneration occurs by cardiomyocyte dedifferentiation and proliferation. *Nature* 464, 606-609, doi:10.1038/nature08899 (2010).
30. Brown, R. A., Wiseman, M., Chuo, C. B., Cheema, U. & Nazhat, S. N. Ultrarapid engineering of biomimetic materials and tissues: Fabrication of nano- and microstructures by plastic compression. *Adv Funct Mater* 15, 1762-1770, doi:DOI 10.1002/adfm.200500042 (2005).
31. Venugopal, J. R. et al. Biomaterial strategies for alleviation of myocardial infarction. *J R Soc Interface* 9, 1-19, doi:10.1098/rsif.2011.0301 (2012).
32. Engler, A. J. et al. Embryonic cardiomyocytes beat best on a matrix with heart-like elasticity: scar-like rigidity inhibits beating. *J Cell Sci* 121, 3794-3802, doi:10.1242/jcs.029678 (2008).
33. Eid, H. et al. Role of epicardial mesothelial cells in the modification of phenotype and function of adult rat ventricular myocytes in primary coculture. *Circ Res* 71, 40-50 (1992).
34. Kita-Matsuo, H. et al. Lentiviral vectors and protocols for creation of stable hESC lines for fluorescent tracking and drug resistance selection of cardiomyocytes. *PLoS ONE* 4, e5046, doi:10.1371/journal.pone.0005046 (2009).

35. Fajardo, G. et al. Deletion of the beta2-adrenergic receptor prevents the development of cardiomyopathy in mice. *J Mol Cell Cardiol* 63, 155-164, doi:10.1016/j.yjmcc.2013.07.016 S0022-2828(13)00249-6 [pii] (2013).
36. Sakaue-Sawano, A. et al. Visualizing spatiotemporal dynamics of multicellular cell-cycle progression. *Cell* 132, 487-498, doi:10.1016/j.cell.2007.12.033 S0092-8674(08)00054-8 [pii] (2008).
37. Bushway, P. J. & Mercola, M. High-throughput screening for modulators of stem cell differentiation. *Methods Enzymol* 414, 300-316, doi:S0076-6879(06)14017-3 [pii] 10.1016/S0076-6879(06)14017-3 (2006).
38. Cerignoli, F. et al. High Throughput Drug Risk Assessment in Human Cardiomyocytes by Kinetic Image Cytometry. *Submitted (J. Pharm. Toxicol. Methods)* (2012).
39. Serpooshan, V. et al. Reduced hydraulic permeability of three-dimensional collagen scaffolds attenuates gel contraction and promotes the growth and differentiation of mesenchymal stem cells. *Acta Biomater* 6, 3978-3987, doi:S1742-7061(10)00217-5 [pii] 10.1016/j.actbio.2010.04.028 (2010).
40. Serpooshan, V., Muja, N., Marelli, B. & Nazhat, S. N. Fibroblast contractility and growth in plastic compressed collagen gel scaffolds with microstructures correlated with hydraulic permeability. *J Biomed Mater Res A* 96, 609-620, doi:10.1002/jbm.a.33008 (2011).
41. Abou Neel, E. A., Cheema, U., Knowles, J. C., Brown, R. A. & Nazhat, S. N. Use of multiple unconfined compression for control of collagen gel scaffold density and mechanical properties. *Soft Matter* 2, 986-992, doi: Doi 10.1039/B609784g (2006).
42. Clement, S. et al. Expression and function of alpha-smooth muscle actin during embryonic stem-cell-derived cardiomyocyte differentiation. *J Cell Sci* 120, 229-238, doi:jcs.03340 [pii] 10.1242/jcs.03340 (2007).

---

SEQUENCE LISTING

```
<160> NUMBER OF SEQ ID NOS: 34

<210> SEQ ID NO 1
<211> LENGTH: 308
<212> TYPE: PRT
<213> ORGANISM: Homo sapiens

<400> SEQUENCE: 1

Met Trp Lys Arg Trp Leu Ala Leu Ala Leu Val Ala Val Ala
1               5                   10                  15

Trp Val Arg Ala Glu Glu Glu Leu Arg Ser Lys Ser Lys Ile Cys Ala
                20                  25                  30

Asn Val Phe Cys Gly Ala Gly Arg Glu Cys Ala Val Thr Glu Lys Gly
            35                  40                  45

Glu Pro Thr Cys Leu Cys Ile Glu Gln Cys Lys Pro His Lys Arg Pro
        50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Ile Ile Gln Trp
        115                 120                 125

Leu Glu Ala Glu Ile Ile Pro Asp Gly Trp Phe Ser Lys Gly Ser Asn
130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
    210                 215                 220

Ser Phe Asn Pro Pro Glu Lys Lys Cys Ala Leu Glu Asp Glu Thr Tyr
225                 230                 235                 240
```

```
Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Glu Met Thr Arg Tyr Val Gln
        275                 280                 285

Glu Leu Gln Lys His Gln Thr Ala Glu Lys Thr Lys Arg Val Ser
    290                 295                 300

Thr Lys Glu Ile
305

<210> SEQ ID NO 2
<211> LENGTH: 3837
<212> TYPE: DNA
<213> ORGANISM: Artificial Sequence
<220> FEATURE:
<223> OTHER INFORMATION: Synthetic construct

<400> SEQUENCE: 2
aggagaatgg ggaggagctg ggggggcagg caggcgggga aggagaggtc ttaaggggcg      60
gcgaggggag gtcgcatttc ctccgaggct ggcgatcggc ggagctccca cctccgctta    120
cagctcgctg ccgccgtcct gccccgcgcc cccaggagac ctggaccaga ccacgatgtg    180
gaaacgctgg ctcgcgctcg cgctcgcgct ggtggcggtc gcctgggtcc gcgccgagga    240
agagctaagg agcaaatcca agatctgtgc caatgtgttt tgtggagccg gccgggaatg    300
tgcagtcaca gagaaagggg aacccacctg tctctgcatt gagcaatgca aacctcacaa    360
gaggcctgtg tgtggcagta atggcaagac ctacctcaac cactgtgaac tgcatcgaga    420
tgcctgcctc actggatcca aaatccaggt tgattacgat ggacactgca agagaagaa    480 atccgtaagt ccatctgcca gcccagttgt ttgctatcag tccaaccgtg atgagctccg    540
acgtcgcatc atccagtggc tggaagctga gatcattcca gatggctggt tctctaaagg    600
cagcaactac agtgaaatcc tagacaagta ttttaagaac tttgataatg gtgattctcg    660
cctggactcc agtgaattcc tgaagtttgt ggaacagaat gaaactgcca tcaatattac    720
aacgtatcca gaccaggaga acaacaagtt gcttagggga ctctgtgttg atgctctcat    780
tgaactgtct gatgaaaatg ctgattggaa actcagcttc caagagtttc tcaagtgcct    840
caacccatct ttcaaccctc ctgagaagaa gtgtgccctg gaggatgaaa cgtatgcaga    900
tggagctgag accgaggtgg actgtaaccg ctgtgtctgt gcctgtggaa attgggtctg    960
tacagccatg acctgtgacg gaaagaatca agggggggcc cagacccaga cagaggagga   1020
gatgaccaga tatgtccagg agctccaaaa gcatcaggaa acagctgaaa agaccaagag   1080
agtgagcacc aaagagatct aatgaggagg cacagaccag tgtctggatc ccagcatctt   1140
ctccacttca gcgctgagtt cagtatacac aagtgtctgc tacagtcgcc aaatcaccag   1200
tatttgctta tatagcaatg agttttattt tgtttatttg ttttgcaata aaggatatga   1260
aggtggctgg ctaggaaggg aagggccaca gccttcattt ctaggagtgc tttaagagaa   1320
actgtaaatg gtgctctggg gctggaggct agtaaggaaa ctgcatcacg attgaaagag   1380
gaacagaccc aaatctgaac ctcttttgag tttactgcat ctgtcagcag gctgcaggga   1440
gtgcacacga tgccagagag aacttagcag ggtgtccccg gaggagaggt ttgggaagct   1500
ccacggagag gaacgctctc tgcttccagc ctctttccat tgccgtcagc atgacagacc   1560
tccagcatcc acgcatctct tggtcccaat aactgcctct agatacatag ccatactgct   1620
```

```
agttaaccca gtgtccctca gacttggatg gagtttctgg gagggtacac ccaaatgatg    1680
cagatacttg tatactttga gccccttagc gacctaaccc aattttaaaa atactttta     1740 ccaaaggtgc tatttctctg taaaacactt tttttggca agttgacttt attcttcaat     1800
tattatcatt atattattgt tttttaatat tttattttct tgactaggta ttaagctttt    1860
gtaattattt ttcagtagtc ccaccacttc ataggtggaa ggagtttggg gttcttcctg    1920
gtgcaggggc tgaaataacc cagatgcccc caccctgcca catactagat gcagcccata    1980
gttggccccc ctagcttcca gcagtccact atctgccaga ggagcaaggg tgccttagac    2040
cgaagccagg ggaagaagca tcttcataaa aaactttcaa gatccaaaca ttaatttgtt    2100
tttatttatt ctgagaagtt gaggcaaatc agtattccca aggatggcga caagggcagc    2160
caagcagggc ttaggatatc ccagcctacc aatatgctca ttcgactaac taggagggtg    2220
agttggccct gtctcttctt ttttctggac ctcagtttcc tcagtgagct ggtaagaatg    2280
cactaacctt tgatttgat aagttataaa ttctgtggtt ctgatcattg gtccagaggg     2340
gagataggtt cctgtgattt ttccttcttc tctataaaat aaatgaaatc ttgttactag    2400
aacaagaaat gtcagatggc caaaaacaag atgaccagat ttgatctcag cctgatgacc    2460
ctacaggtcg tgctatgata tggagtcctc atgggtaaag caggaagaga gtgggaaaga    2520
gaaccacccc actctgtctt catatttgca tttcatgttt aacctccggc tggaaataga    2580
aagcattccc ttagagatga ggataaaaga agtttcaga ttcaacaggg ggaagaaaat     2640
ggagatttaa tcctaaaact gtgacttggg gaggtcagtc atttacagtt agtcctgtgt    2700
ctttcgactt ctgtgattat taaccccact cactaccctg tttcagatgc atttggaata    2760
ccaaagatta aatccttgac ataagatctc atttgcagaa agcagattaa agaccatcag    2820
aaggaaatta tttaggttgt aatgcacagg caactgtgag aaactgttgt gccaaaaata    2880
gaattccttc tagttttct tgttctcatt tgaaaggaga aaattccact ttgtttagca     2940
tttcaagctt ttatgtatcc atcccatcta aaaactcttc aaactccact tgttcagtct    3000
gaaatgcagc tccctgtcca agtgccttgg agaactcaca gcagcacgcc ttaatcaaag    3060
gttttaccag cccttggaca ctatgggagg agggcaagag tacaccaatt tgttaaaagc    3120
aagaaaccac agtgtctctt cactagtcat ttagaacatg gttatcatcc aagactactc    3180
taccctgcaa cattgaactc ccaagagcaa atccacattc ctcttgagtt ctgcagcttc    3240
tgtgtaaata gggcagctgt cgtctatgcc gtagaatcac atgatctgag gaccattcat    3300
ggaagctgct aaatagccta gtctggggag tcttccataa agttttgcat ggagcaaaca    3360
aacaggatta aactaggttt ggttccttca gccctctaaa agcatagggc ttagcctgca    3420
ggcttccttg ggctttctct gtgtgtgtag ttttgtaaac actatagcat ctgttaagat    3480
ccagtgtcca tggaaacatt cccacatgcc gtgactctgg actatatcag ttttggaaa     3540 gcagggttcc tctgcctgct aacaagccca cgtggaccag tctgaatgtc tttcctttac    3600
acctatgttt ttaagtagtc aaacttcaag aaacaatcta acaagtttc tgttgcatat     3660 gtgtttgtga acttgtattt gtatttagta ggcttctata ttgcatttaa cttgttttg     3720 taactcctga ttcttccttt tcggatacta ttgatgaata aagaaattaa agtgatggtt    3780
ttggtttcct ttccccaat taaggccaaa taaagtcgtg agaacattac ccatttta      3837
```

<210> SEQ ID NO 3
<211> LENGTH: 18
<212> TYPE: DNA
<213> ORGANISM: Artificial Sequence

```
<220> FEATURE:
<223> OTHER INFORMATION: Synthetic construct

<400> SEQUENCE: 3
aatggatacg gctacagc                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic construct

<400> SEQUENCE: 4
gtgcagcgaa ctttattg                                                 18

<210> SEQ ID NO 5
<211> LENGTH: 17
<212> TYPE: DNA
<213> ORGANISM: Artificial Sequence
<220> FEATURE:
<223> OTHER INFORMATION: Synthetic construct

<400> SEQUENCE: 5
catgccaatg acgacct                                                  17

<210> SEQ ID NO 6
<211> LENGTH: 19
<212> TYPE: DNA
<213> ORGANISM: Artificial Sequence
<220> FEATURE:
<223> OTHER INFORMATION: Synthetic construct

<400> SEQUENCE: 6
cctacactcc tgtactgcc                                                19

<210> SEQ ID NO 7
<211> LENGTH: 26
<212> TYPE: DNA
<213> ORGANISM: Artificial Sequence
<220> FEATURE:
<223> OTHER INFORMATION: Synthetic construct

<400> SEQUENCE: 7
gccaaaacac caacctgtcc aagttc                                        26

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
ctgctggaga ggttattcct cg                                            22

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
aggtccaatt aacttcaccg t                                             21
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
gtcagcatct cccggacata                                                  20

<210> SEQ ID NO 11
<211> LENGTH: 17
<212> TYPE: DNA
<213> ORGANISM: Artificial Sequence
<220> FEATURE:
<223> OTHER INFORMATION: Synthetic construct

<400> SEQUENCE: 11
accgtcttcc tcacact                                                     17

<210> SEQ ID NO 12
<211> LENGTH: 17
<212> TYPE: DNA
<213> ORGANISM: Artificial Sequence
<220> FEATURE:
<223> OTHER INFORMATION: Synthetic construct

<400> SEQUENCE: 12
cttgtctgcc tgggtca                                                     17

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
cctttgctgt ccccgaaga                                                   19

<210> SEQ ID NO 14
<211> LENGTH: 22
<212> TYPE: DNA
<213> ORGANISM: Artificial Sequence
<220> FEATURE:
<223> OTHER INFORMATION: Synthetic construct

<400> SEQUENCE: 14
ggcttctcat ctgttgcttc ct                                               22

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
ccctatttca tctgcgacga g                                                21

<210> SEQ ID NO 16
<211> LENGTH: 19
<212> TYPE: DNA
<213> ORGANISM: Artificial Sequence
<220> FEATURE:
<223> OTHER INFORMATION: Synthetic construct
```

<400> SEQUENCE: 16
gagaaggacg tagcgaccg                                                    19

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
acttgaagta agatacggag g                                                 21

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
gcgtaccctg acaccaatct c                                                 21

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
cgctgtcttg cactctggt                                                    19

<210> SEQ ID NO 20
<211> LENGTH: 21
<212> TYPE: DNA
<213> ORGANISM: Artificial Sequence
<220> FEATURE:
<223> OTHER INFORMATION: Synthetic construct

<400> SEQUENCE: 20
cgttttcggc cctgagatgt t                                                 21

<210> SEQ ID NO 21
<211> LENGTH: 22
<212> TYPE: DNA
<213> ORGANISM: Artificial Sequence
<220> FEATURE:
<223> OTHER INFORMATION: Synthetic construct

<400> SEQUENCE: 21
tcaaacctga gagtgtctaa cg                                                22

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
ccgggccgaa gagatttctg                                                   20

<210> SEQ ID NO 23

```
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
ccctgccacc cttaccaga                                                   19

<210> SEQ ID NO 24
<211> LENGTH: 21
<212> TYPE: DNA
<213> ORGANISM: Artificial Sequence
<220> FEATURE:
<223> OTHER INFORMATION: Synthetic construct

<400> SEQUENCE: 24
gcagatacct cgcaatgtca c                                                21

<210> SEQ ID NO 25
<211> LENGTH: 23
<212> TYPE: DNA
<213> ORGANISM: Artificial Sequence
<220> FEATURE:
<223> OTHER INFORMATION: Synthetic construct

<400> SEQUENCE: 25
acatcaagac atcgtgcgat att                                              23

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
ccagcggtac acaaagacca                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
tcagcaggaa ctttgtcacc                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
aatatgagcc tgaaatgggc                                                  20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
```

-continued

```
<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
gggggtagga ttgacaggat                                                     20

<210> SEQ ID NO 31
<211> LENGTH: 21
<212> TYPE: DNA
<213> ORGANISM: Artificial Sequence
<220> FEATURE:
<223> OTHER INFORMATION: Synthetic construct

<400> SEQUENCE: 31
gaggtcactc ctatcctctg g                                                   21

<210> SEQ ID NO 32
<211> LENGTH: 22
<212> TYPE: DNA
<213> ORGANISM: Artificial Sequence
<220> FEATURE:
<223> OTHER INFORMATION: Synthetic construct

<400> SEQUENCE: 32
gccatttcct ccgactttc tc                                                   22

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
aatgctttct ccgctctgaa                                                     20

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34
gatcatgcgg atcaaacctc                                                     20
```

(Preceding sequence fragment: `tgacacacca caagggctta    20`)

We claim:

1. A method for repairing cardiac tissue following an injury in a subject in need thereof, the method comprising contacting the cardiac tissue with a hypoglycosylated follistatin-like 1 (FSTL1) polypeptide, wherein the hypoglycosylated FSTL1 polypeptide a) is an FSTL1 polypeptide that lacks N-linked glycosylation at one or more glycosylation-competent asparagine residues; or b) is an FSTL1 polypeptide comprising substitution of one or more glycosylation-competent asparagine residues with glycosylation-incompetent residues.

2. The method of claim 1, wherein the injury a) is an ischemia reperfusion cardiac injury; b) is due to ischemic heart disease; c) is due to a hypoplastic heart; and/or d) is due to myocardial infarction, wherein the heart optionally contains scar tissue.

3. The method of claim 1, wherein repairing cardiac tissue comprises one or more of a) increasing the number of cardiomyocytes in the cardiac tissue; b) recovery of damaged cardiac tissue, including cardiomyocytes and/or cardiac vasculature; c) improved percent fractional shortening of cardiac tissue compared to the amount of percent fractional shortening in cardiac tissue that is not contacted by the hypoglycosylated FSTL1 polypeptide following an injury; d) a reduction in scar area (fibrosis) of at least a 2% compared to the amount of fibrosis in the same heart prior to the treatment by contacting, delivering or genomic editing of the hypoglycosylated FSTL1 polypeptide following an injury; e) an increase in vascular perfused area of at least a 2% compared to the amount of perfused area in the same heart prior to the treatment by contacting, delivering or genomic editing of the hypoglycosylated FSTL1 polypeptide following an injury; f) an increase in the amount of cardiomyocyte cytokinesis in the cardiac tissue compared to the amount of cardiomyocyte cytokinesis in cardiac tissue that is not contacted by the hypoglycosylated FSTL1 polypeptide following an injury, wherein the amount of cardiomyocyte cytokinesis is optionally determined by expression of Aurora B kinase; and/or g) decreased cardiomyocyte apoptosis.

4. The method of claim 3, wherein the number of cardiomyocytes is increased at least three fold compared to the number of cardiomyocytes in cardiac tissue that is not contacted by the hypoglycosylated FSTL1 polypeptide following an injury.

5. The method of claim 1, wherein said method results in one or more of a) increased levels of transcripts encoding cardiac-specific contractile proteins in cardiomyocytes; b) a 2 fold increase in the levels of transcripts encoding cardiac-specific contractile proteins in cardiomyocytes, wherein said cardiac-specific contractile proteins are optionally selected from the group consisting of myh6, mlc2v, and mlc2a; c) increased actinin$^+$ cells with rhythmic contractile Ca$^{2+}$ in cardiomyocytes; d) decreased cardiac events and hospitalizations; e) attenuated fibrosis in the cardiac tissue following the injury; f) increased vascularization of the injured region of the cardiac tissue, wherein increased vascularization is optionally determined by expression of von Willebrand factor (vWF) or smooth muscle actin in blood vessel cells; g) induction of cardiomyocyte cell cycle entry, wherein cardiomyocyte cell cycle entry is optionally assessed by expression of phosphor-Histone H3; and/or h) an at least 2 fold increase in cardiomyocyte cell cycle entry compared to the amount of cardiomyocyte cell cycle entry in cardiac tissue that is not contacted by the hypoglycosylated FSTL1 polypeptide following an injury.

6. The method of claim 1, wherein a) the cardiac tissue is contacted with said hypoglycosylated FSTL1 polypeptide immediately following the injury; b) the cardiac tissue is contacted with said hypoglycosylated FSTL1 polypeptide any time after the injury c) the hypoglycosylated FSTL1 polypeptide is delivered by a collagen patch into the injured myocardial tissue; d) the hypoglycosylated FSTL1 polypeptide is injected directly into the injured myocardial tissue; e) the hypoglycosylated FSTL1 polypeptide is delivered systemically; f) the hypoglycosylated FSTL1 polypeptide is delivered endocardially, optionally via a catheter; g) the hypoglycosylated FSTL1 polypeptide is catheter delivered using drug-eluting stent; h) the hypoglycosylated Fstl1 polypeptide is embedded or seeded into a three dimensional collagen patch; i) the cardiac tissue is contacted from one or more of an epicardial site, an endocardial site, and/or through direct injection into the myocardium; j) the hypoglycosylated FSTL1 polypeptide is expressed in the heart by the use of modifiedRNAs (modRNAs); k) the hypoglycosylated FSTL1 polypeptide is expressed by genomic editing; l) the hypoglycosylated FSTL1 polypeptide is embedded or seeded into a hydrogel; or m) the hypoglycosylated FSTL1 polypeptide is mixed with gelfoam particles.

7. The method of claim 1, wherein said hypoglycosylated FSTL1 polypeptide is a) synthesized in a prokaryotic cell; or b) synthesized in a eukaryotic cell that is treated with an inhibitor of glycosylation.

8. A sterile pharmaceutical composition comprising a hypoglycosylated follistatin-like 1 (FSTL1) polypeptide and one or more pharmaceutically acceptable excipients, wherein the hypoglycosylated FSTL1 polypeptide a) is an FSTL1 polypeptide that lacks N-linked glycosylation at one or more glycosylation-competent asparagine residues; or b) is an FSTL1 polypeptide comprising substitution of one or more glycosylation-competent asparagine residues with glycosylation-incompetent residues.

9. The sterile pharmaceutical composition of claim 8, further comprising an inhibitor of FSTL1 glycosylation, wherein said inhibitor of FSTL1 glycosylation optionally comprises tunicamycin.

10. The sterile pharmaceutical composition of claim 8, wherein said hypoglycosylated FSTL1 polypeptide is a) synthesized in a prokaryotic cell, wherein said prokaryotic cell is optionally a bacterial cell; b) synthesized in a eukaryotic cell that is treated with an inhibitor of glycosylation, wherein said inhibitor of glycosylation optionally comprises tunicamycin.

11. The sterile pharmaceutical composition of claim 8, wherein the composition is a) formulated for injection directly into the injured cardiac tissue; b) formulated for systemic administration; or c) synthesized in a cell comprising modifiedRNAs (modRNAs); d) is expressed by genomic editing.

12. The sterile pharmaceutical composition of claim 8, wherein the hypoglycosylated FSTL1 polypeptide is embedded or seeded into a three dimensional (3D) collagen patch, wherein the 3D collagen patch optionally has an elastic modulus of 12±4 kPa.

13. A kit comprising (i) a hypoglycosylated follistatin-like 1 (FSTL1) polypeptide, wherein the hypoglycosylated FSTL1 polypeptide a) is an FSTL1 polypeptide that lacks N-linked glycosylation at one or more glycosylation-competent asparagine residues; or b) is an FSTL1 polypeptide comprising substitution of one or more glycosylation-competent asparagine residues with glycosylation-incompetent residues; and (ii) one or more pharmaceutically acceptable excipients; and optionally one or more of (iii) a three dimensional (3D) collagen patch, wherein a) the hypoglycosylated FSTL1 polypeptide is optionally embedded or seeded into the 3D collagen patch; and b) wherein the 3D collagen patch optionally has an elastic modulus of 12±4 kPa; and/or (iv) adhesion means for adhering the 3D collagen patch to the epicardium or to the myocardium of an injured heart, wherein the adhesion means are optionally sutures.

14. The method of claim 1, wherein
a) the hypoglycosylated FSTL1 polypeptide lacks N-linked glycosylation at one or more asparagine residues corresponding to positions 144, 175, 180, and 223 in the FSTL1 amino acid sequence of SEQ ID NO: 1; or
b) the hypoglycosylated FSTL1 polypeptide comprises substitution of one or more asparagine residues corresponding to positions 144, 175, 180, and 223 in the FSTL1 amino acid sequence of SEQ ID NO: 1 with glycosylation-incompetent residues.

15. The method of claim 14, wherein
a) the hypoglycosylated FSTL1 polypeptide lacks N-linked glycosylation at an asparagine residue corresponding to position 180 in the FSTL1 amino acid sequence of SEQ ID NO: 1; or
b) the hypoglycosylated FSTL1 polypeptide comprises substitution of an asparagine residue corresponding to position 180 in the FSTL1 amino acid sequence of SEQ ID NO: 1 with a glycosylation-incompetent residue.

* * * * *